(12) United States Patent
Barzani

(10) Patent No.: US 12,029,772 B2
(45) Date of Patent: Jul. 9, 2024

(54) WILLOW EXTRACT AND ITS USE IN TREATING A VIRAL INFECTION, ALLERGIC REACTION, AND OTHER MEDICAL CONDITIONS

(71) Applicants: Mustafa Barzani, McLean, VA (US); Shireen Nature Company for General Trading, Ltd., McLean, VA (US)

(72) Inventor: Mustafa Barzani, McLean, VA (US)

(73) Assignees: Mustafa Barzani, McLean, VA (US); Shireen Nature Company for General Trading Ltd., Erbil (IQ)

( * ) Notice: Subject to any disclaimer, the term of this patent is extended or adjusted under 35 U.S.C. 154(b) by 50 days.

(21) Appl. No.: 17/706,865

(22) Filed: Mar. 29, 2022

(65) Prior Publication Data

US 2022/0323531 A1   Oct. 13, 2022

Related U.S. Application Data

(60) Provisional application No. 63/323,810, filed on Mar. 25, 2022, provisional application No. 63/279,842, filed on Nov. 16, 2021, provisional application No. 63/167,166, filed on Mar. 29, 2021.

(51) Int. Cl.

| | |
|---|---|
| A61K 36/00 | (2006.01) |
| A61K 9/00 | (2006.01) |
| A61K 9/48 | (2006.01) |
| A61K 31/192 | (2006.01) |
| A61K 31/353 | (2006.01) |
| A61K 31/427 | (2006.01) |
| A61K 31/4965 | (2006.01) |
| A61K 31/513 | (2006.01) |
| A61K 31/517 | (2006.01) |
| A61K 31/675 | (2006.01) |
| A61K 31/7034 | (2006.01) |
| A61K 31/7048 | (2006.01) |
| A61K 31/7068 | (2006.01) |
| A61K 36/76 | (2006.01) |
| A61K 38/17 | (2006.01) |
| A61K 38/21 | (2006.01) |
| A61K 39/395 | (2006.01) |
| A61K 39/42 | (2006.01) |
| A61P 31/14 | (2006.01) |

(52) U.S. Cl.
CPC ............ *A61K 36/76* (2013.01); *A61K 9/0053* (2013.01); *A61K 9/48* (2013.01); *A61K 31/192* (2013.01); *A61K 31/353* (2013.01); *A61K 31/427* (2013.01); *A61K 31/4965* (2013.01); *A61K 31/513* (2013.01); *A61K 31/517* (2013.01); *A61K 31/675* (2013.01); *A61K 31/7034* (2013.01); *A61K 31/7048* (2013.01); *A61K 31/7068* (2013.01); *A61K 38/1774* (2013.01); *A61K 38/21* (2013.01); *A61K 39/3955* (2013.01); *A61K 39/42* (2013.01); *A61P 31/14* (2018.01); *A61K 2236/15* (2013.01); *A61K 2236/37* (2013.01); *A61K 2236/39* (2013.01); *A61K 2236/51* (2013.01); *A61K 2236/53* (2013.01)

(58) Field of Classification Search
CPC ...................................................... A61K 36/76
See application file for complete search history.

(56) References Cited

U.S. PATENT DOCUMENTS

| | | |
|---|---|---|
| 7,083,814 B2 | 8/2006 | Ilic et al. |
| 7,959,951 B2 | 6/2011 | Stefano et al. |
| 2022/0105110 A1 | 4/2022 | Lalvani et al. |

FOREIGN PATENT DOCUMENTS

| | | |
|---|---|---|
| CN | 104127701 A | 11/2014 |
| CN | 104288681 A | 1/2015 |
| CN | 107397817 A * | 11/2017 |

OTHER PUBLICATIONS

Zhang et al., Studies on pharmacology of chemical constituents of leaves of Salix matsudana. Journal of Jilin Agricultural University (2001), vol. 23, No. 1, pp. 54-57 (Year: 2001).*
Third Party Observations in PCT/US2022/022233 citing (i) Bhavamisra in Part-I: Chaukhambha Sanskrit Sansthan, Varanasi, Edn. 9th, 1999, (ii) Khan in Qaraabaadeen Azam wa Akmal (19th) century AD, and (iii) Khan in Qaraabaadeen Najm-al-Ghani (20th century AD).
Altinterim, B., "Effects of Willow Bark (Salix alba) and its Salicylates on Blood Coagulant," *Karaelmas Science and Engineering*, Journal 3, vol. 1. pp. 37-39 (2013).
Assessment Report "European Union herbal monograph on Salix [various species including *S. purpurea* L., S. daphnoides Vill., *S. fragilis* L.], cortex" Committee on Herbal Medicinal Products (HMPC) (Jan. 31, 2017).
Assessment Report on Salicis Cortex (Willow Bark) and Herbal Preparation(s) Thereof with Well-Established Use and Traditional Use, *EMEA*, pp. 1-27 (2009).
Assessment report on Salix [various species including *S. purpurea* L., S. daphnoides Vill., *S. fragilis* L.], cortex, European Medicines Agency, pp. 1-55 (2017).
Azienda Ospedaliera Universitaria Integrata Verona: "Acetylsalicylic Acid in the Prevention of Severe SARS-COV2 Pneumonia in Hospitalised Patients With COVID-19 (Asperum)," ClinicalTrials. gov, NCT04808895, Mar. 22, 2021, URL: https://clinicaltrials.gov/ct2/show/NCT04808895#contacts [retrieved online May 17, 2022] p. 2/15, Brief Summary; p. 4/15, Arms and Intervention.
Blake, S., et al., 'Salicylanilides Reduce SARS-COV-2 Replication and Suppress Induction of Inflammatory Cytokines in a Rodent Model, Steven', ACS Infectious Diseases 2021 7 (8), 2229-2237, DOI: 10.1021/acsinfecdis.1c00253, Abstract; p. 2230, Table 1.

(Continued)

*Primary Examiner* — Qiuwen Mi
(74) *Attorney, Agent, or Firm* — Dechert LLP

(57) ABSTRACT

The invention provides therapeutic compositions containing willow extract, such as willow leaf extract, methods of medical treatment using such compositions, and methods for preparing such compositions.

28 Claims, 9 Drawing Sheets

(56) References Cited

OTHER PUBLICATIONS

Bonaterra, G.A., et al., "In vitro anti-proliferative effects of the willow bark extract STW 33-I," *Arzneimittelforschung*, vol. 60, pp. 330-335 (2010).

Dissanayake A. A et al., "Salicylic Glycosides in Salix mucronata with Antioxidant and Antiinflammatory Activities," *Natural Product Communications*, vol. 12 (11), pp. 1755-1758 (2017).

El-Shemy, H.A. et al., " Willow Leaves' Extracts Contain Anti-Tumor Agents Effective Against Three Cell Types," *Plos One*, Issue 1, pp. 1-5 (2007).

El-Shemy, H.A., et al., "The Effect of Willow Leaf Extracts on Human Leukemic Cells in Vitro," *Journal of Biochemistry and Molecular Biology*, vol. 36, No. 4, pp. 387-389 (2003).

European Union herbal monograph on Salix [various species including S. purpurea L., S. Daphnoides Vill., S. fragilis L.], cortex, *EMA*, pp. 1-9 (2017).

Feistel, F. et al., "The Absolute Configuaration of Salicortin HCH-Salicortin and Tremulacin from Populus trichocarpa x deltoides Beaupre," *Molecules*, pp. 5566-5573 (2015).

International Search Report and Written Opinion for International Application No. PCT/US2022/022263, dated May 27, 2022.

Julkunen-Tiitto, R. and Meier, B., "The enzymatic decomposition of salicin and its derivaives obtaine from Salicaceae species," *J. Nat. Prod.* (1992) (Abstract only).

Kammerer, B. et al., "HPLC-MS/MS Analysis of Willow Bark Extracts Contained in Pharmaceutical Preparations," *Phytochem. Anal.*, pp. 470-478 (2005).

Krivoy, N. et al., "Effect of salicis cortex extract on human platelet aggregation," *Planta. Med.*, one page, (2001). (Abstract only).

Le, N.P.K. et al., Comparative Anti-Inflammatory Effects of Salix Cortex Extracts and Acetylsalicylic Acid in SARS-CoV-2 Peptide and LPS-Activated Human In Vitro Systems, Int. J. Mol. Sci., vol. 22, 6766 (2021).

Li, Y. et al., "D(-)-Salicin inhibits the LPS-induced inflammation in RAW264.7 cells and mouse models," *Int. Immunopharma.*, vol. 26, pp. 286-294 (2015).

Mahdi, J.G. et al., "The historical analysis of aspirin in discovery, its relation to the willow tree and antiproliferative and anticancer potential," *Cell Prolif.*, vol. 39, pp. 147-155 (2006).

Mahdi, J.G., "Medicinal potential of willow: A chemical perspective of aspirin discovery," Journal of Saudi Chemical Society, vol. 14, pp. 317-322 (2010).

Maistro, E.L. et al., "Salix alba (white willow) medicinal plant presents genotoxic effects in human cultured leukocytes," *J. Toxicol Environ Health A.*, pp. 1223-1234 (Abstract only).

Oketch-Rabah, H.A. et al., "United States Pharmacopeia Safety Review of Willow Bark," U.S. Pharmacopeia, vol. 85, pp. 1192-1202 (2019).

Paterson, J.R. and Lawrence, J.R., "Salicylic acid: a link between aspirin, die and the prevention of colorectal cancer," *Q. J. Med.*, vol. 94, pp. 445-448 (2001).

Salicin, Wikipedia, Retrieved from "https://en.wikipedia.org/w/index.php?title=Salicin&oldid=1009452861", 3 pages (Apr. 2021).

Salix alba, Wikipedia, Retrieved from "https://en.wikipedia.org/w/index.php?title=Salix_alba&oldid=1010436970", 4 pages (Apr. 2021).

Schmid, B. et al., "Pharmacokinetics of salicin after oral administration of a standardised willow bark extract," *Eur. J. Clin. Pharmacol.*, vol. 57, pp. 387-391 (2001).

Shara, M. and Stohs, S.J., "Efficacy and Safety of White Willow Bark (Salix alba) Extracts," *Phytother. Res.*, vol. 29, pp. 1112-1116 (2015).

Silveira, D. et al., "COVID-19: Is There Evidence for the Use of Herbal Medicines as Adjuvant Symptomatic Therapy?," *Front. Pharmacol.*, vol. 11, pp. 1-44 (2020).

Song, Y. et al., "Vasculat protection of salicin on IL-1B-induced endothelial inflammatory response and damages in retinal endothelial cells," *Artificial Cells*, vol. 47, No. 1, pp. 1995-2002 (2019).

Tawfeek, N. et al., "Phytochemistry, Pharmacology and Medicinal Uses of Plants of the Genus Salix: An Updated Review," Frontiers in Pharmacology, vol. 12, pp. 1-30 (2021).

Vlachojannis, J. et al., "Willow Species and Aspirin: Different Mechanism of Actions," *Phytotherapy Research*, vol. 25, pp. 1102-1104 (2011) (Abstract only).

Willow, Wikipedia, Retrieved from "https://en.wikipedia. org/w/index.php?title=Willow&oldid=1011773794", 10 pages (Apr. 2021).

World Health Organization, Monographs on Selected Medicinal Plants 4 (2009).

Xijing Hospital: "Protective Effect of Aspirin on COVID-19 Patients (PEAC)," *ClinicalTrials.gov*, NCT04365309, Apr. 28, 2020, URL: https://clinicaltrials.gov/ct2/show/NCT04365309 [retrieved online May 17, 2022] pp. 1/7-2/7, Brief Summary.

* cited by examiner

WILLOW EXTRACT AND ITS USE IN TREATING A VIRAL INFECTION, ALLERGIC REACTION, AND OTHER MEDICAL CONDITIONS

CROSS-REFERENCE TO RELATED APPLICATIONS

This application claims the benefit of and priority to U.S. Provisional Patent Application Ser. No. 63/323,810, filed Mar. 25, 2022; U.S. Provisional Patent Application Ser. No. 63/279,842, filed Nov. 16, 2021; and U.S. Provisional Patent Application Ser. No. 63/167,166, filed Mar. 29, 2021; the contents of each of which are hereby incorporated by reference in their entirety.

FIELD OF THE INVENTION

The invention provides therapeutic compositions containing willow extract, such as willow leaf extract, methods of medical treatment using such compositions, and methods for preparing such compositions.

BACKGROUND

Coronaviruses can infect the upper respiratory and/or gastrointestinal tract of birds and mammals, including humans. Coronaviruses are believed to cause a significant percentage of all common colds in human adults and children. Coronaviruses, including the OC43 virus, can cause colds with major symptoms, e.g., fever, throat congestion and adenoids, in humans primarily in the winter and early spring seasons. Coronaviruses can also cause pneumonia, either direct viral pneumonia or a secondary bacterial pneumonia, bronchitis, either direct viral bronchitis or a secondary bacterial bronchitis, and severe acute respiratory syndrome (SARS).

A recently discovered coronavirus, severe acute respiratory syndrome coronavirus 2 (SARS-CoV-2), has caused a pandemic threatening the health and economy of many countries throughout the world. Common symptoms reported in the literature for infection by a SARS-CoV-2 include fever, dry cough, shortness of breath, and loss of smell. Complications may include pneumonia, viral sepsis, acute respiratory distress syndrome, diarrhea, renal disease, cardiac issues, and encephalitis. Current treatment options for SARS-CoV-2, such as molnupiravir, PAXLOVID™ (containing nirmatrelvir and ritonavir), remdesivir or bamlanivimab and etesevimab, are not effective for all patients and/or can have substantial adverse side effects.

Other respiratory conditions resulting in inflammation and swelling of the airways leading to the lungs, frequently resulting in shortness of breath, affect a substantial number of patients. Existing treatments for such respiratory conditions are not effective for all patients and/or can have substantial adverse side effects.

Accordingly, the need exists for new therapeutic methods that provide improved efficacy and/or reduced side effects for treating medical conditions, such as SARS-CoV-2. The present invention addresses the foregoing needs and provides other related advantages.

SUMMARY

The invention provides therapeutic compositions containing willow extract, such as willow leaf extract, methods of medical treatment using such compositions, and methods for preparing such compositions. The willow leaf extract can be orally administered to patients, and provides treatment of a SARS-CoV-2 infection in patients. Procedures for isolating the willow leaf extract and treating patients suffering from a coronavirus infection and other medical conditions are provided. Various aspects and embodiments of the invention are described below.

One aspect of the invention provides a method of treating a condition selected from a coronavirus infection and allergic reaction in a patient. The method comprises orally administering to a patient in need thereof a therapeutically effective amount of a therapeutic composition comprising a willow leaf extract, to treat the condition. Exemplary dosing amounts and dosing regimens are provided herein.

Another aspect of the invention provides a method of reducing inflammation in a patient suffering from a coronavirus infection. The method comprises orally administering to a patient in need thereof a therapeutically effective amount of a therapeutic composition comprising a willow leaf extract, in order to reduce inflammation. Exemplary dosing amounts and dosing regimens are provided herein.

Another aspect of the invention provides a method of reducing the impact of a pro-inflammatory cytokine in a patient suffering from a coronavirus infection. The method comprises orally administering to a patient in need thereof a therapeutically effective amount of a therapeutic composition comprising a willow leaf extract, in order to reduce the impact of the pro-inflammatory cytokine. Exemplary dosing amounts and dosing regimens are provided herein.

Another aspect of the invention provides a method of treating a respiratory condition. The method comprises orally administering to a patient in need thereof a therapeutically effective amount of a therapeutic composition comprising a willow leaf extract, to treat the respiratory condition. Exemplary dosing amounts and dosing regimens are provided herein.

The foregoing methods may be further characterized according to, for example, patients for treatment, features of the willow leaf extract, and the identity of the willow leaf extract. These and other features are described in more detail herein below.

Another aspect of the invention provides a method for the treatment or prophylaxis of a condition selected from a coronavirus infection and allergic reaction in a patient. The method comprises orally administering to said patient in need thereof a therapeutically effective amount of a therapeutic composition comprising a willow extract. Exemplary dosing amounts and dosing regimens are provided herein.

Another aspect of the invention provides a method of reducing inflammation in a patient suffering from a coronavirus infection. The method comprises orally administering to a patient in need thereof a therapeutically effective amount of a therapeutic composition comprising a willow extract, in order to reduce inflammation. Exemplary dosing amounts and dosing regimens are provided herein.

Another aspect of the invention provides a method of reducing the impact of a pro-inflammatory cytokine in a patient suffering from a coronavirus infection. The method comprises orally administering to a patient in need thereof a therapeutically effective amount of a therapeutic composition comprising a willow extract, in order to reduce the impact of the pro-inflammatory cytokine. Exemplary dosing amounts and dosing regimens are provided herein.

Another aspect of the invention provides a method of treating a respiratory condition. The method comprises orally administering to a patient in need thereof a therapeutically effective amount of a therapeutic composition comprising a willow extract, to treat the respiratory condition. Exemplary dosing amounts and dosing regimens are provided herein.

The foregoing methods may be further characterized according to, for example, patients for treatment, features of the willow extract, and the identity of the willow extract. These and other features are described in more detail herein below.

Another aspect of the invention provides a method for preparing a willow leaf extract. The method comprises the steps of:

a. obtaining leaves that have been harvested from a willow tree;
b. incubating said leaves in water at a temperature in excess of 50° C. to provide a mixture;
c. filtering the mixture produced from step (b) to isolate a liquid fraction;
d. exposing the liquid fraction to a temperature greater than ambient temperature to cause evaporation of water from the liquid fraction, thereby forming a paste; and
e. drying the paste to provide willow leaf extract.

The method may be further characterized by additional features, such as, for example, additional features of the steps described above, additional steps the method may include, and the identity of the willow leaves. These and other features are described in more detail herein below.

An additional aspect of the invention provides a willow leaf extract prepared according to a method described above. Still another aspect of the invention provides a pharmaceutical composition comprising a willow leaf extract and a pharmaceutically acceptable carrier.

DETAILED DESCRIPTION OF THE INVENTION

Figure 1:
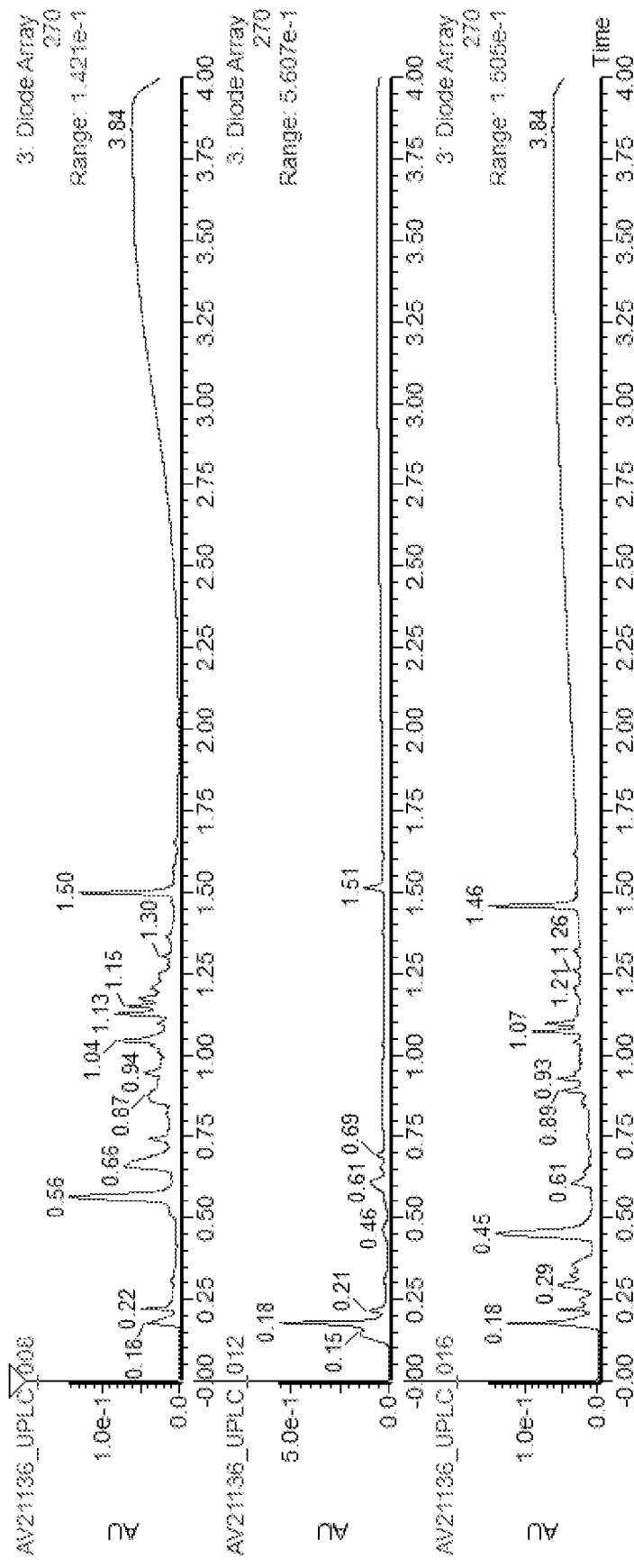
FIG. 1 depicts results of ultra performance liquid chromatography (UPLC) of a willow leaf extract varying the additive in the aqueous mobile phase, as described in Example 3.

The invention provides therapeutic compositions containing willow extract, such as willow leaf extract, methods of medical treatment using such compositions, and methods for preparing such compositions. The willow leaf extract can be orally administered to patients, and provides treatment of a SARS-CoV-2 infection in patients. Procedures for isolating the willow leaf extract and treating patients suffering from a coronavirus infection and other medical conditions are provided. Various aspects of the invention are set forth below in sections; however, aspects of the invention described in one particular section are not to be limited to any particular section.

Definitions

To facilitate an understanding of the present invention, a number of terms and phrases are defined below.

The terms "a" and "an" as used herein mean "one or more" and include the plural unless the context is inappropriate.

As used herein, the terms "subject" and "patient" refer to organisms to be treated by the methods of the present invention. Such organisms are preferably mammals (e.g., murines, simians, equines, bovines, porcines, canines, felines, and the like), and more preferably humans.

As used herein, the term "effective amount" refers to the amount of a therapeutic composition sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof. As used herein, the term "treatment" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

The phrase "therapeutically effective amount" as used herein means that amount of a compound, material, or composition comprising a compound or willow leaf extract of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S.

M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Further, acids which are generally considered suitable for the formation of pharmaceutically useful salts from basic pharmaceutical compounds are discussed, for example, by P. Stahl et al., Camille G. (eds.) Handbook of Pharmaceutical Salts. *Properties, Selection and Use*. (2002) Zurich: Wiley-VCH; S. Berge et al., *Journal of Pharmaceutical Sciences* (1977) 66(1) 1-19; P. Gould, *International J. of Pharmaceutics* (1986) 33 201-217; Anderson et al., *The Practice of Medicinal Chemistry* (1996), Academic Press, New York; and in *The Orange Book* (Food & Drug Administration, Washington, D.C. on their website). These disclosures are incorporated herein by reference.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

The term "about" means±10% of the stated value, unless specified otherwise. In certain more specific embodiments, "about" a stated value may be ±9%, ±8%, ±7%, ±6%, ±5%, ±3%, ±2%, or ±1% of the stated value.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

I. Therapeutic Applications

The invention provides methods of treating medical conditions, such as a coronavirus infection, allergic reaction, or respiratory condition, by administering willow extract, such as willow leaf extract to a patient. The invention also provides methods more specifically directed to reducing inflammation, or reducing the impact of a pro-inflammatory cytokine, in a patient suffering from a coronavirus infection. Various aspects and embodiments of the therapeutic methods are described in the sections below. The sections are arranged for convenience and information in one section is not to be limited to that section but may be applied to methods in other sections. All combinations and permutations of the embodiments described below are contemplated.

First Therapeutic Method

One aspect of the invention provides a method of treating a condition selected from a coronavirus infection and allergic reaction in a patient. The method comprises orally administering to a patient in need thereof a therapeutically effective amount of a therapeutic composition comprising a willow leaf extract, to treat the condition.

The method may be further characterized according to additional features, such as the condition to be treated. For example, in certain embodiments, the condition is a coronavirus infection. In certain embodiments, the condition is an allergic reaction. In certain embodiments, the condition is a respiratory allergic reaction. In certain embodiments, the condition is a respiratory allergic reaction due to an airborne allergen. In certain embodiments, the condition is an allergic reaction due to a food allergy. In certain embodiments, the condition is a dermatological allergic reaction.

In certain embodiments, the willow leaf extract is the only active ingredient for treating the condition in the therapeutic composition.

In certain embodiments, the therapeutic composition contains at least one additional active ingredient for treating the condition, in addition to the willow leaf extract.

Second Therapeutic Method

Another aspect of the invention provides a method of reducing inflammation in a patient suffering from a coronavirus infection. The method comprises orally administering to a patient in need thereof a therapeutically effective amount of a therapeutic composition comprising a willow leaf extract, in order to reduce inflammation.

The method may be further characterized according to additional features, such as the presence of any additional active ingredients in the therapeutic composition. For example, in certain embodiments, the willow leaf extract is the only active ingredient for reducing inflammation in the therapeutic composition. In certain other embodiments, the therapeutic composition contains at least one additional active ingredient for reducing inflammation, in addition to the willow leaf extract.

Third Therapeutic Method

Another aspect of the invention provides a method of reducing the impact of a pro-inflammatory cytokine in a patient suffering from a coronavirus infection. The method comprises orally administering to a patient in need thereof a therapeutically effective amount of a therapeutic composition comprising a willow leaf extract, in order to reduce the impact of the pro-inflammatory cytokine.

The method may be further characterized according to additional features, such as presence of any additional active ingredients in the therapeutic composition. For example, in certain embodiments, the willow leaf extract is the only active ingredient for reducing the impact of a pro-inflammatory cytokine in the therapeutic composition. In certain other embodiments, the therapeutic composition contains at least one additional active ingredient for reducing the impact of a pro-inflammatory cytokine, in addition to the willow leaf extract.

In certain embodiments, the pro-inflammatory cytokine is IL-1, IL-2, IL-6, IL-7, or IL-18. In certain embodiments, the pro-inflammatory cytokine is IL-1, IL-2, IL-6, or IL-7. In certain embodiments, the pro-inflammatory cytokine is IL-1. In certain embodiments, the pro-inflammatory cytokine is IL-1β. In certain embodiments, the pro-inflammatory cytokine is IL-2. In certain embodiments, the pro-inflammatory cytokine is IL-6. In certain embodiments, the pro-inflammatory cytokine is IL-7. In certain embodiments, the pro-inflammatory cytokine is IL-18.

In certain embodiments, the pro-inflammatory cytokine is IL-1, IL-2, IL-7, IL-6, IL-18, granulocyte-macrophage colony-stimulating factor (GM-CSF), vascular endothelial growth factor (VEGF), interferon-I (IFN-I), interferon-α (IFN-α), interferon-β (IFN-β), interferon-γ inducible protein 10 (IP-10), monocyte chemoattractant protein 1 (MCP-1), macrophage inflammatory protein 1-α (MIP-1α), or tumor necrosis factor-α (TNF-α). In certain embodiments, the pro-inflammatory cytokine is interferon-I (IFN-I), interferon-α (IFN-α), or interferon-β (IFN-β).

In certain embodiments, the pro-inflammatory cytokine is IL-2, IL-7, IL-6, granulocyte-macrophage colony-stimulating factor (GM-CSF), interferon-γ inducible protein 10 (IP-10), monocyte chemoattractant protein 1 (MCP-1), macrophage inflammatory protein 1-α (MIP-1α), or tumor necrosis factor-α (TNF-α). In certain embodiments, the pro-inflammatory cytokine is granulocyte-macrophage colony-stimulating factor (GM-CSF), interferon-γ inducible protein 10 (IP-10), monocyte chemoattractant protein 1 (MCP-1), macrophage inflammatory protein 1-α (MIP-1α), or tumor necrosis factor-α (TNF-α).

In certain embodiments, the impact of pro-inflammatory cytokine comprises increased inflammation. In certain embodiments, the impact of pro-inflammatory cytokine comprises respiratory failure, septic shock, fibrosis, and/or multi-organ failure. In certain embodiments, the impact of pro-inflammatory cytokine comprises fibrosis.

Fourth Therapeutic Method

Another aspect of the invention provides a method of treating a respiratory condition. The method comprises orally administering to a patient in need thereof a therapeutically effective amount of a therapeutic composition comprising a willow leaf extract, to treat the respiratory condition.

The method may be further characterized according to additional features, such as the respiratory condition and the presence of any additional active ingredients in the therapeutic composition. For example, in certain embodiments, the respiratory condition is shortness of breath. In certain embodiments, the willow leaf extract is the only active ingredient for treating the condition in the therapeutic composition. In certain other embodiments, the therapeutic composition contains at least one additional active ingredient for treating the condition, in addition to the willow leaf extract.

Fifth Therapeutic Method

Another aspect of the invention provides a method of treating a medical condition. The method comprises administering to a patient in need thereof a therapeutically effective amount of a willow leaf extract, to treat the medical condition.

The method may be further characterized according to additional features, such as the identity of the medical condition (e.g., where the medical condition is a coronavirus infection) and the presence of any additional active ingredients in the therapeutic composition. For example, in certain embodiments, the willow leaf extract is the only active ingredient for treating the condition in the therapeutic composition. In certain other embodiments, the therapeutic composition contains at least one additional active ingredient for treating the medical condition, in addition to the willow leaf extract.

Additional Features of the First, Second, Third, and Fifth Therapeutic Methods

Additional exemplary features that may characterize the First, Second, Third, and Fifth Therapeutic Methods described herein are provided below and include, for example, the identity of the coronavirus infection and symptoms experienced by the patient. A more thorough description of such features is provided below. The invention embraces all permutations and combinations of these features.

Identity of Coronavirus

The methods may be further characterized according to the identity of the coronavirus infection. For example, in certain embodiments, the coronavirus infection is an infection by a severe acute respiratory syndrome-related coronavirus (SARSr-CoV). In certain embodiments, the coronavirus infection is an infection by a Sarbecovirus (beta-CoV lineage B). In certain embodiments, the coronavirus infection is an infection by SARS-CoV-2.

In certain embodiments, the coronavirus infection is an infection by a variant of SARS-CoV-2. In certain embodiments, the coronavirus infection is an infection by a variant of SARS-CoV-2 having the spike protein of SARS-CoV-2. In certain embodiments, the coronavirus infection is an infection by SARS-CoV-2 or a variant thereof selected from B.1.351, Cluster 5, Lineage B.1.1.207, Lineage B.1.1.7, Variant of Concern 202102/02, Lineage B.1.1.317, Lineage B.1.1.318, Lineage B.1.351, Lineage B.1.429, Lineage B.1.525, Lineage P.1, D614G, E484K, N501Y, S477G/N, and P681H. In certain embodiments, the coronavirus infection is an infection by SARS-CoV-2 or a variant thereof selected from B.1.617.2. In certain embodiments, the coronavirus infection is an infection by SARS-CoV-2 or a variant thereof selected from B.1.1.529, BA.2, C.37, B.1.621, B.1.429, B.1.427, CAL.20C, P.2, B.1.525, P.3, B.1.526, B.1.617.1, AZ.5, C.1.2, B.1.526, B.1.630, and B.1.640. In certain embodiments, the coronavirus infection is an infection by SARS-CoV-2 or a variant thereof selected from B.1.1.529 and BA.2.

In certain embodiments, the coronavirus infection is an infection by SARS-CoV-2 or variant thereof having a mutation at 1, 2, 3, 4, or 5 amino acids. In certain embodiments, the coronavirus infection is an infection by SARS-CoV-2 or variant thereof having a mutation at up to 10 amino acids. In certain embodiments, the coronavirus infection is an infection by SARS-CoV-2 or variant thereof having a mutation at up to 25 amino acids. In certain embodiments, the coronavirus infection is an infection by SARS-CoV-2 or variant thereof having a mutation at up to 35, 45, 55, or 65 amino acids.

Symptoms Experienced by the Patient

The methods may be further characterized according to symptoms experienced by the patient. For example, in certain embodiments, the patient presents with inflammation due to the coronavirus infection. In certain embodiments, the patient has inflammation in pulmonary tissue. In certain embodiments, the patient has mild or moderate respiratory distress. In certain embodiments, the patient has severe respiratory distress. In certain embodiments, the patient has pneumonia. In certain embodiments, the patient presents with one or more of respiratory failure, septic shock, or multi-organ failure. In certain embodiments, the patient is experiencing a hyper-immune response.

Additional Features of the First, Second, Third, Fourth, and Fifth Therapeutic Methods Additional exemplary features that may characterize the First, Second, Third, Fourth, and Fifth Therapeutic Methods described herein are provided below and include, for example, the dosage of willow leaf extract, patients for treatment, and the identity of the willow leaf extract. A more thorough description of such features is provided below. The invention embraces all permutations and combinations of these features.

In certain embodiments, the method consists of orally administering to the patient in need thereof a therapeutically effective amount of the therapeutic composition comprising willow leaf extract.

In certain embodiments, the method further comprises administering to the patient in need thereof a therapeutically effective amount of an additional therapeutic agent.

In certain embodiments, the therapeutic composition consists of (i) willow leaf extract and (ii) optionally a pharmaceutically acceptable carrier.

In certain embodiments, the therapeutic composition comprises (i) willow leaf extract, (ii) an additional therapeutic agent, and (iii) optionally a pharmaceutically acceptable carrier.

Dosage of Willow Leaf Extract

The methods may be further characterized according to the dosage of willow leaf extract administered to the patient. For example, in certain embodiments, at least 2 g of willow leaf extract is orally administered to the patient per day for at least 2 days. In certain embodiments, at least 2 g of willow leaf extract is orally administered to the patient per day for at least 5 days. In certain embodiments, at least 2 g of willow leaf extract is orally administered to the patient per day for at least 7 days.

In certain embodiments, at least 3 g of willow leaf extract is orally administered to the patient per day for at least 2 days. In certain embodiments, at least 3 g of willow leaf extract is orally administered to the patient per day for at least 5 days. In certain embodiments, at least 3 g of willow leaf extract is orally administered to the patient per day for at least 7 days.

In certain embodiments, about 3 g of willow leaf extract is orally administered to the patient per day for at least 2 days. In certain embodiments, about 3 g of willow leaf extract is orally administered to the patient per day for at least 5 days. In certain embodiments, about 3 g of willow leaf extract is orally administered to the patient per day for at least 7 days. In certain embodiments, about 3 g of willow leaf extract is orally administered to the patient per day for 5 days. In certain embodiments, about 3 g of willow leaf extract is orally administered to the patient per day for 6 days. In certain embodiments, about 3 g of willow leaf extract is orally administered to the patient per day for 7 days.

In certain embodiments, from about 1 g to about 3 g of willow leaf extract is orally administered to the patient per day. In certain embodiments, from about 1 g to about 3 g of willow leaf extract is orally administered to the patient per day for at least 2 days. In certain embodiments, from about 1 g to about 3 g of willow leaf extract is orally administered to the patient per day for at least 5 days. In certain embodiments, from about 1 g to about 3 g of willow leaf extract is orally administered to the patient per day for at least 7 days. In certain embodiments, from about 1 g to about 3 g of willow leaf extract is orally administered to the patient per day for 5 days. In certain embodiments, from about 1 g to about 3 g of willow leaf extract is orally administered to the patient per day for 6 days. In certain embodiments, from about 1 g to about 3 g of willow leaf extract is orally administered to the patient per day for 7 days.

Of course, actual dosage levels of the willow leaf extract may be varied so as to obtain an amount which is effective to achieve the desired therapeutic response for a particular patient and extract, without being toxic to the patient. The selected dosage level will depend upon a variety of factors including the activity of the particular willow leaf extract of the present invention employed, the time of administration, the duration of the treatment, other drugs, compounds and/or materials used in combination with the particular willow leaf extract employed, the age, sex, weight, condition, general health and prior medical history of the patient being treated, and like factors well known in the medical arts.

A physician or veterinarian having ordinary skill in the art can readily determine and prescribe the effective amount of the willow leaf extract required. For example, the physician or veterinarian could start doses of the willow leaf extract at levels lower than that required in order to achieve the desired therapeutic effect and gradually increase the dosage until the desired effect is achieved.

Dosing Frequency of the Therapeutic Composition

The methods may be further characterized according to the frequency with which the therapeutic composition is administered to the patient. For example, in certain embodiments, a dose of the therapeutic composition is orally administered to the patient one to three times per day. In certain embodiments, a dose of the therapeutic composition is orally administered to the patient once per day. In certain embodiments, a dose of the therapeutic composition is orally administered to the patient at least once per day. In certain embodiments, a dose of the therapeutic composition is orally administered to the patient twice per day. In certain embodiments, a dose of the therapeutic composition is orally administered to the patient at least twice per day. In certain embodiments, a dose of the therapeutic composition is orally administered to the patient three times per day. In certain embodiments, a dose of the therapeutic composition is orally administered to the patient at least three times per day. In certain embodiments, a dose of the therapeutic composition is orally administered to the patient three times per day.

In certain embodiments, a dose of the therapeutic composition is orally administered to the patient at least two times per day for at least 2 days. In certain embodiments, a dose of the therapeutic composition is orally administered to the patient at least two times per day for at least 5 days. In certain embodiments, a dose of the therapeutic composition is orally administered to the patient at least two times per day for at least 7 days. In certain embodiments, a dose of the therapeutic composition is orally administered to the patient at least two times per day for 7 days In certain embodiments, a dose of the therapeutic composition is orally administered to the patient three times per day for at least 2 days. In certain embodiments, a dose of the therapeutic composition is orally administered to the patient three times per day for at least 5 days. In certain embodiments, a dose of the therapeutic composition is orally administered to the patient three times per day for at least 7 days.

In certain embodiments, a dose of the therapeutic composition is orally administered to the patient from one to three times per day for at least 2 days. In certain embodiments, a dose of the therapeutic composition is orally administered to the patient from one to three times per day for at least 5 days. In certain embodiments, a dose of the therapeutic composition is orally administered to the patient from one to three times per day for at least 7 days. In certain embodiments, a dose of the therapeutic composition is orally administered to the patient from one to three times per day for 7 to 10 days. In certain embodiments, a dose of the therapeutic composition is orally administered to the patient from one to three times per day for 7 to 14 days. In certain embodiments, a dose of the therapeutic composition is orally administered to the patient from one to three times per day for 7 days.

In certain embodiments, a dose of the therapeutic composition is orally administered to the patient three times per day for 7 to 10 days. In certain embodiments, a dose of the therapeutic composition is orally administered to the patient three times per day for 7 to 14 days. In certain embodiments, a dose of the therapeutic composition is orally administered to the patient three times per day for at least 7 days.

In certain embodiments, a dose of the therapeutic composition is orally administered at least once per day for at least 3 days each week. In certain embodiments, a dose of the therapeutic composition is orally administered at least once per day for at least 5 days each week. In certain embodiments, a dose of the therapeutic composition is orally administered at least once per day for at least 1 week. In certain embodiments, a dose of the therapeutic composition is orally administered at least once per day for at least 2 weeks. In certain embodiments, a dose of the therapeutic composition is orally administered at least once per day for at least 4, 6, 8, 10, 12, 14, 16, or 18 weeks.

In certain embodiments, a dose of the therapeutic composition is orally administered one to three times per day for at least 3 days each week. In certain embodiments, a dose of the therapeutic composition is orally administered one to three times per day for at least 5 days each week. In certain embodiments, a dose of the therapeutic composition is orally administered one to three times per day for at least 1 week. In certain embodiments, a dose of the therapeutic composition is orally administered one to three times per day for at least 2 weeks. In certain embodiments, a dose of the therapeutic composition is orally administered one to three times per day for at least 4, 6, 8, 10, 12, 14, 16, or 18 weeks.

In certain embodiments, a dose of the therapeutic composition is orally administered three times per day for at least 3 days each week. In certain embodiments, a dose of the therapeutic composition is orally administered three times per day for at least 5 days each week. In certain embodiments, a dose of the therapeutic composition is orally administered three times per day for at least 1 week. In certain embodiments, a dose of the therapeutic composition is orally administered three times per day for at least 2 weeks. In certain embodiments, a dose of the therapeutic composition is orally administered three times per day for at least 4, 6, 8, 10, 12, 14, 16, or 18 weeks.

Further, if desired, the effective daily dose of the therapeutic composition may be administered as two, three, four, five, six or more sub-doses administered separately at appropriate intervals throughout the day, optionally, in unit dosage forms. Preferred dosing is one to three administrations per day.

Amount of Willow Leaf Extract Per Dose of Therapeutic Composition

The methods may be further characterized according to the amount of willow leaf extract in each dose of the therapeutic composition. For example, in certain embodiments, the dose of therapeutic composition contains at least about 0.5 g of willow leaf extract. In certain embodiments, the dose of therapeutic composition contains at least about 0.75 g of willow leaf extract. In certain embodiments, the dose of therapeutic composition contains at least about 1 g of willow leaf extract. In certain embodiments, the dose of therapeutic composition contains from about 0.5 g to about 1.5 g of willow leaf extract. In certain embodiments, the dose of therapeutic composition contains about 1 g of willow leaf extract.

Of course, the actual amount of willow leaf extract per dose of the therapeutic compositions may be varied so as to obtain an amount of the willow leaf extract which is effective to achieve the desired therapeutic response for a particular patient, composition, and mode of administration, without being toxic to the patient. The selected dosage level will depend upon a variety of factors including the activity of the particular therapeutic composition of the present invention employed, the time of administration, the duration of the treatment, other drugs, compounds and/or materials used in combination with the particular therapeutic composition employed, the age, sex, weight, condition, general health and prior medical history of the patient being treated, and like factors well known in the medical arts.

A physician or veterinarian having ordinary skill in the art can readily determine and prescribe the effective amount of the therapeutic composition required. For example, the physician or veterinarian could start doses of the pharmaceutical composition at levels lower than that required in order to achieve the desired therapeutic effect and gradually increase the dosage until the desired effect is achieved.

Patients for Treatment

The methods may be further characterized according to patients for treatment. For example, in certain embodiments, the patient is an adult human. In certain embodiments, the patient is a pediatric human. In certain embodiments, the patient is a geriatric human.

Identity of the Willow Leaf Extract

The methods may be further characterized according to the identity of the willow leaf extract. For example, in certain embodiments, the willow leaf extract was obtained from young leaves of a willow tree. In certain embodiments, the willow leaf extract was obtained from green leaves of a willow tree. In certain embodiments, the willow leaf extract was obtained from leaves harvested from a willow tree located near standing water.

In certain embodiments, the willow leaf extract was obtained from *Salix aegyptiaca, Salix alba, Salix amygdaloides, Salix arctica, Salix babylonica, Salix bebbiana, Salix caprea, Salix cinerea, Salix discolor, Salix exigua, Salix fragilis, Salix glauca, Salix herbacea, Salix integra, Salix laevigata, Salix lasiolepis, Salix microphylla, Salix nigra, Salix paradoxa, Salix pierotii, Salix purpurea, Salix scouleriana, Salix sepulcralis* group, *Salix tetrasperma, Salix triandra, Salix viminalis*, or a combination thereof. In certain embodiments, the willow leaf extract was obtained from *Salix alba*.

In certain embodiments, the willow leaf extract was obtained from leaves harvested from a willow tree located in the Kurdistan region of Iraq. In certain embodiments, the willow leaf extract was obtained from leaves harvested from a willow tree located in the Barzan region of Iraq.

In certain embodiments, the willow leaf extract was obtained from leaves harvested from a willow tree during the month of May, June, July, August, and/or September.

In certain embodiments, the willow leaf extract is further characterized according to the identity of one or more components in the willow leaf extract. In certain embodiments, the willow leaf extract comprises salicin (which has the chemical name (2R,3S,4S,5R,6S)-2-(hydroxymethyl)-6-[2-(hydroxymethyl)phenoxy]oxane-3,4,5-triol). In certain embodiments, the willow leaf extract comprises salicin in an amount of at least 0.0001% w/w, 0.001% w/w, 0.01% w/w, 0.1% w/w, or 1% w/w of the willow leaf extract. In certain embodiments, the willow leaf extract comprises salicin in an amount of at least 1%, 2%, 3%, 4%, 5%, 6%, 7%, 8%, 9%, or 10% w/w of the willow leaf extract. In certain embodiments, the willow leaf extract comprises salicin in an amount of from about 0.0001% w/w to about 0.001% w/w, about 0.001% w/w to about 0.01% w/w, about 0.01% w/w to about 0.1% w/w, or about 0.1% to about 1% w/w of the willow leaf extract. In certain embodiments, the willow leaf extract comprises salicin in an amount of from about 1% w/w to about 2% w/w, about 1% w/w to 3% w/w, about 1% w/w to about 4% w/w, about 1% w/w to about 5% w/w, about 1% w/w to about 6% w/w, about 1% w/w to about 7% w/w, about 1% to about 8% w/w, about 1% to about 9% w/w, or about 1% to about 10% w/w of the willow leaf extract. In certain embodiments, the willow leaf extract comprises salicin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, about 5% to about 8% w/w, about 5% w/w to about 9% w/w, or about 5% w/w to about 10% w/w of the willow leaf extract. In certain embodiments, the willow leaf extract comprises salicin in an amount of from about 6% w/w to about 9% w/w, about 6% w/w to about 10% w/w, about 6% w/w to about 11% w/w, about 7% w/w to about 10% w/w, about 7% w/w to about 11% w/w, about 7% w/w to about 12% w/w, about 8% w/w to about 11% w/w, about 8% w/w to about 12% w/w, about 8% w/w to about 13% w/w, about 9% w/w to about 11% w/w, about 9% w/w to about 12% w/w, about 9% w/w to about 13% w/w, about 9% w/w to about 14% w/w, about 10% w/w to about 13% w/w, about 10% w/w to about 14% w/w, about 10% w/w to about 15% w/w, about 11% w/w to about 14% w/w, about 11% w/w to about 15% w/w, about 11% w/w to about 16% w/w, about 12% w/w to about 15% w/w, about 12% w/w to about 16% w/w, about 12% w/w to about 17% w/w, about 13% w/w to about 16% w/w, about 13% w/w to about 17% w/w, about 13% w/w to about 18% w/w, about 14% w/w to about 17% w/w, about 14% w/w to about 18% w/w, about 14% w/w to about 19% w/w, about 15% w/w to about 20% w/w, or about 15% w/w to about 21% w/w of the willow leaf extract. In certain embodiments, the willow leaf extract comprises salicin in an amount of about 5%. In certain embodiments, the willow leaf extract comprises salicin in an amount of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% w/w of the willow leaf extract. In certain embodiments, the willow leaf extract comprises less than 10% w/w, 9% w/w, 8% w/w, 7% w/w, 6% w/w, 5% w/w, 4% w/w, 3% w/w, 2% w/w, 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of salicin. In certain embodiments, the willow leaf extract does not contain salicin. Salicin has anti-inflammatory activity.

In certain embodiments, the willow leaf extract comprises salicylic acid (which has the chemical name (2-hydroxybenzoic acid). In certain embodiments, the willow leaf extract comprises salicylic acid in an amount of at least 0.0001% w/w, 0.001% w/w, 0.01% w/w, 0.1% w/w, or 1% w/w of the willow leaf extract. In certain embodiments, the willow leaf extract comprises salicylic acid in an amount of from about 0.0001% w/w to about 0.001% w/w, about 0.001% w/w to about 0.01% w/w, about 0.01% w/w to about 0.1% w/w, or about 0.1% to about 1% w/w of the willow leaf extract. In certain embodiments, the willow leaf extract comprises less than 8% w/w, 7% w/w, 6% w/w, 5% w/w, 4% w/w, 3% w/w, 2% w/w, 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of salicylic acid. In certain embodiments, the willow leaf extract does not contain salicylic acid.

In certain embodiments, the willow leaf extract comprises salicortin. In certain embodiments, the willow leaf extract comprises salicortin in an amount of at least 0.0001% w/w, 0.001% w/w, 0.01% w/w, 0.1% w/w, or 1% w/w of the willow leaf extract. In certain embodiments, the willow leaf extract comprises salicortin in an amount of at least 1%, 2%, 3%, 4%, 5%, 6%, 7%, 8%, 9%, or 10% w/w of the willow leaf extract. In certain embodiments, the willow leaf extract comprises salicortin in an amount of from about 0.0001% w/w to about 0.001% w/w, about 0.001% w/w to about 0.01% w/w, about 0.01% w/w to about 0.1% w/w, or about 0.1% to about 1% w/w of the willow leaf extract. In certain embodiments, the willow leaf extract comprises salicortin in an amount of from about 1% w/w to about 2% w/w, about 1% w/w to 3% w/w, about 1% w/w to about 4% w/w, about 1% w/w to about 5% w/w, about 1% w/w to about 6% w/w, about 1% w/w to about 7% w/w, about 1% to about 8% w/w, about 1% to about 9% w/w, or about 1% to about 10% w/w of the willow leaf extract. In certain embodiments, the willow leaf extract comprises salicortin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% to about 6% w/w, about 4% to about 7% w/w, or about 5% to about 8% w/w of the willow leaf extract. In certain embodiments, the willow leaf extract comprises less than 8% w/w, 7% w/w, 6% w/w, 5% w/w, 4% w/w, 3% w/w, 2% w/w, 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of salicortin. In certain embodiments, the willow leaf extract does not contain salicortin.

In certain embodiments, the willow leaf extract comprises 2'-O-acetylsalicortin. In certain embodiments, the willow leaf extract comprises 2'-O-acetylsalicortin in an amount of at least 0.0001% w/w, 0.001% w/w, 0.01% w/w, 0.1% w/w, or 1% w/w of the willow leaf extract. In certain embodiments, the willow leaf extract comprises 2'-O-acetylsalicortin in an amount of at least 1%, 2%, 3%, 4%, 5%, 6%, 7%, 8%, 9%, 10%, 11%, 12%, 13%, 14%, or 15% w/w of the willow leaf extract. In certain embodiments, the willow leaf extract comprises 2'-O-acetylsalicortin in an amount of from about 0.0001% w/w to about 0.001% w/w, about 0.001% w/w to about 0.01% w/w, about 0.01% w/w to about 0.1% w/w, or about 0.1% to about 1% w/w of the willow leaf extract. In certain embodiments, the willow leaf extract comprises 2'-O-acetylsalicortin in an amount of from about 1% w/w to about 2% w/w, about 1% w/w to 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow leaf extract. In certain embodiments, the willow leaf extract comprises 2'-O-acetylsalicortin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, about 5% w/w to about 8% w/w, about 5% w/w to about 9% w/w, about 5% w/w to about 10% w/w, about 7% w/w to about 9% w/w, about 7% w/w to about 10% w/w, about 7% w/w to about 11% w/w, about 9% w/w to about 12% w/w, about 8% w/w to about 10% w/w, about 8% w/w to about 11% w/w, about 8% w/w to about 12% w/w, about 8% w/w to about 13% w/w, about 9% w/w to about 11% w/w, about 9% w/w to about 12% w/w, or about 9% w/w to about 13% w/w. In certain embodiments, the willow leaf extract comprises less than 10% w/w, 9% w/w, 8% w/w, 7% w/w, 6% w/w, 5% w/w, 4% w/w, 3% w/w, 2% w/w, 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of 2'-O-acetylsalicortin. In certain embodiments, the willow leaf extract does not contain 2'-O-acetylsalicortin.

In certain embodiments, the willow leaf extract comprises tremulacin. In certain embodiments, the willow leaf extract comprises tremulacin in an amount of at least 0.0001% w/w, 0.001% w/w, 0.01% w/w, 0.1% w/w, or 1% w/w of the willow leaf extract. In certain embodiments, the willow leaf extract comprises tremulacin in an amount of at least 1%, 2%, 3%, 4%, 5%, or 6% w/w of the willow leaf extract. In certain embodiments, the willow leaf extract comprises tremulacin in an amount of from about 0.0001% w/w to about 0.001% w/w, about 0.001% w/w to about 0.01% w/w, about 0.01% w/w to about 0.1% w/w, or about 0.1% to about 1% w/w of the willow leaf extract. In certain embodiments, the willow leaf extract comprises tremulacin in an amount of from about 0.5% w/w to about 1% w/w, about 0.5% w/w to about 2% w/w, about 1% w/w to about 2% w/w, about 1% w/w to about 3% w/w, about 1% w/w to about 4% w/w, about 2% w/w to about 3% w/w, about 2% to about 3% w/w, about 2% to about 4% w/w, or about 2% to about 5% w/w of the willow leaf extract. In certain embodiments, the willow leaf extract comprises tremulacin in an amount of from about 0.5% w/w to about 1% w/w, about 0.5% w/w to about 2% w/w, about 1% w/w to about 2% w/w, about 1% w/w to about 3% w/w, about 1% w/w to about 4% w/w, about 2% w/w to about 3% w/w, about 2% to about 4% w/w, about 2% to about 5% w/w, or about 3% to about 5% w/w of the willow leaf extract. In certain embodiments, the willow leaf extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of tremulacin. In certain embodiments, the willow leaf extract does not contain tremulacin.

In certain embodiments, the willow leaf extract comprises picein. In certain embodiments, the willow leaf extract comprises picein in an amount of at least 0.0001% w/w, 0.001% w/w, 0.01% w/w, 0.1% w/w, or 1% w/w of the willow leaf extract. In certain embodiments, the willow leaf extract comprises picein in an amount of from about 0.0001% w/w to about 0.001% w/w, about 0.001% w/w to about 0.01% w/w, about 0.01% w/w to about 0.1% w/w, or about 0.1% to about 1% w/w of the willow leaf extract. In certain embodiments, the willow leaf extract comprises picein in an amount of from about 0.001% w/w to about 0.01% w/w of the willow leaf extract. In certain embodiments, the willow leaf extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of picein. In certain embodiments, the willow leaf extract does not contain picein.

In certain embodiments, the willow leaf extract comprises catechin. In certain embodiments, the willow leaf extract comprises catechin in an amount of at least 0.0001% w/w, 0.001% w/w, 0.01% w/w, 0.1% w/w, or 1% w/w of the willow leaf extract. In certain embodiments, the willow leaf extract comprises catechin in an amount of from about 0.0001% w/w to about 0.001% w/w, about 0.001% w/w to about 0.01% w/w, about 0.01% w/w to about 0.1% w/w, or about 0.1% to about 1% w/w of the willow leaf extract. In certain embodiments, the willow leaf extract comprises catechin in an amount of from about 0.01% w/w to about 0.1% w/w of the willow leaf extract. In certain embodiments, the willow leaf extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of catechin. In certain embodiments, the willow leaf extract does not contain catechin.

In certain embodiments, the willow leaf extract comprises p-coumaric acid. In certain embodiments, the willow leaf extract comprises p-coumaric acid in an amount of at least 0.0001% w/w, 0.001% w/w, 0.01% w/w, 0.1% w/w, or 1% w/w of the willow leaf extract. In certain embodiments, the willow leaf extract comprises p-coumaric acid in an amount of from about 0.0001% w/w to about 0.001% w/w, about 0.001% w/w to about 0.01% w/w, about 0.01% w/w to about 0.1% w/w, or about 0.1% to about 1% w/w of the willow leaf extract. In certain embodiments, the willow leaf extract comprises p-coumaric acid in an amount of from about 0.01% w/w to about 0.1% w/w of the willow leaf extract. In certain embodiments, the willow leaf extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of p-coumaric acid. In certain embodiments, the willow leaf extract does not contain p-coumaric acid In certain embodiments, the willow leaf extract comprises saligenin. In certain embodiments, the willow leaf extract comprises saligenin in an amount of at least 0.0001% w/w, 0.001% w/w, 0.01% w/w, 0.1% w/w, or 1% w/w of the willow leaf extract. In certain embodiments, the willow leaf extract comprises saligenin in an amount of at least 1%, 2%, 3%, 4%, 5%, 6%, 7%, 8%, 9%, or 10% w/w of the willow leaf extract. In certain embodiments, the willow leaf extract comprises saligenin in an amount of from about 0.0001% w/w to about 0.001% w/w, about 0.001% w/w to about 0.01% w/w, about 0.01% w/w to about 0.1% w/w, about 0.1% to about 0.5% w/w, or about 0.1% to about 1% w/w of the willow leaf extract. In certain embodiments, the willow leaf extract comprises saligenin in an amount of from about 1% w/w to about 2% w/w, about 1% w/w to 3% w/w, about 1% w/w to about 4% w/w, about 1% w/w to about 5% w/w, about 1% w/w to about 6% w/w, about 1% w/w to about 7% w/w, about 1% to about 8% w/w, about 1% to about 9% w/w, or about 1% to about 10% w/w of the willow leaf extract. In certain embodiments, the willow leaf extract comprises saligenin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% to about 6% w/w, about 4% to about 7% w/w, or about 5% to about 8% w/w of the willow leaf extract. In certain embodiments, the willow leaf extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of saligenin. In certain embodiments, the willow leaf extract does not contain saligenin.

In certain embodiments, the willow leaf extract comprises salidroside. In certain embodiments, the willow leaf extract comprises salidroside in an amount of at least 0.0001% w/w, 0.001% w/w, 0.01% w/w, 0.1% w/w, or 1% w/w of the willow leaf extract. In certain embodiments, the willow leaf extract comprises salidroside in an amount of at least 1%, 2%, 3%, 4%, 5%, 6%, 7%, 8%, 9%, or 10% w/w of the willow leaf extract. In certain embodiments, the willow leaf extract comprises salidroside in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow leaf extract. In certain embodiments, the willow leaf extract comprises salidroside in an amount of from about 1% w/w to about 2% w/w, about 1% w/w to 3% w/w, about 1% w/w to about 4% w/w, about 1% w/w to about 5% w/w, about 1% w/w to about 6% w/w, about 1% w/w to about 7% w/w, about 1% to about 8% w/w, about 1% to about 9% w/w, or about 1% to about 10% w/w of the willow leaf extract. In certain embodiments, the willow leaf extract comprises salidroside in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow leaf extract. In certain embodiments, the willow leaf extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of salidroside. In certain embodiments, the willow leaf extract does not contain salidroside.

In certain embodiments, the willow leaf extract comprises triandrin. In certain embodiments, the willow leaf extract comprises triandrin in an amount of at least 0.0001% w/w, 0.001% w/w, 0.01% w/w, 0.1% w/w, or 1% w/w of the willow leaf extract. In certain embodiments, the willow leaf extract comprises triandrin in an amount of at least 1%, 2%, 3%, 4%, 5%, 6%, 7%, 8%, 9%, or 10% w/w of the willow leaf extract. In certain embodiments, the willow leaf extract comprises triandrin in an amount of from about 0.0001% w/w to about 0.001% w/w, about 0.001% w/w to about 0.01% w/w, about 0.01% w/w to about 0.1% w/w, about 0.1% to about 0.5% w/w, or about 0.1% to about 1% w/w of the willow leaf extract. In certain embodiments, the willow leaf extract comprises triandrin in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% to about 8% w/w, about 1% to about 9% w/w, or about 1% to about 10% w/w of the willow leaf extract. In certain embodiments, the willow leaf extract comprises triandrin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% to about 6% w/w, about 4% to about 7% w/w, or about 5% to about 8% w/w of the willow leaf extract. In certain embodiments, the willow leaf extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, 0.00001% w/w of triandrin. In certain embodiments, the willow leaf extract does not contain triandrin.

In certain embodiments, the willow leaf extract comprises isosalipurposide. In certain embodiments, the willow leaf extract comprises isosalipurposide in an amount of at least 0.0001% w/w, 0.001% w/w, 0.01% w/w, 0.1% w/w, or 1% w/w of the willow leaf extract. In certain embodiments, the willow leaf extract comprises isosalipurposide in an amount of at least 1%, 2%, 3%, 4%, 5%, 6%, 7%, 8%, 9%, or 10% w/w of the willow leaf extract. In certain embodiments, the willow leaf extract comprises isosalipurposide in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow leaf extract. In certain embodiments, the willow leaf extract comprises isosalipurposide in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% to about 10% w/w of the willow leaf extract. In certain embodiments, the willow leaf extract comprises isosalipurposide in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% to about 6% w/w, about 4% to about 7% w/w, or about 5% to about 8% w/w of the willow leaf extract. In certain embodiments, the willow leaf extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of isosalipurposide. In certain embodiments, the willow leaf extract does not contain isosalipurposide In certain embodiments, the willow leaf extract comprises naringenin-7-O-glucoside. In certain embodiments, the willow leaf extract comprises naringenin-7-O-glucoside in an amount of at least 0.0001% w/w, 0.001% w/w, 0.01% w/w, 0.1% w/w, or 1% w/w of the willow leaf extract. In certain embodiments, the willow leaf extract comprises naringenin-7-O-glucoside in an amount of at least 1%, 2%, 3%, 4%, 5%, 6%, 7%, 8%, 9%, or 10% w/w of the willow leaf extract. In certain embodiments, the willow leaf extract comprises naringenin-7-O-glucoside in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow leaf extract. In certain embodiments, the willow leaf extract comprises naringenin-7-O-glucoside in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% to about 8% w/w, about 1% to about 9% w/w, or about 1% to about 10% w/w of the willow leaf extract. In certain embodiments, the willow leaf extract comprises naringenin-7-O-glucoside in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow leaf extract. In certain embodiments, the willow leaf extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of naringenin-7-O-glucoside. In certain embodiments, the willow leaf extract does not contain naringenin-7-O-glucoside.

In certain embodiments, the willow leaf extract comprises prunin. In certain embodiments, the willow leaf extract comprises prunin in an amount of at least 0.0001% w/w, 0.001% w/w, 0.01% w/w, 0.1% w/w, or 1% w/w of the willow leaf extract. In certain embodiments, the willow leaf extract comprises prunin in an amount of at least 1%, 2%, 3%, 4%, 5%, 6%, 7%, 8%, 9%, or 10% w/w of the willow leaf extract. In certain embodiments, the willow leaf extract comprises prunin in an amount of from about 0.0001% w/w to about 0.001% w/w, about 0.001% w/w to about 0.01% w/w, about 0.01% w/w to about 0.1% w/w, about 0.1% to about 0.5% w/w, or about 0.1% w/w to about 1% w/w of the willow leaf extract. In certain embodiments, the willow leaf extract comprises prunin in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow leaf extract. In certain embodiments, the willow leaf extract comprises prunin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow leaf extract. In certain embodiments, the willow leaf extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of prunin. In certain embodiments, the willow leaf extract does not contain prunin.

In certain embodiments, the willow leaf extract comprises ampelopsin. In certain embodiments, the willow leaf extract comprises ampelopsin in an amount of at least 0.0001% w/w, 0.001% w/w, 0.01% w/w, 0.1% w/w, or 1% w/w of the willow leaf extract. In certain embodiments, the willow leaf extract comprises ampelopsin in an amount of at least 1%, 2%, 3%, 4%, 5%, 6%, 7%, 8%, 9%, or 10% w/w of the willow leaf extract. In certain embodiments, the willow leaf extract comprises ampelopsin in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow leaf extract. In certain embodiments, the willow leaf extract comprises ampelopsin in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow leaf extract. In certain embodiments, the willow leaf extract comprises ampelopsin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow leaf extract. In certain embodiments, the willow leaf extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of ampelopsin. In certain embodiments, the willow leaf extract does not contain ampelopsin.

In certain embodiments, the willow leaf extract comprises benzoic acid. In certain embodiments, the willow leaf extract comprises benzoic acid in an amount of at least 0.0001% w/w, 0.001% w/w, 0.01% w/w, 0.1% w/w, or 1% w/w of the willow leaf extract. In certain embodiments, the willow leaf extract comprises benzoic acid in an amount of at least 1%, 2%, 3%, 4%, 5%, 6%, 7%, 8%, 9%, or 10% w/w of the willow leaf extract. In certain embodiments, the willow leaf extract comprises benzoic acid in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow leaf extract. In certain embodiments, the willow leaf extract comprises benzoic acid in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow leaf extract. In certain embodiments, the willow leaf extract comprises benzoic acid in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow leaf extract. In certain embodiments, the willow leaf extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of benzoic acid. In certain embodiments, the willow leaf extract does not contain benzoic acid.

In certain embodiments, the willow leaf extract comprises populin. In certain embodiments, the willow leaf extract comprises populin in an amount of at least 0.0001% w/w, 0.001% w/w, 0.01% w/w, 0.1% w/w, or 1% w/w of the willow leaf extract. In certain embodiments, the willow leaf extract comprises populin in an amount of at least 1%, 2%, 3%, 4%, 5%, 6%, 7%, 8%, 9%, or 10% w/w of the willow leaf extract. In certain embodiments, the willow leaf extract comprises populin in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow leaf extract. In certain embodiments, the willow leaf extract comprises populin in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow leaf extract. In certain embodiments, the willow leaf extract comprises populin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow leaf extract. In certain embodiments, the willow leaf extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of populin. In certain embodiments, the willow leaf extract does not contain populin.

In certain embodiments, the willow leaf extract comprises syringin. In certain embodiments, the willow leaf extract comprises syringin in an amount of at least 0.0001% w/w, 0.001% w/w, 0.01% w/w, 0.1% w/w, or 1% w/w of the willow leaf extract. In certain embodiments, the willow leaf extract comprises syringin in an amount of at least 1%, 2%, 3%, 4%, 5%, 6%, 7%, 8%, 9%, or 10% w/w of the willow leaf extract. In certain embodiments, the willow leaf extract comprises syringin in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow leaf extract. In certain embodiments, the willow leaf extract comprises syringin in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow leaf extract. In certain embodiments, the willow leaf extract comprises syringin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow leaf extract. In certain embodiments, the willow leaf extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of syringin. In certain embodiments, the willow leaf extract does not contain syringin.

In certain embodiments, the willow leaf extract comprises salireposide. In certain embodiments, the willow leaf extract comprises salireposide in an amount of at least 0.0001% w/w, 0.001% w/w, 0.01% w/w, 0.1% w/w, or 1% w/w of the willow leaf extract. In certain embodiments, the willow leaf extract comprises salireposide in an amount of at least 1%, 2%, 3%, 4%, 5%, 6%, 7%, 8%, 9%, or 10% w/w of the willow leaf extract. In certain embodiments, the willow leaf extract comprises salireposide in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow leaf extract. In certain embodiments, the willow leaf extract comprises salireposide in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow leaf extract. In certain embodiments, the willow leaf extract comprises salireposide in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow leaf extract. In certain embodiments, the willow leaf extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of salireposide. In certain embodiments, the willow leaf extract does not contain salireposide.

In certain embodiments, the willow extract comprises 2'-O-acetylsalicin. In certain embodiments, the willow extract comprises 2'-O-acetylsalicin in an amount of at least 0.0001% w/w, 0.001% w/w, 0.01% w/w, 0.1% w/w, or 1% w/w of the willow extract. In certain embodiments, the willow extract comprises 2'-O-acetylsalicin in an amount of at least 1%, 2%, 3%, 4%, 5%, 6%, 7%, 8%, 9%, 10%, 11%, 12%, 13%, 14%, or 15% w/w of the willow extract. In certain embodiments, the willow extract comprises 2'-O-acetylsalicin in an amount of from about 0.0001% w/w to about 0.001% w/w, about 0.001% w/w to about 0.01% w/w, about 0.01% w/w to about 0.1% w/w, or about 0.1% to about 1% w/w of the willow extract. In certain embodiments, the willow extract comprises 2'-O-acetylsalicin in an amount of from about 1% w/w to about 2% w/w, about 1% w/w to 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow extract. In certain embodiments, the willow extract comprises 2'-O-acetylsalicin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, about 5% w/w to about 8% w/w, about 5% w/w to about 9% w/w, about 5% w/w to about 10% w/w, about 7% w/w to about 9% w/w, about 7% w/w to about 10% w/w, about 7% w/w to about 11% w/w, about 9% w/w to about 12% w/w, about 8% w/w to about 10% w/w, about 8% w/w to about 11% w/w, about 8% w/w to about 12% w/w, about 8% w/w to about 13% w/w, about 9% w/w to about 11% w/w, about 9% w/w to about 12% w/w, or about 9% w/w to about 13% w/w. In certain embodiments, the willow extract comprises less than 10% w/w, 9% w/w, 8% w/w, 7% w/w, 6% w/w, 5% w/w, 4% w/w, 3% w/w, 2% w/w, 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of 2'-O-acetylsalicin. In certain embodiments, the willow extract does not contain 2'-O-acetylsalicin.

In certain embodiments, the willow extract comprises 6'-O-acetylsalicin. In certain embodiments, the willow extract comprises 6'-O-acetylsalicin in an amount of at least 0.0001% w/w, 0.001% w/w, 0.01% w/w, 0.1% w/w, or 1% w/w of the willow extract. In certain embodiments, the willow extract comprises 6'-O-acetylsalicin in an amount of at least 1%, 2%, 3%, 4%, 5%, 6%, 7%, 8%, 9%, 10%, 11%, 12%, 13%, 14%, or 15% w/w of the willow extract. In certain embodiments, the willow extract comprises 6'-O-acetylsalicin in an amount of from about 0.0001% w/w to about 0.001% w/w, about 0.001% w/w to about 0.01% w/w, about 0.01% w/w to about 0.1% w/w, or about 0.1% to about 1% w/w of the willow extract. In certain embodiments, the willow extract comprises 6'-O-acetylsalicin in an amount of from about 1% w/w to about 2% w/w, about 1% w/w to 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow extract. In certain embodiments, the willow extract comprises 6'-O-acetylsalicin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, about 5% w/w to about 8% w/w, about 5% w/w to about 9% w/w, about 5% w/w to about 10% w/w, about 7% w/w to about 9% w/w, about 7% w/w to about 10% w/w, about 7% w/w to about 11% w/w, about 9% w/w to about 12% w/w, about 8% w/w to about 10% w/w, about 8% w/w to about 11% w/w, about 8% w/w to about 12% w/w, about 8% w/w to about 13% w/w, about 9% w/w to about 11% w/w, about 9% w/w to about 12% w/w, or about 9% w/w to about 13% w/w. In certain embodiments, the willow extract comprises less than 10% w/w, 9% w/w, 8% w/w, 7% w/w, 6% w/w, 5% w/w, 4% w/w, 3% w/w, 2% w/w, 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of 6'-O-acetylsalicin. In certain embodiments, the willow extract does not contain 6'-O-acetylsalicin.

In certain embodiments, the willow leaf extract comprises vimalin. In certain embodiments, the willow leaf extract comprises vimalin in an amount of at least 0.0001% w/w, 0.001% w/w, 0.01% w/w, 0.1% w/w, or 1% w/w of the willow leaf extract. In certain embodiments, the willow leaf extract comprises vimalin in an amount of at least 1%, 2%, 3%, 4%, 5%, 6%, 7%, 8%, 9%, or 10% w/w of the willow leaf extract. In certain embodiments, the willow leaf extract comprises vimalin in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow leaf extract. In certain embodiments, the willow leaf extract comprises vimalin in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow leaf extract. In certain embodiments, the willow leaf extract comprises vimalin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow leaf extract. In certain embodiments, the willow leaf extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of vimalin. In certain embodiments, the willow leaf extract does not contain vimalin.

In certain embodiments, the willow leaf extract comprises grandidentatin. In certain embodiments, the willow leaf extract comprises grandidentatin in an amount of at least 0.0001% w/w, 0.001% w/w, 0.01% w/w, 0.1% w/w, or 1% w/w of the willow leaf extract. In certain embodiments, the willow leaf extract comprises grandidentatin in an amount of at least 1%, 2%, 3%, 4%, 5%, 6%, 7%, 8%, 9%, or 10% w/w of the willow leaf extract. In certain embodiments, the willow leaf extract comprises grandidentatin in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow leaf extract. In certain embodiments, the willow leaf extract comprises grandidentatin in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow leaf extract. In certain embodiments, the willow leaf extract comprises grandidentatin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow leaf extract. In certain embodiments, the willow leaf extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of grandidentatin.

In certain embodiments, the willow leaf extract comprises tremuloidin. In certain embodiments, the willow leaf extract comprises tremuloidin in an amount of at least 0.0001% w/w, 0.001% w/w, 0.01% w/w, 0.1% w/w, or 1% w/w of the willow leaf extract. In certain embodiments, the willow leaf extract comprises tremuloidin in an amount of at least 1%, 2%, 3%, 4%, 5%, 6%, 7%, 8%, 9%, or 10% w/w of the willow leaf extract. In certain embodiments, the willow leaf extract comprises tremuloidin in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow leaf extract. In certain embodiments, the willow leaf extract comprises tremuloidin in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow leaf extract. In certain embodiments, the willow leaf extract comprises tremuloidin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow leaf extract. In certain embodiments, the willow leaf extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of tremuloidin. In certain embodiments, the willow leaf extract does not contain tremuloidin.

In certain embodiments, the willow leaf extract comprises fragilin. In certain embodiments, the willow leaf extract comprises fragilin in an amount of at least 0.0001% w/w, 0.001% w/w, 0.01% w/w, 0.1% w/w, or 1% w/w of the willow leaf extract. In certain embodiments, the willow leaf extract comprises fragilin in an amount of from about 0.0001% w/w to about 0.001% w/w, about 0.001% w/w to about 0.01% w/w, about 0.01% w/w to about 0.1% w/w, or about 0.1% to about 1% w/w of the willow leaf extract. In certain embodiments, the willow leaf extract comprises less than 2% w/w, 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of fragilin. In certain embodiments, the willow leaf extract does not contain fragilin.

The willow leaf extract may be further characterized according to the chromatogram that results from analytical chromatography of the willow leaf extract. For example, in certain embodiments, the willow leaf extract when subjected to ultra performance liquid chromatography (UPLC) provides a chromatogram comprising peaks at retention times of about 4.33 minutes, about 5.40 minutes, about 7.90 minutes, about 11.96 minutes, and about 21.14 minutes using a diode array detector at 270 nm; wherein the chromatogram is obtained by UPLC on a test sample prepared by the following procedure: an aliquot of powdered willow leaf extract is treated with boiling water (about 1 mL/10 mg willow leaf extract) at a temperature of about 100° C. for about 15 minutes, and then the resulting mixture is cooled, then filtered through a filter of about 0.1 µm to about 0.5 µm to provide the test sample; and wherein the chromatographic method is:

| Column | Waters Acquity UPLC BEH C18 1.7 µm, 2.1 × 50 mm |
|---|---|
| Mobile Phase A | 0.1% Formic Acid in Water |
| Mobile Phase B | Acetonitrile |
| Gradient Method | 5-30% B over 20 min, 30-95% B in 1 min, hold 95% B for 2 min, 95-5% B in 0.1 min, hold 5% B for 1.9 min. |
| Flow Rate | 0.3 mL/min |
| Column Temperature | 40° C. |
| Sample Diluent | Water or Methanol. |

In certain embodiments, the analytical UPLC chromatogram of the willow leaf extract further comprises peaks at one or more of the following retention times of about 1.46 minutes, about 5.15 minutes, about 6.28 minutes, about 8.07 minutes, about 13.68 minutes, and about 15.07 minutes. In certain embodiments, the analytical UPLC chromatogram of the willow leaf extract further comprises peaks at retention times of about 1.46 minutes, about 5.15 minutes, about 6.28 minutes, about 8.07 minutes, about 13.68 minutes, and about 15.07 minutes. In certain embodiments, the analytical UPLC chromatogram of the willow leaf extract further comprises peaks at retention times of about 1.29 minutes, about 1.95 minutes, about 4.01 minutes, about 5.88 minutes, about 9.16 minutes, about 9.88 minutes, about 11.62 minutes, about 12.35 minutes, about 13.02 minutes, about 16.18 minutes, about 17.39 minutes, and about 22.94 minutes. In certain embodiments, the analytical UPLC chromatogram of the willow leaf extract further comprises peaks at one or more of the following retention times of about 1.29 minutes, about 1.95 minutes, about 4.01 minutes, about 5.88 minutes, about 9.16 minutes, about 9.88 minutes, about 11.62 minutes, about 12.35 minutes, about 13.02 minutes, about 16.18 minutes, about 17.39 minutes, and about 22.94 minutes.

In certain embodiments, each of the peaks has an intensity of at least 20% relative to the peak at retention time of about 4.33 minutes. In certain embodiments, each of the peaks has an intensity of at least 10% relative to the peak at retention time of about 4.33 minutes. In certain embodiments, each of the peaks has an intensity of at least 5% relative to the peak at retention time of about 4.33 minutes.

Figure 4:
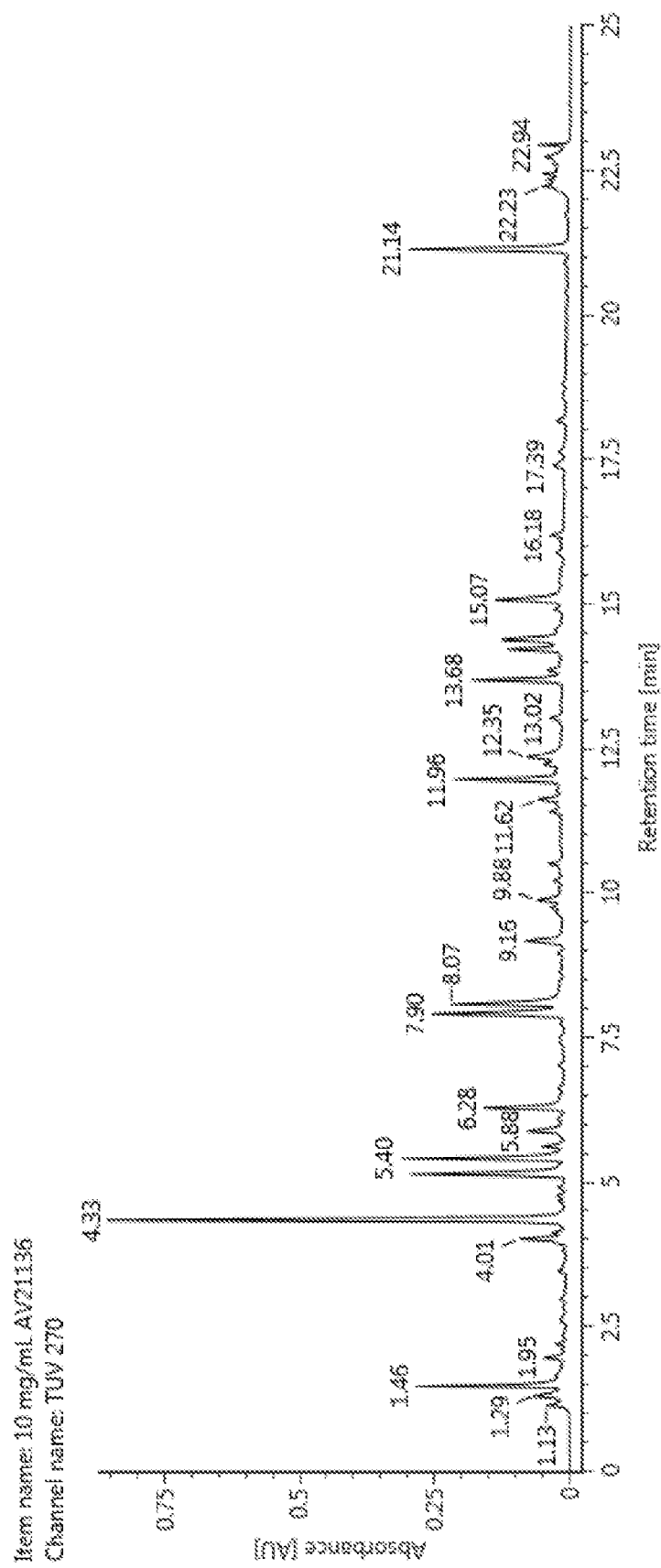
FIG. 4 depicts results of UPLC of a willow leaf extract varying the extraction conditions and chromatographic conditions, as described in Example 3.

In certain embodiments, an analytical ultra performance liquid chromatography (UPLC) chromatogram of the willow leaf extract is substantially as shown in FIG. 4 using a diode array detector at 270 nm; wherein the chromatogram is obtained by UPLC on a test sample prepared by the following procedure: an aliquot of powdered willow leaf extract is treated with boiling water (about 1 mL/10 mg willow leaf extract) at a temperature of about 100° C. for about 15 minutes, and then the resulting mixture is cooled, then filtered through a filter of about 0.1 µm to about 0.5 µm to provide the test sample; and wherein the chromatographic method is:

| Column | Waters Acquity UPLC BEH C18 1.7 µm, 2.1 × 50 mm |
|---|---|
| Mobile Phase A | 0.1% Formic Acid in Water |
| Mobile Phase B | Acetonitrile |
| Gradient Method | 5-30% B over 20 min, 30-95% B in 1 min, hold 95% B for 2 min, 95-5% B in 0.1 min, hold 5% B for 1.9 min. |
| Flow Rate | 0.3 mL/min |
| Column Temperature | 40° C. |
| Sample Diluent | Water or Methanol. |

In certain embodiments, a preparative-scale high performance liquid chromatography (HPLC) chromatogram of the willow leaf extract comprises peaks at retention times of about 1.33 minutes, about 2.77 minutes, about 2.91 minutes, about 3.08 minutes, about 5.74 minutes, about 6.29 minutes, and about 8.53 minutes using a diode array detector at 270 nm; wherein the chromatogram is obtained on a test sample prepared by the following procedure: an aliquot of powdered willow leaf extract is treated with boiling water (about 1 mL/10 mg willow leaf extract) at a temperature of about 100° C. for about 15 minutes, and then the resulting mixture is cooled, then filtered through a filter of about 0.1 µm to about 0.5 µm to provide the test sample; and wherein the chromatographic method is:

| Column | XBridge Prep C18 19 × 100 mm |
|---|---|
| Mobile Phase A | Water with 100 mM Ammonium Acetate, pH 5.3 |
| Mobile Phase B | Acetonitrile |
| Gradient Method | Initial at 5% B, hold at 5% B for 0.5 minute, 5-35% B over 7.4 minutes, 35-95% B over 0.1 minute, hold at 95% B for 1 minute and return to initial conditions |
| Column Temperature | 25° C. |
| Sample Diluent | Methanol. |

In certain embodiments, the preparative-scale HPLC chromatogram of the willow leaf extract further comprises peaks at one or more of the following retention times of about 1.01 minutes, about 1.59 minutes, about 3.48 minutes, about 3.91 minutes, and about 5.47 minutes. In certain embodiments, the preparative-scale HPLC chromatogram of the willow leaf extract further comprises peaks at retention times of about 1.01 minutes, about 1.59 minutes, about 3.48 minutes, about 3.91 minutes, and about 5.47 minutes. In certain embodiments, the preparative-scale HPLC chromatogram of the willow leaf extract further comprises peaks at one or more of the following retention times of about 2.21 minutes, 4.84 minutes, 5.37 minutes, about 6.88 minutes, about 7.62 minutes, and about 8.97 minutes. In certain embodiments, the preparative-scale HPLC chromatogram of the willow leaf extract further comprises peaks at retention times of about 2.21 minutes, 4.84 minutes, 5.37 minutes, about 6.88 minutes, about 7.62 minutes, and about 8.97 minutes.

In certain embodiments, each of the peaks has an intensity of at least 20% relative to the peak at retention time of about 3.08 minutes. In certain embodiments, each of the peaks has an intensity of at least 10% relative to the peak at retention time of about 3.08 minutes. In certain embodiments, each of the peaks has an intensity of at least 5% relative to the peak at retention time of about 3.08 minutes.

Figure 7:
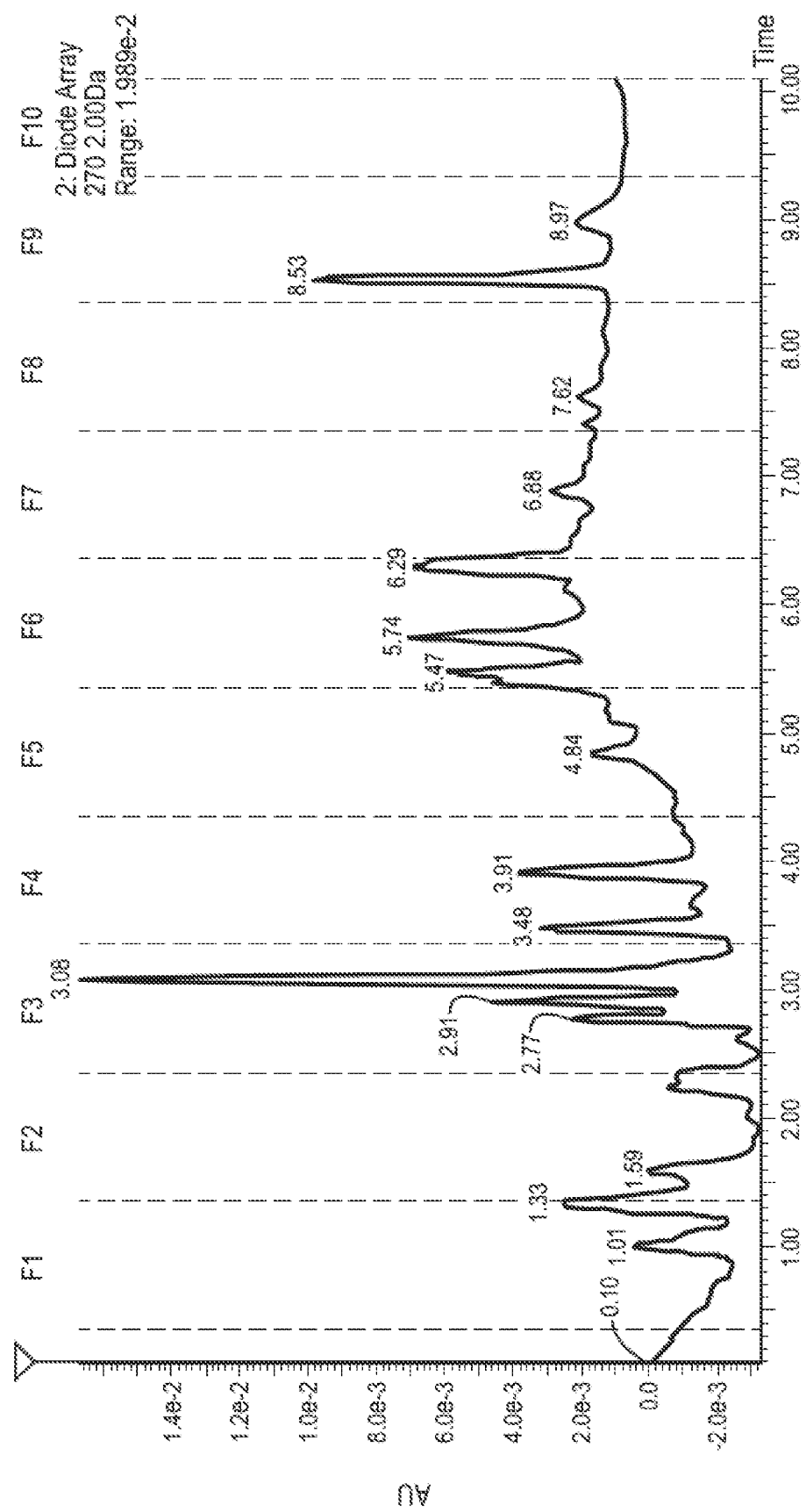
FIG. 7 depicts results of preparative-scale fractionation of a willow leaf extract using high performance liquid chromatography (HPLC), as described in Example 3.

In certain embodiments, a preparative-scale high performance liquid chromatography (HPLC) chromatogram of the willow leaf extract is substantially as shown in FIG. 7 using a diode array detector at 270 nm; wherein the chromatogram is obtained on a test sample prepared by the following procedure: an aliquot of powdered willow leaf extract is treated with boiling water (about 1 mL/10 mg willow leaf extract) at a temperature of about 100° C. for about 15 minutes, and the resulting mixture is cooled, then filtered through a filter of about 0.1 μm to about 0.5 μm to provide the test sample; and wherein the chromatographic method is:

| | |
|---|---|
| Column | XBridge Prep C18 19 × 100 mm |
| Mobile Phase A | Water with 100 mM Ammonium Acetate, pH 5.3 |
| Mobile Phase B | Acetonitrile |
| Gradient Method | Initial at 5% B, hold at 5% B for 0.5 minute, 5-35% B over 7.4 minutes, 35-95% B over 0.1 minute, hold at 95% B for 1 minute and return to initial conditions |
| Column Temperature | 25° C. |
| Sample Diluent | Methanol. |

In certain embodiments, the willow leaf extract was obtained according to a method described in Section III, below, including all combinations and permutations of the embodiments described therein.

Sixth Therapeutic Method

Another aspect of the invention provides a method for the treatment or prophylaxis of a condition selected from a coronavirus infection and allergic reaction in a patient. The method comprises orally administering to said patient in need thereof a therapeutically effective amount of a therapeutic composition comprising a willow extract. In certain embodiments, the method is for treatment of the condition. In certain embodiments, the method is for prophylaxis of the condition.

The method may be further characterized according to additional features, such as the condition. For example, in certain embodiments, the condition is a coronavirus infection. In certain embodiments, the condition is an allergic reaction. In certain embodiments, the condition is a respiratory allergic reaction. In certain embodiments, the condition is a respiratory allergic reaction due to an airborne allergen. In certain embodiments, the condition is an allergic reaction due to a food allergy. In certain embodiments, the condition is a dermatological allergic reaction.

In certain embodiments, the willow extract is the only active ingredient for treating the condition in the therapeutic composition.

In certain embodiments, the therapeutic composition contains at least one additional active ingredient for treating the condition, in addition to the willow extract.

Seventh Therapeutic Method

Another aspect of the invention provides a method of reducing inflammation in a patient suffering from a coronavirus infection. The method comprises orally administering to a patient in need thereof a therapeutically effective amount of a therapeutic composition comprising a willow extract, in order to reduce inflammation.

The method may be further characterized according to additional features, such as the presence of any additional active ingredients in the therapeutic composition. For example, in certain embodiments, the willow extract is the only active ingredient for reducing inflammation in the therapeutic composition. In certain other embodiments, the therapeutic composition contains at least one additional active ingredient for reducing inflammation, in addition to the willow extract.

Eighth Therapeutic Method

Another aspect of the invention provides a method of reducing the impact of a pro-inflammatory cytokine in a patient suffering from a coronavirus infection. The method comprises orally administering to a patient in need thereof a therapeutically effective amount of a therapeutic composition comprising a willow extract, in order to reduce the impact of the pro-inflammatory cytokine.

The method may be further characterized according to additional features, such as presence of any additional active ingredients in the therapeutic composition. For example, in certain embodiments, the willow extract is the only active ingredient for reducing the impact of a pro-inflammatory cytokine in the therapeutic composition. In certain other embodiments, the therapeutic composition contains at least one additional active ingredient for reducing the impact of a pro-inflammatory cytokine, in addition to the willow extract.

In certain embodiments, the pro-inflammatory cytokine is IL-1, IL-2, IL-6, IL-7, or IL-18. In certain embodiments, the pro-inflammatory cytokine is IL-1, IL-2, IL-6, or IL-7. In certain embodiments, the pro-inflammatory cytokine is IL-1. In certain embodiments, the pro-inflammatory cytokine is IL-1β. In certain embodiments, the pro-inflammatory cytokine is IL-2. In certain embodiments, the pro-inflammatory cytokine is IL-6. In certain embodiments, the pro-inflammatory cytokine is IL-7. In certain embodiments, the pro-inflammatory cytokine is IL-18.

In certain embodiments, the pro-inflammatory cytokine is IL-1, IL-2, IL-7, IL-6, IL-18, granulocyte-macrophage colony-stimulating factor (GM-CSF), vascular endothelial growth factor (VEGF), interferon-I (IFN-I), interferon-α (IFN-α), interferon-β (IFN-β), interferon-γ inducible protein 10 (IP-10), monocyte chemoattractant protein 1 (MCP-1), macrophage inflammatory protein 1-α (MIP-1α), or tumor necrosis factor-α (TNF-α). In certain embodiments, the pro-inflammatory cytokine is interferon-I (IFN-I), interferon-α (IFN-α), or interferon-β (IFN-β).

In certain embodiments, the pro-inflammatory cytokine is IL-2, IL-7, IL-6, granulocyte-macrophage colony-stimulating factor (GM-CSF), interferon-γ inducible protein 10 (IP-10), monocyte chemoattractant protein 1 (MCP-1), macrophage inflammatory protein 1-α (MIP-1α), or tumor necrosis factor-α (TNF-α). In certain embodiments, the pro-inflammatory cytokine is granulocyte-macrophage colony-stimulating factor (GM-CSF), interferon-γ inducible protein 10 (IP-10), monocyte chemoattractant protein 1 (MCP-1), macrophage inflammatory protein 1-α (MIP-1α), or tumor necrosis factor-α (TNF-α).

In certain embodiments, the impact of pro-inflammatory cytokine comprises increased inflammation. In certain embodiments, the impact of pro-inflammatory cytokine comprises respiratory failure, septic shock, fibrosis, and/or multi-organ failure. In certain embodiments, the impact of pro-inflammatory cytokine comprises fibrosis.

Ninth Therapeutic Method

Another aspect of the invention provides a method of treating a respiratory condition. The method comprises orally administering to a patient in need thereof a therapeutically effective amount of a therapeutic composition comprising a willow extract, to treat the respiratory condition.

The method may be further characterized according to additional features, such as the respiratory condition and the presence of any additional active ingredients in the therapeutic composition. For example, in certain embodiments, the respiratory condition is shortness of breath. In certain embodiments, the willow extract is the only active ingredient for treating the condition in the therapeutic composition. In certain other embodiments, the therapeutic composition contains at least one additional active ingredient for treating the condition, in addition to the willow extract.

Tenth Therapeutic Method

Another aspect of the invention provides a method of treating a medical condition. The method comprises administering to a patient in need thereof a therapeutically effective amount of a willow extract, to treat the medical condition.

The method may be further characterized according to additional features, such as the identity of the medical condition (e.g., where the medical condition is a coronavirus infection) and the presence of any additional active ingredients in the therapeutic composition. For example, in certain embodiments, the willow extract is the only active ingredient for treating the condition in the therapeutic composition. In certain other embodiments, the therapeutic composition contains at least one additional active ingredient for treating the medical condition, in addition to the willow extract.

Eleventh Therapeutic Method

Another aspect of the invention provides a method of reducing the amount of coronavirus in a subject. The method comprises administering to a patient in need thereof a therapeutically effective amount of a willow extract, to reduce the amount of coronavirus in the subject. The amount of coronavirus in a subject may be characterized according to the viral load of coronavirus in the subject. The method desirably reduces the viral load of coronavirus in the subject by at least 5%, 10%, 15,%, 20%, 30%, 40%, 50%, 60%, 70% 80%, or 90%.

The method may be further characterized according to additional features, such as the identity of the coronavirus infection, and the presence of any additional active ingredients in the therapeutic composition. For example, in certain embodiments, the willow extract is the only active ingredient for treating the condition in the therapeutic composition. In certain other embodiments, the therapeutic composition contains at least one additional active ingredient for treating the medical condition, in addition to the willow extract. In certain embodiments, the willow extract is willow leaf extract.

Twelfth Therapeutic Method

Another aspect of the invention provides a method of inhibiting the activity of a coronavirus in a subject. The method comprises administering to a patient in need thereof an effective amount of a willow extract, to inhibit the activity of the coronavirus. In certain embodiments, the activity of the coronavirus may be reduced by at least 5%, 10%, 15,%, 20%, 30%, 40%, 50%, 60%, 70% 80%, or 90%.

The method may be further characterized according to additional features, such as the identity of the coronavirus infection, and the presence of any additional active ingredients in the therapeutic composition. For example, in certain embodiments, the willow extract is the only active ingredient for treating the condition in the therapeutic composition. In certain other embodiments, the therapeutic composition contains at least one additional active ingredient for treating the medical condition, in addition to the willow extract. In certain embodiments, the willow extract is willow leaf extract.

Additional Features of the Sixth, Seventh, Eighth, and Tenth Therapeutic Methods Additional exemplary features that may characterize the Sixth, Seventh, Eighth, and Tenth Therapeutic Methods described herein are provided below and include, for example, the identity of the coronavirus infection and symptoms experienced by the patient. A more thorough description of such features is provided below. The invention embraces all permutations and combinations of these features.

Identity of Coronavirus

The methods may be further characterized according to the identity of the coronavirus infection. For example, in certain embodiments, the coronavirus infection is an infection by a severe acute respiratory syndrome-related coronavirus (SARSr-CoV). In certain embodiments, the coronavirus infection is an infection by a Sarbecovirus (beta-CoV lineage B). In certain embodiments, the coronavirus infection is an infection by SARS-CoV-2.

In certain embodiments, the coronavirus infection is an infection by a variant of SARS-CoV-2. In certain embodiments, the coronavirus infection is an infection by a variant of SARS-CoV-2 having the spike protein of SARS-CoV-2. In certain embodiments, the coronavirus infection is an infection by SARS-CoV-2 or a variant thereof selected from B.1.351, Cluster 5, Lineage B.1.1.207, Lineage B.1.1.7, Variant of Concern 202102/02, Lineage B.1.1.317, Lineage B.1.1.318, Lineage B.1.351, Lineage B.1.429, Lineage B.1.525, Lineage P.1, D614G, E484K, N501Y, S477G/N, and P681H. In certain embodiments, the coronavirus infection is an infection by SARS-CoV-2 or a variant thereof selected from B.1.617.2. In certain embodiments, the coronavirus infection is an infection by SARS-CoV-2 or a variant thereof selected from B.1.1.529, BA.2, C.37, B.1.621, B.1.429, B.1.427, CAL.20C, P.2, B.1.525, P.3, B.1.526, B.1.617.1, AZ.5, C.1.2, B.1.526, B.1.630, and B.1.640. In certain embodiments, the coronavirus infection is an infection by SARS-CoV-2 or a variant thereof selected from B.1.1.529 and BA.2.

In certain embodiments, the coronavirus infection is an infection by SARS-CoV-2 or variant thereof having a mutation at 1, 2, 3, 4, or 5 amino acids. In certain embodiments, the coronavirus infection is an infection by SARS-CoV-2 or variant thereof having a mutation at up to 10 amino acids. In certain embodiments, the coronavirus infection is an infection by SARS-CoV-2 or variant thereof having a mutation at up to 25 amino acids. In certain embodiments, the coronavirus infection is an infection by SARS-CoV-2 or variant thereof having a mutation at up to 35, 45, 55, or 65 amino acids.

Symptoms Experienced by the Patient

The methods may be further characterized according to symptoms experienced by the patient. For example, in certain embodiments, the patient presents with inflammation due to the coronavirus infection. In certain embodiments, the patient has inflammation in pulmonary tissue. In certain embodiments, the patient has mild or moderate respiratory distress. In certain embodiments, the patient has severe respiratory distress. In certain embodiments, the patient has pneumonia. In certain embodiments, the patient presents with one or more of respiratory failure, septic shock, or multi-organ failure. In certain embodiments, the patient is experiencing a hyper-immune response.

Additional Features of the Sixth, Seventh, Eighth, Ninth, and Tenth Therapeutic Methods Additional exemplary features that may characterize the Sixth, Seventh, Eighth, Ninth, and Tenth Therapeutic Methods described herein are provided below and include, for example, the dosage of willow extract, patients for treatment, and the identity of the willow extract. A more thorough description of such features is provided below. The invention embraces all permutations and combinations of these features.

In certain embodiments, the willow extract is the only active ingredient in the therapeutic composition. In certain embodiments, the therapeutic composition contains at least one additional active ingredient, in addition to the willow extract.

In certain embodiments, the method consists of orally administering to the patient in need thereof a therapeutically effective amount of the therapeutic composition comprising willow extract.

In certain embodiments, the method further comprises administering to the patient in need thereof a therapeutically effective amount of an additional therapeutic agent.

In certain embodiments, the therapeutic composition consists of (i) willow extract and (ii) optionally a pharmaceutically acceptable carrier.

In certain embodiments, the therapeutic composition comprises (i) willow extract, (ii) an additional therapeutic agent, and (iii) optionally a pharmaceutically acceptable carrier.

Dosage of Willow Extract

The methods may be further characterized according to the dosage of willow extract administered to the patient. For example, in certain embodiments, at least 2 g of willow extract is orally administered to the patient per day for at least 2 days. In certain embodiments, at least 2 g of willow extract is orally administered to the patient per day for at least 5 days. In certain embodiments, at least 2 g of willow extract is orally administered to the patient per day for at least 7 days.

In certain embodiments, at least 3 g of willow extract is orally administered to the patient per day for at least 2 days. In certain embodiments, at least 3 g of willow extract is orally administered to the patient per day for at least 5 days. In certain embodiments, at least 3 g of willow extract is orally administered to the patient per day for at least 7 days.

In certain embodiments, about 3 g of willow extract is orally administered to the patient per day for at least 2 days. In certain embodiments, about 3 g of willow extract is orally administered to the patient per day for at least 5 days. In certain embodiments, about 3 g of willow extract is orally administered to the patient per day for 5 days. In certain embodiments, about 3 g of willow extract is orally administered to the patient per day for at least 6 days. In certain embodiments, about 3 g of willow extract is orally administered to the patient per day for at least 7 days. In certain embodiments, about 3 g of willow extract is orally administered to the patient per day for 7 days.

In certain embodiments, from about 1 g to about 3 g of willow extract is orally administered to the patient per day. In certain embodiments, from about 1 g to about 3 g of willow extract is orally administered to the patient per day for at least 2 days. In certain embodiments, from about 1 g to about 3 g of willow extract is orally administered to the patient per day for at least 5 days. In certain embodiments, from about 1 g to about 3 g of willow extract is orally administered to the patient per day for 5 days. In certain embodiments, from about 1 g to about 3 g of willow extract is orally administered to the patient per day for at least 7 days. In certain embodiments, from about 1 g to about 3 g of willow extract is orally administered to the patient per day for 7 days.

Of course, actual dosage levels of the willow extract may be varied so as to obtain an amount which is effective to achieve the desired therapeutic response for a particular patient and extract, without being toxic to the patient. The selected dosage level will depend upon a variety of factors including the activity of the particular willow extract of the present invention employed, the time of administration, the duration of the treatment, other drugs, compounds and/or materials used in combination with the particular willow extract employed, the age, sex, weight, condition, general health and prior medical history of the patient being treated, and like factors well known in the medical arts.

A physician or veterinarian having ordinary skill in the art can readily determine and prescribe the effective amount of the willow extract required. For example, the physician or veterinarian could start doses of the willow extract at levels lower than that required in order to achieve the desired therapeutic effect and gradually increase the dosage until the desired effect is achieved.

Dosing Frequency of the Therapeutic Composition

The methods may be further characterized according to the frequency with which the therapeutic composition is administered to the patient. For example, in certain embodiments, a dose of the therapeutic composition is orally administered to the patient one to three times per day. In certain embodiments, a dose of the therapeutic composition is orally administered to the patient once per day. In certain embodiments, a dose of the therapeutic composition is orally administered to the patient at least once per day. In certain embodiments, a dose of the therapeutic composition is orally administered to the patient twice per day. In certain embodiments, a dose of the therapeutic composition is orally administered to the patient at least twice per day. In certain embodiments, a dose of the therapeutic composition is orally administered to the patient three times per day. In certain embodiments, a dose of the therapeutic composition is orally administered to the patient at least three times per day. In certain embodiments, a dose of the therapeutic composition is orally administered to the patient three times per day.

In certain embodiments, a dose of the therapeutic composition is orally administered to the patient at least two times per day for at least 2 days. In certain embodiments, a dose of the therapeutic composition is orally administered to the patient at least two times per day for at least 5 days. In certain embodiments, a dose of the therapeutic composition is orally administered to the patient at least two times per day for at least 7 days.

In certain embodiments, a dose of the therapeutic composition is orally administered to the patient three times per day for at least 2 days. In certain embodiments, a dose of the therapeutic composition is orally administered to the patient three times per day for at least 5 days. In certain embodiments, a dose of the therapeutic composition is orally administered to the patient three times per day for at least 7 days. In certain embodiments, a dose of the therapeutic composition is orally administered to the patient three times per day for 7 days.

In certain embodiments, a dose of the therapeutic composition is orally administered to the patient from one to three times per day for at least 2 days. In certain embodiments, a dose of the therapeutic composition is orally administered to the patient from one to three times per day for at least 5 days. In certain embodiments, a dose of the therapeutic composition is orally administered to the patient from one to three times per day for at least 7 days. In certain embodiments, a dose of the therapeutic composition is orally administered to the patient from one to three times per day for 7 to 10 days. In certain embodiments, a dose of the therapeutic composition is orally administered to the patient from one to three times per day for 7 to 14 days. In certain embodiments, a dose of the therapeutic composition is orally administered to the patient from one to three times per day for 7 days.

In certain embodiments, a dose of the therapeutic composition is orally administered to the patient three times per day for 7 to 10 days. In certain embodiments, a dose of the therapeutic composition is orally administered to the patient three times per day for 7 to 14 days. In certain embodiments, a dose of the therapeutic composition is orally administered to the patient three times per day for at least 7 days.

In certain embodiments, a dose of the therapeutic composition is orally administered at least once per day for at least 3 days each week. In certain embodiments, a dose of the therapeutic composition is orally administered at least once per day for at least 5 days each week. In certain embodiments, a dose of the therapeutic composition is orally administered at least once per day for at least 1 week. In certain embodiments, a dose of the therapeutic composition is orally administered at least once per day for at least 2 weeks. In certain embodiments, a dose of the therapeutic composition is orally administered at least once per day for at least 4, 6, 8, 10, 12, 14, 16, or 18 weeks.

In certain embodiments, a dose of the therapeutic composition is orally administered one to three times per day for at least 3 days each week. In certain embodiments, a dose of the therapeutic composition is orally administered one to three times per day for at least 5 days each week. In certain embodiments, a dose of the therapeutic composition is orally administered one to three times per day for at least 1 week. In certain embodiments, a dose of the therapeutic composition is orally administered one to three times per day for at least 2 weeks. In certain embodiments, a dose of the therapeutic composition is orally administered one to three times per day for at least 4, 6, 8, 10, 12, 14, 16, or 18 weeks.

In certain embodiments, a dose of the therapeutic composition is orally administered three times per day for at least 3 days each week. In certain embodiments, a dose of the therapeutic composition is orally administered three times per day for at least 5 days each week. In certain embodiments, a dose of the therapeutic composition is orally administered three times per day for at least 1 week. In certain embodiments, a dose of the therapeutic composition is orally administered three times per day for at least 2 weeks. In certain embodiments, a dose of the therapeutic composition is orally administered three times per day for at least 4, 6, 8, 10, 12, 14, 16, or 18 weeks.

Further, if desired, the effective daily dose of the therapeutic composition may be administered as two, three, four, five, six or more sub-doses administered separately at appropriate intervals throughout the day, optionally, in unit dosage forms. Preferred dosing is one to three administrations per day.

Amount of Willow Extract Per Dose of Therapeutic Composition

The methods may be further characterized according to the amount of willow extract in each dose of the therapeutic composition. For example, in certain embodiments, the dose of therapeutic composition contains at least about 0.5 g of willow extract. In certain embodiments, the dose of therapeutic composition contains at least about 0.75 g of willow extract. In certain embodiments, the dose of therapeutic composition contains at least about 1 g of willow extract. In certain embodiments, the dose of therapeutic composition contains from about 0.5 g to about 1.5 g of willow extract. In certain embodiments, the dose of therapeutic composition contains about 1 g of willow extract.

Of course, the actual amount of willow extract per dose of the therapeutic compositions may be varied so as to obtain an amount of the willow extract which is effective to achieve the desired therapeutic response for a particular patient, composition, and mode of administration, without being toxic to the patient. The selected dosage level will depend upon a variety of factors including the activity of the particular therapeutic composition of the present invention employed, the time of administration, the duration of the treatment, other drugs, compounds and/or materials used in combination with the particular therapeutic composition employed, the age, sex, weight, condition, general health and prior medical history of the patient being treated, and like factors well known in the medical arts.

A physician or veterinarian having ordinary skill in the art can readily determine and prescribe the effective amount of the therapeutic composition required. For example, the physician or veterinarian could start doses of the pharmaceutical composition at levels lower than that required in order to achieve the desired therapeutic effect and gradually increase the dosage until the desired effect is achieved.

Patients for Treatment

The methods may be further characterized according to patients for treatment. For example, in certain embodiments, the patient is an adult human. In certain embodiments, the patient is a pediatric human. In certain embodiments, the patient is a geriatric human.

Identity of the Willow Extract

The methods may be further characterized according to the identity of the willow extract. For example, in certain embodiments, the willow extract is willow leaf extract. In certain embodiments, the willow extract is willow bark extract.

In certain embodiments, the willow extract was obtained from young leaves of a willow tree. In certain embodiments, the willow extract was obtained from green leaves of a willow tree.

In certain embodiments, the willow extract was obtained from a willow tree located near standing water.

In certain embodiments, the willow extract was obtained from *Salix aegyptiaca, Salix alba, Salix amygdaloides, Salix arctica, Salix babylonica, Salix bebbiana, Salix caprea, Salix cinerea, Salix discolor, Salix exigua, Salix fragilis, Salix glauca, Salix herbacea, Salix integra, Salix laevigata, Salix lasiolepis, Salix microphylla, Salix nigra, Salix paradoxa, Salix pierotii, Salix purpurea, Salix scouleriana, Salix sepulcralis* group, *Salix tetrasperma, Salix triandra, Salix viminalis*, or a combination thereof. In certain embodiments, the willow extract was obtained from *Salix alba*.

In certain embodiments, the willow extract was obtained from a willow tree located in the Kurdistan region of Iraq. In certain embodiments, the willow extract was obtained from a willow tree located in the Barzan region of Iraq.

In certain embodiments, the willow extract was obtained from a willow tree during the month of May, June, July, August, and/or September.

In certain embodiments, the willow extract is further characterized according to the identity of one or more components in the willow extract. In certain embodiments, the willow extract comprises salicin (which has the chemical name (2R,3S,4S,5R,6S)-2-(hydroxymethyl)-6-[2-(hydroxymethyl)phenoxy]oxane-3,4,5-triol). In certain embodiments, the willow extract comprises salicin in an amount of at least 0.0001% w/w, 0.001% w/w, 0.01% w/w, 0.1% w/w, or 1% w/w of the willow extract. In certain embodiments, the willow extract comprises salicin in an amount of at least 1%, 2%, 3%, 4%, 5%, 6%, 7%, 8%, 9%, or 10% w/w of the willow extract. In certain embodiments, the willow extract comprises salicin in an amount of from about 0.0001% w/w to about 0.001% w/w, about 0.001% w/w to about 0.01% w/w, about 0.01% w/w to about 0.1% w/w, or about 0.1% to about 1% w/w of the willow extract. In certain embodiments, the willow extract comprises salicin in an amount of from about 1% w/w to about 2% w/w, about 1% w/w to 3% w/w, about 1% w/w to about 4% w/w, about 1% w/w to about 5% w/w, about 1% w/w to about 6% w/w, about 1% w/w to about 7% w/w, about 1% to about 8% w/w, about 1% to about 9% w/w, or about 1% to about 10% w/w of the willow extract. In certain embodiments, the willow extract comprises salicin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, about 5% to about 8% w/w, about 5% w/w to about 9% w/w, or about 5% w/w to about 10% w/w of the willow extract. In certain embodiments, the willow extract comprises salicin in an amount of from about 6% w/w to about 9% w/w, about 6% w/w to about 10% w/w, about 6% w/w to about 11% w/w, about 7% w/w to about 10% w/w, about 7% w/w to about 11% w/w, about 7% w/w to about 12% w/w, about 8% w/w to about 11% w/w, about 8% w/w to about 12% w/w, about 8% w/w to about 13% w/w, about 9% w/w to about 11% w/w, about 9% w/w to about 12% w/w, about 9% w/w to about 13% w/w, about 9% w/w to about 14% w/w, about 10% w/w to about 13% w/w, about 10% w/w to about 14% w/w, about 10% w/w to about 15% w/w, about 11% w/w to about 14% w/w, about 11% w/w to about 15% w/w, about 11% w/w to about 16% w/w, about 12% w/w to about 15% w/w, about 12% w/w to about 16% w/w, about 12% w/w to about 17% w/w, about 13% w/w to about 16% w/w, about 13% w/w to about 17% w/w, about 13% w/w to about 18% w/w, about 14% w/w to about 17% w/w, about 14% w/w to about 18% w/w, about 14% w/w to about 19% w/w, about 15% w/w to about 20% w/w, or about 15% w/w to about 21% w/w of the willow extract. In certain embodiments, the willow extract comprises salicin in an amount of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% w/w of the willow extract. In certain embodiments, the willow extract comprises salicin in an amount of about 5%. In certain embodiments, the willow extract comprises less than 10% w/w, 9% w/w, 8% w/w, 7% w/w, 6% w/w, 5% w/w, 4% w/w, 3% w/w, 2% w/w, 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of salicin. In certain embodiments, the willow extract does not contain salicin.

In certain embodiments, the willow extract comprises salicylic acid (which has the chemical name (2-hydroxybenzoic acid). In certain embodiments, the willow extract comprises salicylic acid in an amount of at least 0.0001% w/w, 0.001% w/w, 0.01% w/w, 0.1% w/w, or 1% w/w of the willow extract. In certain embodiments, the willow extract comprises salicylic acid in an amount of from about 0.0001% w/w to about 0.001% w/w, about 0.001% w/w to about 0.01% w/w, about 0.01% w/w to about 0.1% w/w, or about 0.1% to about 1% w/w of the willow extract. In certain embodiments, the willow extract comprises less than 8% w/w, 7% w/w, 6% w/w, 5% w/w, 4% w/w, 3% w/w, 2% w/w, 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of salicylic acid. In certain embodiments, the willow extract does not contain salicylic acid.

In certain embodiments, the willow extract comprises salicortin. In certain embodiments, the willow extract comprises salicortin in an amount of at least 0.0001% w/w, 0.001% w/w, 0.01% w/w, 0.1% w/w, or 1% w/w of the willow extract. In certain embodiments, the willow extract comprises salicortin in an amount of at least 1%, 2%, 3%, 4%, 5%, 6%, 7%, 8%, 9%, or 10% w/w of the willow extract. In certain embodiments, the willow extract comprises salicortin in an amount of from about 0.0001% w/w to about 0.001% w/w, about 0.001% w/w to about 0.01% w/w, about 0.01% w/w to about 0.1% w/w, or about 0.1% to about 1% w/w of the willow extract. In certain embodiments, the willow extract comprises salicortin in an amount of from about 1% w/w to about 2% w/w, about 1% w/w to 3% w/w, about 1% w/w to about 4% w/w, about 1% w/w to about 5% w/w, about 1% w/w to about 6% w/w, about 1% w/w to about 7% w/w, about 1% to about 8% w/w, about 1% to about 9% w/w, or about 1% to about 10% w/w of the willow extract. In certain embodiments, the willow extract comprises salicortin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% to about 6% w/w, about 4% to about 7% w/w, or about 5% to about 8% w/w of the willow extract. In certain embodiments, the willow extract comprises less than 8% w/w, 7% w/w, 6% w/w, 5% w/w, 4% w/w, 3% w/w, 2% w/w, 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of salicortin. In certain embodiments, the willow extract does not contain salicortin.

In certain embodiments, the willow extract comprises 2'-O-acetylsalicortin. In certain embodiments, the willow extract comprises 2'-O-acetylsalicortin in an amount of at least 0.0001% w/w, 0.001% w/w, 0.01% w/w, 0.1% w/w, or 1% w/w of the willow extract. In certain embodiments, the willow extract comprises 2'-O-acetylsalicortin in an amount of at least 1%, 2%, 3%, 4%, 5%, 6%, 7%, 8%, 9%, 10%, 11%, 12%, 13%, 14%, or 15% w/w of the willow extract. In certain embodiments, the willow extract comprises 2'-O-acetylsalicortin in an amount of from about 0.0001% w/w to about 0.001% w/w, about 0.001% w/w to about 0.01% w/w, about 0.01% w/w to about 0.1% w/w, or about 0.1% to about 1% w/w of the willow extract. In certain embodiments, the willow extract comprises 2'-O-acetylsalicortin in an amount of from about 1% w/w to about 2% w/w, about 1% w/w to 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow extract. In certain embodiments, the willow extract comprises 2'-O-acetylsalicortin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, about 5% w/w to about 8% w/w, about 5% w/w to about 9% w/w, about 5% w/w to about 10% w/w, about 7% w/w to about 9% w/w, about 7% w/w to about 10% w/w, about 7% w/w to about 11% w/w, about 9% w/w to about 12% w/w, about 8% w/w to about 10% w/w, about 8% w/w to about 11% w/w, about 8% w/w to about 12% w/w, about 8% w/w to about 13% w/w, about 9% w/w to about 11% w/w, about 9% w/w to about 12% w/w, or about 9% w/w to about 13% w/w. In certain embodiments, the willow extract comprises less than 10% w/w, 9% w/w, 8% w/w, 7% w/w, 6% w/w, 5% w/w, 4% w/w, 3% w/w, 2% w/w, 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of 2'-O-acetylsalicortin. In certain embodiments, the willow extract does not contain 2'-O-acetylsalicortin.

In certain embodiments, the willow extract comprises tremulacin. In certain embodiments, the willow extract comprises tremulacin in an amount of at least 0.0001% w/w, 0.001% w/w, 0.01% w/w, 0.1% w/w, or 1% w/w of the willow extract. In certain embodiments, the willow extract comprises tremulacin in an amount of at least 1%, 2%, 3%, 4%, 5%, or 6% w/w of the willow extract. In certain embodiments, the willow extract comprises tremulacin in an amount of from about 0.0001% w/w to about 0.001% w/w, about 0.001% w/w to about 0.01% w/w, about 0.01% w/w to about 0.1% w/w, or about 0.1% to about 1% w/w of the willow extract. In certain embodiments, the willow extract comprises tremulacin in an amount of from about 0.5% w/w to about 1% w/w, about 0.5% w/w to about 2% w/w, about 1% w/w to about 2% w/w, about 1% w/w to about 3% w/w, about 1% w/w to about 4% w/w, about 2% w/w to about 3% w/w, about 2% to about 4% w/w, or about 2% to about 5% w/w of the willow extract. In certain embodiments, the willow extract comprises tremulacin in an amount of from about 0.5% w/w to about 1% w/w, about 0.5% w/w to about 2% w/w, about 1% w/w to about 2% w/w, about 1% w/w to about 3% w/w, about 1% w/w to about 4% w/w, about 2% w/w to about 3% w/w, about 2% to about 4% w/w, about 2% to about 5% w/w, or about 3% to about 5% w/w of the willow extract. In certain embodiments, the willow extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of tremulacin. In certain embodiments, the willow extract does not contain tremulacin.

In certain embodiments, the willow extract comprises picein. In certain embodiments, the willow extract comprises picein in an amount of at least 0.0001% w/w, 0.001% w/w, 0.01% w/w, 0.1% w/w, or 1% w/w of the willow extract. In certain embodiments, the willow extract comprises picein in an amount of from about 0.0001% w/w to about 0.001% w/w, about 0.001% w/w to about 0.01% w/w, about 0.01% w/w to about 0.1% w/w, or about 0.1% to about 1% w/w of the willow extract. In certain embodiments, the willow extract comprises picein in an amount of from about 0.001% w/w to about 0.01% w/w of the willow extract. In certain embodiments, the willow extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of picein. In certain embodiments, the willow extract does not contain picein.

In certain embodiments, the willow extract comprises catechin. In certain embodiments, the willow extract comprises catechin in an amount of at least 0.0001% w/w, 0.001% w/w, 0.01% w/w, 0.1% w/w, or 1% w/w of the willow extract. In certain embodiments, the willow extract comprises catechin in an amount of from about 0.0001% w/w to about 0.001% w/w, about 0.001% w/w to about 0.01% w/w, about 0.01% w/w to about 0.1% w/w, or about 0.1% to about 1% w/w of the willow extract. In certain embodiments, the willow extract comprises catechin in an amount of from about 0.01% w/w to about 0.1% w/w of the willow extract. In certain embodiments, the willow extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of catechin. In certain embodiments, the willow extract does not contain catechin.

In certain embodiments, the willow extract comprises p-coumaric acid. In certain embodiments, the willow extract comprises p-coumaric acid in an amount of at least 0.0001% w/w, 0.001% w/w, 0.01% w/w, 0.1% w/w, or 1% w/w of the willow extract. In certain embodiments, the willow extract comprises p-coumaric acid in an amount of from about 0.0001% w/w to about 0.001% w/w, about 0.001% w/w to about 0.01% w/w, about 0.01% w/w to about 0.1% w/w, or about 0.1% to about 1% w/w of the willow extract. In certain embodiments, the willow extract comprises p-coumaric acid in an amount of from about 0.01% w/w to about 0.1% w/w of the willow extract. In certain embodiments, the willow extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of p-coumaric acid. In certain embodiments, the willow extract does not contain p-coumaric acid In certain embodiments, the willow extract comprises saligenin. In certain embodiments, the willow extract comprises saligenin in an amount of at least 0.0001% w/w, 0.001% w/w, 0.01% w/w, 0.1% w/w, or 1% w/w of the willow extract. In certain embodiments, the willow extract comprises saligenin in an amount of at least 1%, 2%, 3%, 4%, 5%, 6%, 7%, 8%, 9%, or 10% w/w of the willow extract. In certain embodiments, the willow extract comprises saligenin in an amount of from about 0.0001% w/w to about 0.001% w/w, about 0.001% w/w to about 0.01% w/w, about 0.01% w/w to about 0.1% w/w, about 0.1% to about 0.5% w/w, or about 0.1% to about 1% w/w of the willow extract. In certain embodiments, the willow extract comprises saligenin in an amount of from about 1% w/w to about 2% w/w, about 1% w/w to 3% w/w, about 1% w/w to about 4% w/w, about 1% w/w to about 5% w/w, about 1% w/w to about 6% w/w, about 1% w/w to about 7% w/w, about 1% to about 8% w/w, about 1% to about 9% w/w, or about 1% to about 10% w/w of the willow extract. In certain embodiments, the willow extract comprises saligenin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% to about 6% w/w, about 4% to about 7% w/w, or about 5% to about 8% w/w of the willow extract. In certain embodiments, the willow extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of saligenin. In certain embodiments, the willow extract does not contain saligenin.

In certain embodiments, the willow extract comprises salidroside. In certain embodiments, the willow extract comprises salidroside in an amount of at least 0.0001% w/w, 0.001% w/w, 0.01% w/w, 0.1% w/w, or 1% w/w of the willow extract. In certain embodiments, the willow extract comprises salidroside in an amount of at least 1%, 2%, 3%, 4%, 5%, 6%, 7%, 8%, 9%, or 10% w/w of the willow extract. In certain embodiments, the willow extract comprises salidroside in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow extract. In certain embodiments, the willow extract comprises salidroside in an amount of from about 1% w/w to about 2% w/w, about 1% w/w to 3% w/w, about 1% w/w to about 4% w/w, about 1% w/w to about 5% w/w, about 1% w/w to about 6% w/w, about 1% w/w to about 7% w/w, about 1% to about 8% w/w, about 1% to about 9% w/w, or about 1% to about 10% w/w of the willow extract. In certain embodiments, the willow extract comprises salidroside in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow extract. In certain embodiments, the willow extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of salidroside. In certain embodiments, the willow extract does not contain salidroside.

In certain embodiments, the willow extract comprises triandrin. In certain embodiments, the willow extract comprises triandrin in an amount of at least 0.0001% w/w, 0.001% w/w, 0.01% w/w, 0.1% w/w, or 1% w/w of the willow extract. In certain embodiments, the willow extract comprises triandrin in an amount of at least 1%, 2%, 3%, 4%, 5%, 6%, 7%, 8%, 9%, or 10% w/w of the willow extract. In certain embodiments, the willow extract comprises triandrin in an amount of from about 0.0001% w/w to about 0.001% w/w, about 0.001% w/w to about 0.01% w/w, about 0.01% w/w to about 0.1% w/w, about 0.1% to about 0.5% w/w, or about 0.1% to about 1% w/w of the willow extract. In certain embodiments, the willow extract comprises triandrin in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% to about 8% w/w, about 1% to about 9% w/w, or about 1% to about 10% w/w of the willow extract. In certain embodiments, the willow extract comprises triandrin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% to about 6% w/w, about 4% to about 7% w/w, or about 5% to about 8% w/w of the willow extract. In certain embodiments, the willow extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, 0.00001% w/w of triandrin. In certain embodiments, the willow extract does not contain triandrin.

In certain embodiments, the willow extract comprises isosalipurposide. In certain embodiments, the willow extract comprises isosalipurposide in an amount of at least 0.0001% w/w, 0.001% w/w, 0.01% w/w, 0.1% w/w, or 1% w/w of the willow extract. In certain embodiments, the willow extract comprises isosalipurposide in an amount of at least 1%, 2%, 3%, 4%, 5%, 6%, 7%, 8%, 9%, or 10% w/w of the willow extract. In certain embodiments, the willow extract comprises isosalipurposide in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow extract. In certain embodiments, the willow extract comprises isosalipurposide in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% to about 10% w/w of the willow extract. In certain embodiments, the willow extract comprises isosalipurposide in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% to about 6% w/w, about 4% to about 7% w/w, or about 5% to about 8% w/w of the willow extract. In certain embodiments, the willow extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of isosalipurposide. In certain embodiments, the willow extract does not contain isosalipurposide In certain embodiments, the willow extract comprises naringenin-7-O-glucoside. In certain embodiments, the willow extract comprises naringenin-7-O-glucoside in an amount of at least 0.0001% w/w, 0.001% w/w, 0.01% w/w, 0.1% w/w, or 1% w/w of the willow extract. In certain embodiments, the willow extract comprises naringenin-7-O-glucoside in an amount of at least 1%, 2%, 3%, 4%, 5%, 6%, 7%, 8%, 9%, or 10% w/w of the willow extract. In certain embodiments, the willow extract comprises naringenin-7-O-glucoside in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow extract. In certain embodiments, the willow extract comprises naringenin-7-0-glucoside in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% to about 8% w/w, about 1% to about 9% w/w, or about 1% to about 10% w/w of the willow extract. In certain embodiments, the willow extract comprises naringenin-7-O-glucoside in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow extract. In certain embodiments, the willow extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of naringenin-7-O-glucoside. In certain embodiments, the willow extract does not contain naringenin-7-O-glucoside.

In certain embodiments, the willow extract comprises prunin. In certain embodiments, the willow extract comprises prunin in an amount of at least 0.0001% w/w, 0.001% w/w, 0.01% w/w, 0.1% w/w, or 1% w/w of the willow extract. In certain embodiments, the willow extract comprises prunin in an amount of at least 1%, 2%, 3%, 4%, 5%, 6%, 7%, 8%, 9%, or 10% w/w of the willow extract. In certain embodiments, the willow extract comprises prunin in an amount of from about 0.0001% w/w to about 0.001% w/w, about 0.001% w/w to about 0.01% w/w, about 0.01% w/w to about 0.1% w/w, about 0.1% to about 0.5% w/w, or about 0.1% w/w to about 1% w/w of the willow extract. In certain embodiments, the willow extract comprises prunin in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow extract. In certain embodiments, the willow extract comprises prunin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow extract. In certain embodiments, the willow extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of prunin. In certain embodiments, the willow extract does not contain prunin.

In certain embodiments, the willow extract comprises ampelopsin. In certain embodiments, the willow extract comprises ampelopsin in an amount of at least 0.0001% w/w, 0.001% w/w, 0.01% w/w, 0.1% w/w, or 1% w/w of the willow extract. In certain embodiments, the willow extract comprises ampelopsin in an amount of at least 1%, 2%, 3%, 4%, 5%, 6%, 7%, 8%, 9%, or 10% w/w of the willow extract. In certain embodiments, the willow extract comprises ampelopsin in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow extract. In certain embodiments, the willow extract comprises ampelopsin in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow extract. In certain embodiments, the willow extract comprises ampelopsin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow extract. In certain embodiments, the willow extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of ampelopsin. In certain embodiments, the willow extract does not contain ampelopsin.

In certain embodiments, the willow extract comprises benzoic acid. In certain embodiments, the willow extract comprises benzoic acid in an amount of at least 0.0001% w/w, 0.001% w/w, 0.01% w/w, 0.1% w/w, or 1% w/w of the willow extract. In certain embodiments, the willow extract comprises benzoic acid in an amount of at least 1%, 2%, 3%, 4%, 5%, 6%, 7%, 8%, 9%, or 10% w/w of the willow extract. In certain embodiments, the willow extract comprises benzoic acid in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow extract. In certain embodiments, the willow extract comprises benzoic acid in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow extract. In certain embodiments, the willow extract comprises benzoic acid in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow extract. In certain embodiments, the willow extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of benzoic acid. In certain embodiments, the willow extract does not contain benzoic acid.

In certain embodiments, the willow extract comprises populin. In certain embodiments, the willow extract comprises populin in an amount of at least 0.0001% w/w, 0.001% w/w, 0.01% w/w, 0.1% w/w, or 1% w/w of the willow extract. In certain embodiments, the willow extract comprises populin in an amount of at least 1%, 2%, 3%, 4%, 5%, 6%, 7%, 8%, 9%, or 10% w/w of the willow extract. In certain embodiments, the willow extract comprises populin in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow extract. In certain embodiments, the willow extract comprises populin in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow extract. In certain embodiments, the willow extract comprises populin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow extract. In certain embodiments, the willow extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of populin. In certain embodiments, the willow extract does not contain populin.

In certain embodiments, the willow extract comprises syringin. In certain embodiments, the willow extract comprises syringin in an amount of at least 0.0001% w/w, 0.001% w/w, 0.01% w/w, 0.1% w/w, or 1% w/w of the willow extract. In certain embodiments, the willow extract comprises syringin in an amount of at least 1%, 2%, 3%, 4%, 5%, 6%, 7%, 8%, 9%, or 10% w/w of the willow extract. In certain embodiments, the willow extract comprises syringin in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow extract. In certain embodiments, the willow extract comprises syringin in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow extract. In certain embodiments, the willow extract comprises syringin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow extract. In certain embodiments, the willow extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of syringin. In certain embodiments, the willow extract does not contain syringin.

In certain embodiments, the willow extract comprises salireposide. In certain embodiments, the willow extract comprises salireposide in an amount of at least 0.0001% w/w, 0.001% w/w, 0.01% w/w, 0.1% w/w, or 1% w/w of the willow extract. In certain embodiments, the willow extract comprises salireposide in an amount of at least 1%, 2%, 3%, 4%, 5%, 6%, 7%, 8%, 9%, or 10% w/w of the willow extract. In certain embodiments, the willow extract comprises salireposide in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow extract. In certain embodiments, the willow extract comprises salireposide in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow extract. In certain embodiments, the willow extract comprises salireposide in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow extract. In certain embodiments, the willow extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of salireposide. In certain embodiments, the willow extract does not contain salireposide.

In certain embodiments, the willow extract comprises 2'-O-acetylsalicin. In certain embodiments, the willow extract comprises 2'-O-acetylsalicin in an amount of at least 0.0001% w/w, 0.001% w/w, 0.01% w/w, 0.1% w/w, or 1% w/w of the willow extract. In certain embodiments, the willow extract comprises 2'-O-acetylsalicin in an amount of at least 1%, 2%, 3%, 4%, 5%, 6%, 7%, 8%, 9%, 10%, 11%, 12%, 13%, 14%, or 15% w/w of the willow extract. In certain embodiments, the willow extract comprises 2'-O-acetylsalicin in an amount of from about 0.0001% w/w to about 0.001% w/w, about 0.001% w/w to about 0.01% w/w, about 0.01% w/w to about 0.1% w/w, or about 0.1% to about 1% w/w of the willow extract. In certain embodiments, the willow extract comprises 2'-O-acetylsalicin in an amount of from about 1% w/w to about 2% w/w, about 1% w/w to 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow extract. In certain embodiments, the willow extract comprises 2'-O-acetylsalicin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, about 5% w/w to about 8% w/w, about 5% w/w to about 9% w/w, about 5% w/w to about 10% w/w, about 7% w/w to about 9% w/w, about 7% w/w to about 10% w/w, about 7% w/w to about 11% w/w, about 9% w/w to about 12% w/w, about 8% w/w to about 10% w/w, about 8% w/w to about 11% w/w, about 8% w/w to about 12% w/w, about 8% w/w to about 13% w/w, about 9% w/w to about 11% w/w, about 9% w/w to about 12% w/w, or about 9% w/w to about 13% w/w. In certain embodiments, the willow extract comprises less than 10% w/w, 9% w/w, 8% w/w, 7% w/w, 6% w/w, 5% w/w, 4% w/w, 3% w/w, 2% w/w, 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of 2'-O-acetylsalicin. In certain embodiments, the willow extract does not contain 2'-O-acetylsalicin.

In certain embodiments, the willow extract comprises 6'-O-acetylsalicin. In certain embodiments, the willow extract comprises 6'-O-acetylsalicin in an amount of at least 0.0001% w/w, 0.001% w/w, 0.01% w/w, 0.1% w/w, or 1% w/w of the willow extract. In certain embodiments, the willow extract comprises 6'-O-acetylsalicin in an amount of at least 1%, 2%, 3%, 4%, 5%, 6%, 7%, 8%, 9%, 10%, 11%, 12%, 13%, 14%, or 15% w/w of the willow extract. In certain embodiments, the willow extract comprises 6'-O-acetylsalicin in an amount of from about 0.0001% w/w to about 0.001% w/w, about 0.001% w/w to about 0.01% w/w, about 0.01% w/w to about 0.1% w/w, or about 0.1% to about 1% w/w of the willow extract. In certain embodiments, the willow extract comprises 6'-O-acetylsalicin in an amount of from about 1% w/w to about 2% w/w, about 1% w/w to 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow extract. In certain embodiments, the willow extract comprises 6'-O-acetylsalicin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, about 5% w/w to about 8% w/w, about 5% w/w to about 9% w/w, about 5% w/w to about 10% w/w, about 7% w/w to about 9% w/w, about 7% w/w to about 10% w/w, about 7% w/w to about 11% w/w, about 9% w/w to about 12% w/w, about 8% w/w to about 10% w/w, about 8% w/w to about 11% w/w, about 8% w/w to about 12% w/w, about 8% w/w to about 13% w/w, about 9% w/w to about 11% w/w, about 9% w/w to about 12% w/w, or about 9% w/w to about 13% w/w. In certain embodiments, the willow extract comprises less than 10% w/w, 9% w/w, 8% w/w, 7% w/w, 6% w/w, 5% w/w, 4% w/w, 3% w/w, 2% w/w, 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of 6'-O-acetylsalicin. In certain embodiments, the willow extract does not contain 6'-O-acetylsalicin.

In certain embodiments, the willow extract comprises vimalin. In certain embodiments, the willow extract comprises vimalin in an amount of at least 0.0001% w/w, 0.001% w/w, 0.01% w/w, 0.1% w/w, or 1% w/w of the willow extract. In certain embodiments, the willow extract comprises vimalin in an amount of at least 1%, 2%, 3%, 4%, 5%, 6%, 7%, 8%, 9%, or 10% w/w of the willow extract. In certain embodiments, the willow extract comprises vimalin in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow extract. In certain embodiments, the willow extract comprises vimalin in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow extract. In certain embodiments, the willow extract comprises vimalin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow extract. In certain embodiments, the willow extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of vimalin. In certain embodiments, the willow extract does not contain vimalin.

In certain embodiments, the willow extract comprises grandidentatin. In certain embodiments, the willow extract comprises grandidentatin in an amount of at least 0.0001% w/w, 0.001% w/w, 0.01% w/w, 0.1% w/w, or 1% w/w of the willow extract. In certain embodiments, the willow extract comprises grandidentatin in an amount of at least 1%, 2%, 3%, 4%, 5%, 6%, 7%, 8%, 9%, or 10% w/w of the willow extract. In certain embodiments, the willow extract comprises grandidentatin in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow extract. In certain embodiments, the willow extract comprises grandidentatin in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow extract. In certain embodiments, the willow extract comprises grandidentatin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow extract. In certain embodiments, the willow extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of grandidentatin.

In certain embodiments, the willow extract comprises tremuloidin. In certain embodiments, the willow extract comprises tremuloidin in an amount of at least 0.0001% w/w, 0.001% w/w, 0.01% w/w, 0.1% w/w, or 1% w/w of the willow extract. In certain embodiments, the willow extract comprises tremuloidin in an amount of at least 1%, 2%, 3%, 4%, 5%, 6%, 7%, 8%, 9%, or 10% w/w of the willow extract. In certain embodiments, the willow extract comprises tremuloidin in an amount of from about 0.0001% w/w to about 0.001% w/w, about 0.001% w/w to about 0.01% w/w, about 0.01% w/w to about 0.1% w/w, about 0.1% w/w to about 0.5% w/w, or about 0.1% w/w to about 1% w/w of the willow extract. In certain embodiments, the willow extract comprises tremuloidin in an amount of from about 1% w/w to about 2% w/w, about 1% w/w to about 3% w/w, about 1% w/w to about 4% w/w, about 1% w/w to about 5% w/w, about 1% w/w to about 6% w/w, about 1% w/w to about 7% w/w, about 1% w/w to about 8% w/w, about 1% w/w to about 9% w/w, or about 1% w/w to about 10% w/w of the willow extract. In certain embodiments, the willow extract comprises tremuloidin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, or about 5% w/w to about 8% w/w of the willow extract. In certain embodiments, the willow extract comprises less than 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of tremuloidin. In certain embodiments, the willow extract does not contain tremuloidin.

In certain embodiments, the willow extract comprises fragilin. In certain embodiments, the willow extract comprises fragilin in an amount of at least 0.0001% w/w, 0.001% w/w, 0.01% w/w, 0.1% w/w, or 1% w/w of the willow extract. In certain embodiments, the willow extract comprises fragilin in an amount of from about 0.0001% w/w to about 0.001% w/w, about 0.001% w/w to about 0.01% w/w, about 0.01% w/w to about 0.1% w/w, or about 0.1% to about 1% w/w of the willow extract. In certain embodiments, the willow extract comprises less than 2% w/w, 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of fragilin. In certain embodiments, the willow extract does not contain fragilin.

The willow extract may be further characterized according to the chromatogram that results from analytical chromatography of the willow extract. For example, in certain embodiments, the willow extract when subjected to ultra performance liquid chromatography (UPLC) provides a chromatogram comprising peaks at retention times of about 4.33 minutes, about 5.40 minutes, about 7.90 minutes, about 11.96 minutes, and about 21.14 minutes using a diode array detector at 270 nm; wherein the chromatogram is obtained by UPLC on a test sample prepared by the following procedure: an aliquot of powdered willow extract is treated with boiling water (about 1 mL/10 mg willow extract) at a temperature of about 100° C. for about 15 minutes, and then the resulting mixture is cooled, then filtered through a filter of about 0.1 µm to about 0.5 µm to provide the test sample; and wherein the chromatographic method is:

| Column | Waters Acquity UPLC BEH C18 1.7 µm, 2.1 × 50 mm |
|---|---|
| Mobile Phase A | 0.1% Formic Acid in Water |
| Mobile Phase B | Acetonitrile |
| Gradient Method | 5-30% B over 20 min, 30-95% B in 1 min, hold 95% B for 2 min, 95-5% B in 0.1 min, hold 5% B for 1.9 min. |
| Flow Rate | 0.3 mL/min |
| Column Temperature | 40° C. |
| Sample Diluent | Water or Methanol. |

In certain embodiments, the analytical UPLC chromatogram of the willow extract further comprises peaks at one or more of the following retention times of about 1.46 minutes, about 5.15 minutes, about 6.28 minutes, about 8.07 minutes, about 13.68 minutes, and about 15.07 minutes. In certain embodiments, the analytical UPLC chromatogram of the willow extract further comprises peaks at retention times of about 1.46 minutes, about 5.15 minutes, about 6.28 minutes, about 8.07 minutes, about 13.68 minutes, and about 15.07 minutes. In certain embodiments, the analytical UPLC chromatogram of the willow extract further comprises peaks at retention times of about 1.29 minutes, about 1.95 minutes, about 4.01 minutes, about 5.88 minutes, about 9.16 minutes, about 9.88 minutes, about 11.62 minutes, about 12.35 minutes, about 13.02 minutes, about 16.18 minutes, about 17.39 minutes, and about 22.94 minutes. In certain embodiments, the analytical UPLC chromatogram of the willow extract further comprises peaks at one or more of the following retention times of about 1.29 minutes, about 1.95 minutes, about 4.01 minutes, about 5.88 minutes, about 9.16 minutes, about 9.88 minutes, about 11.62 minutes, about 12.35 minutes, about 13.02 minutes, about 16.18 minutes, about 17.39 minutes, and about 22.94 minutes.

In certain embodiments, each of the peaks has an intensity of at least 20% relative to the peak at retention time of about 4.33 minutes. In certain embodiments, each of the peaks has an intensity of at least 10% relative to the peak at retention time of about 4.33 minutes. In certain embodiments, each of the peaks has an intensity of at least 5% relative to the peak at retention time of about 4.33 minutes.

In certain embodiments, an analytical ultra performance liquid chromatography (UPLC) chromatogram of the willow extract is substantially as shown in FIG. 4 using a diode array detector at 270 nm; wherein the chromatogram is obtained by UPLC on a test sample prepared by the following procedure: an aliquot of powdered willow extract is treated with boiling water (about 1 mL/10 mg willow extract) at a temperature of about 100° C. for about 15 minutes, and then the resulting mixture is cooled, then filtered through a filter of about 0.1 μm to about 0.5 μm to provide the test sample; and wherein the chromatographic method is:

| Column | Waters Acquity UPLC BEH C18 1.7 μm, 2.1 × 50 mm |
|---|---|
| Mobile Phase A | 0.1% Formic Acid in Water |
| Mobile Phase B | Acetonitrile |
| Gradient Method | 5-30% B over 20 min, 30-95% B in 1 min, hold 95% B for 2 min, 95-5% B in 0.1 min, hold 5% B for 1.9 min. |
| Flow Rate | 0.3 mL/min |
| Column Temperature | 40° C. |
| Sample Diluent | Water or Methanol. |

In certain embodiments, a preparative-scale high performance liquid chromatography (HPLC) chromatogram of the willow extract comprises peaks at retention times of about 1.33 minutes, about 2.77 minutes, about 2.91 minutes, about 3.08 minutes, about 5.74 minutes, about 6.29 minutes, and about 8.53 minutes using a diode array detector at 270 nm; wherein the chromatogram is obtained on a test sample prepared by the following procedure: an aliquot of powdered willow extract is treated with boiling water (about 1 mL/10 mg willow extract) at a temperature of about 100° C. for about 15 minutes, and then the resulting mixture is cooled, then filtered through a filter of about 0.1 μm to about 0.5 μm to provide the test sample; and wherein the chromatographic method is:

| Column | XBridge Prep C18 19 × 100 mm |
|---|---|
| Mobile Phase A | Water with 100 mM Ammonium Acetate, pH 5.3 |
| Mobile Phase B | Acetonitrile |
| Gradient Method | Initial at 5% B, hold at 5% B for 0.5 minute, 5-35% B over 7.4 minutes, 35-95% B over 0.1 minute, hold at 95% B for 1 minute and return to initial conditions |
| Column Temperature | 25° C. |
| Sample Diluent | Methanol. |

In certain embodiments, the preparative-scale HPLC chromatogram of the willow extract further comprises peaks at one or more of the following retention times of about 1.01 minutes, about 1.59 minutes, about 3.48 minutes, about 3.91 minutes, and about 5.47 minutes. In certain embodiments, the preparative-scale HPLC chromatogram of the willow extract further comprises peaks at retention times of about 1.01 minutes, about 1.59 minutes, about 3.48 minutes, about 3.91 minutes, and about 5.47 minutes. In certain embodiments, the preparative-scale HPLC chromatogram of the willow extract further comprises peaks at one or more of the following retention times of about 2.21 minutes, 4.84 minutes, 5.37 minutes, about 6.88 minutes, about 7.62 minutes, and about 8.97 minutes. In certain embodiments, the preparative-scale HPLC chromatogram of the willow extract further comprises peaks at retention times of about 2.21 minutes, 4.84 minutes, 5.37 minutes, about 6.88 minutes, about 7.62 minutes, and about 8.97 minutes.

In certain embodiments, each of the peaks has an intensity of at least 20% relative to the peak at retention time of about 3.08 minutes. In certain embodiments, each of the peaks has an intensity of at least 10% relative to the peak at retention time of about 3.08 minutes. In certain embodiments, each of the peaks has an intensity of at least 5% relative to the peak at retention time of about 3.08 minutes.

In certain embodiments, a preparative-scale high performance liquid chromatography (HPLC) chromatogram of the willow extract is substantially as shown in FIG. 7 using a diode array detector at 270 nm; wherein the chromatogram is obtained on a test sample prepared by the following procedure: an aliquot of powdered willow extract is treated with boiling water (about 1 mL/10 mg willow extract) at a temperature of about 100° C. for about 15 minutes, and the resulting mixture is cooled, then filtered through a filter of about 0.1 μm to about 0.5 μm to provide the test sample; and wherein the chromatographic method is:

| Column | XBridge Prep C18 19 × 100 mm |
|---|---|
| Mobile Phase A | Water with 100 mM Ammonium Acetate, pH 5.3 |
| Mobile Phase B | Acetonitrile |
| Gradient Method | Initial at 5% B, hold at 5% B for 0.5 minute, 5-35% B over 7.4 minutes, 35-95% B over 0.1 minute, hold at 95% B for 1 minute and return to initial conditions |
| Column Temperature | 25° C. |
| Sample Diluent | Methanol. |

In certain embodiments, the willow leaf extract was obtained according to a method described in Section III, below, including all combinations and permutations of the embodiments described therein.

II. Combination Therapy

Another aspect of the invention provides for combination therapy. Willow extract, such as willow leaf extract, as well as therapeutic compositions and pharmaceutical compositions thereof, described herein may be used in combination with additional therapeutic agents to treat medical conditions (e.g., according to the methods described in Section I). Accordingly, in some embodiments, a method of the invention further comprises administering a therapeutically effective amount of an additional therapeutic agent.

In some embodiments, the present invention provides a method of treating a disclosed condition comprising administering to a patient in need thereof a therapeutically effective amount of willow extract, or a therapeutic composition or pharmaceutical composition thereof, described herein and co-administering simultaneously or sequentially an effective amount of one or more additional therapeutic agents, such as those described herein. In some embodiments, the present invention provides a method of treating a disclosed condition comprising administering to a patient in need thereof a therapeutically effective amount of willow leaf extract, or a therapeutic composition or pharmaceutical composition thereof, described herein and co-administering simultaneously or sequentially an effective amount of one or more additional therapeutic agents, such as those described herein.

In some embodiments, the method includes co-administering one additional therapeutic agent. In some embodiments, the method includes co-administering two additional therapeutic agents. In some embodiments, the combination of willow extract, or a therapeutic composition or pharmaceutical composition thereof, described herein and the additional therapeutic agent or agents acts synergistically. In some embodiments, the combination of willow leaf extract, or a therapeutic composition or pharmaceutical composition thereof, described herein and the additional therapeutic agent or agents acts synergistically.

One or more other therapeutic agents may be administered separately from willow extract described herein, as part of a multiple dosage regimen. Alternatively, one or more other therapeutic agents may be part of a single dosage form, mixed together with willow extract described herein in a single composition. If administered as a multiple dosage regime, one or more other therapeutic agent and willow extract described herein may be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent and willow extract described herein are administered as a multiple dosage regimen more than 24 hours apart.

One or more other therapeutic agents may be administered separately from willow leaf extract described herein, as part of a multiple dosage regimen. Alternatively, one or more other therapeutic agents may be part of a single dosage form, mixed together with willow leaf extract described herein in a single composition. If administered as a multiple dosage regime, one or more other therapeutic agent and willow leaf extract described herein may be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent and willow leaf extract described herein are administered as a multiple dosage regimen more than 24 hours apart.

The doses and dosage regimen of the active ingredients used in the combination therapy may be determined by an attending clinician. In certain embodiments, willow extract described herein and the additional therapeutic agent(s) (e.g., the second, third, or fourth, or fifth therapeutic agent, described below) are administered in doses commonly employed when such agents are used as monotherapy for treating the condition. In other embodiments, willow extract described herein and the additional therapeutic agent(s) (e.g., the second, third, or fourth, or fifth therapeutic agent, described below) are administered in doses lower than the doses commonly employed when such agents are used as monotherapy for treating the condition. In certain embodiments, the willow extract described herein and the additional therapeutic agent(s) (e.g., the second, third, or fourth, or fifth therapeutic agent, described below) are present in the same composition, which is suitable for oral administration. In certain embodiments, willow leaf extract described herein and the additional therapeutic agent(s) (e.g., the second, third, or fourth, or fifth therapeutic agent, described below) are administered in doses commonly employed when such agents are used as monotherapy for treating the condition. In other embodiments, willow leaf extract described herein and the additional therapeutic agent(s) (e.g., the second, third, or fourth, or fifth therapeutic agent, described below) are administered in doses lower than the doses commonly employed when such agents are used as monotherapy for treating the condition. In certain embodiments, the willow leaf extract described herein and the additional therapeutic agent(s) (e.g., the second, third, or fourth, or fifth therapeutic agent, described below) are present in the same composition, which is suitable for oral administration.

In certain embodiments, willow extract described herein and the additional therapeutic agent(s) (e.g., the second, third, or fourth, or fifth therapeutic agent, described below) may act additively or synergistically. In certain embodiments, willow leaf extract described herein and the additional therapeutic agent(s) (e.g., the second, third, or fourth, or fifth therapeutic agent, described below) may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

As indicated above, the invention embraces combination therapy, which includes the administration of willow extract, or a therapeutic composition or pharmaceutical composition thereof, described herein and a second agent as part of a specific treatment regimen intended to provide the beneficial effect from the co-action of these materials. As indicated above, the invention embraces combination therapy, which includes the administration of willow leaf extract, or a therapeutic composition or pharmaceutical composition thereof, described herein and a second agent as part of a specific treatment regimen intended to provide the beneficial effect from the co-action of these materials. The beneficial effect of the combination may include pharmacokinetic or pharmacodynamic co-action resulting from the combination of these materials.

Coronavirus Infection

Another aspect of the invention provides a method of treating a coronavirus infection in a patient. The method comprises administering to a patient in need thereof (i) a therapeutically effective amount of a therapeutic composition comprising a willow extract described herein and (ii) a second therapeutic agent, in order to treat the coronavirus infection.

Another aspect of the invention provides a method of treating a coronavirus infection in a patient. The method comprises administering to a patient in need thereof (i) a therapeutically effective amount of a therapeutic composition comprising a willow leaf extract described herein and (ii) a second therapeutic agent, in order to treat the coronavirus infection.

In certain embodiments, the second therapeutic agent is a corticosteroid, JAK inhibitor, NOX inhibitor, CYP-450 inhibitor, fusion inhibitor, entry inhibitor, protease inhibitor, polymerase inhibitor, antiviral nucleoside, viral entry inhibitor, viral maturation inhibitor, angiotensin-converting enzyme 2 (ACE2) inhibitor, SARS-CoV-specific human monoclonal antibody, platelet aggregation inhibitor, or anticoagulant.

In certain embodiments, the second therapeutic agent is an antiviral agent. In certain embodiments, the second therapeutic agent is a fusion inhibitor, entry inhibitor, protease inhibitor, polymerase inhibitor, antiviral nucleoside, viral entry inhibitor, viral maturation inhibitor, or SARS-CoV-specific human monoclonal antibody. In certain embodiments, the second therapeutic agent is a fusion inhibitor. In certain embodiments, the second therapeutic agent is umifenovir. In certain embodiments, the second therapeutic agent is an entry inhibitor. In certain embodiments, the second therapeutic agent is camostat, luteolin, or tetra-O-galloyl-β-D-glucose (TGG). In certain embodiments, the second therapeutic agent is a protease inhibitor. In certain embodiments, the second therapeutic agent is a polymerase inhibitor. In certain embodiments, the second therapeutic agent is an antiviral nucleoside. In certain embodiments, the second therapeutic agent is a viral entry inhibitor. In certain embodiments, the second therapeutic agent is a viral maturation inhibitor.

In certain embodiments, the second therapeutic agent is remdesivir. In certain embodiments, the second therapeutic agent is remdesivir and baricitinib.

In certain embodiments, the second therapeutic agent is a SARS-CoV-specific human monoclonal antibody. In certain embodiments, the second therapeutic agent is a human monoclonal antibody or antigen-binding fragment thereof that specifically binds to SARS-CoV-2 spike protein. In certain embodiments, the second therapeutic agent is bamlanivimab and etesevimab. In certain embodiments, the second therapeutic agent is bamlanivimab. In certain embodiments, the second therapeutic agent is etesevimab. In certain embodiments, the second therapeutic agent is casirivimab and imdevimab. In certain embodiments, the second therapeutic agent is casirivimab. In certain embodiments, the second therapeutic agent is imdevimab.

In certain embodiments, the second therapeutic agent is an anti-inflammatory agent. In certain embodiments, the second therapeutic agent is a corticosteroid, JAK inhibitor, IL-6 inhibitor, NOX inhibitor, CYP-450 inhibitor, or angiotensin-converting enzyme 2 (ACE2) inhibitor. In certain embodiments, the second therapeutic agent is a corticosteroid, JAK inhibitor, NOX inhibitor, CYP-450 inhibitor, or angiotensin-converting enzyme 2 (ACE2) inhibitor. In certain embodiments, the second therapeutic agent is a NOX inhibitor. In certain embodiments, the second therapeutic agent is ebselen, neopterin, apocynin, diapocynin, or a pharmaceutically acceptable salt or prodrug of any of the foregoing. In certain embodiments, the second therapeutic agent is ebselen, neopterin, apocynin, or diapocynin. In certain embodiments, the second therapeutic agent is an angiotensin-converting enzyme 2 (ACE2) inhibitor. In certain embodiments, the second therapeutic agent is lacepril, captopril, zefnopril, enalapril, ramipril, quinapril, perindopril, lisinopril, benazepril, imidapril, trandolapril, cilazapril, or fosinopril.

In certain embodiments, the second therapeutic agent is a corticosteroid. In certain embodiments, the second therapeutic agent is dexamethasone, prednisone, or methylprednisolone. In certain embodiments, the second therapeutic agent is dexamethasone. In certain embodiments, the second therapeutic agent is prednisone. In certain embodiments, the second therapeutic agent is methylprednisolone.

In certain embodiments, the second therapeutic agent is a JAK inhibitor. In certain embodiments, the second therapeutic agent is ruxolitinib, tofacitinib, or baricitinib. In certain embodiments, the second therapeutic agent is ruxolitinib. In certain embodiments, the second therapeutic agent is tofacitinib. In certain embodiments, the second therapeutic agent is baricitinib.

In certain embodiments, the second therapeutic agent is an IL-6 inhibitor. In certain embodiments, the second therapeutic agent is a monoclonal antibody targeting the IL-6 receptor. In certain embodiments, the second therapeutic agent is tocilizumab or sarilumab. In certain embodiments, the second therapeutic agent is tocilizumab. In certain embodiments, the second therapeutic agent is tocilizumab and dexamethasone. In certain embodiments, the second therapeutic agent is sarilumab.

In certain embodiments, the second therapeutic agent is a monoclonal antibody targeting IL-6. In certain embodiments, the second therapeutic agent is siltuximab or clazakizumab. In certain embodiments, the second therapeutic agent is siltuximab. In certain embodiments, the second therapeutic agent is clazakizumab.

In certain embodiments, the second therapeutic agent is a platelet aggregation inhibitor. In certain embodiments, the second therapeutic agent is an anticoagulant. In certain embodiments, the second therapeutic agent is heparin or enoxaparin. In certain embodiments, the second therapeutic agent is heparin. In certain embodiments, the second therapeutic agent is enoxaparin.

In certain embodiments, the second therapeutic agent is a CYP-450 inhibitor.

In certain embodiments, the second therapeutic agent is an agent disclosed in Ghosh, A. K. et al., "Drug Development and Medicinal Chemistry Efforts Toward SARS-Coronavirus and Covid-19 Therapeutics," *Chem Med Chem* (2020) Vol. 15, pp. 1-27.

In certain embodiments, the second therapeutic agent is selected from the group consisting of infliximab, abatacept, SNG001, AZD7442, SAB-185, tixagevimab, cilgavimab, S-217622, sotrovimab, bebtelovimab, etesevimab, an interferon, PF-07321332, remdesivir, molnupiravir, S-217622, favipiravir, ensovibep, recombinant ACE-2, ivermectin, oleandrin, lopinavir, and ritonavir. In certain other embodiments, the second therapeutic agent is pyronaridine-artesunate, GT0918, CKD-314, novaferon, xagrotin, sarilumab, lenzilumab, AZD1222, CPI-006, fostamatinib, xagrotin, AZD1222, TD0069, nitazoxanide, CT-P63, CT-P66, ZF2001, INO-4800, ciclesonide, baricitinib, bamlanivimab, leronlimab, BNT162b2, UB-612, evolocumab, BNT162b1, BNT162b2, SNG001, niclosamid, anakinra, tociliziumab, tenofovir disoproxil, K-237, plitidepsin, rivaroxaban, LY3819253, LYB001, BBV152, Peginterferon Lambda-1A, bucillamine, molixan, XC221, or enoxaparin.

In certain embodiments, a method described herein further comprises administering to the patient a therapeutically effective amount of a therapeutic agent selected from the group consisting of infliximab, abatacept, SNG001, AZD7442, SAB-185, tixagevimab, cilgavimab, S-217622, sotrovimab, bebtelovimab, etesevimab, an interferon, PF-07321332, remdesivir, molnupiravir, S-217622, favipiravir, ensovibep, recombinant ACE-2, ivermectin, oleandrin, lopinavir, and ritonavir.

In certain embodiments, a method described herein further comprises administering to the patient a therapeutically effective amount of a therapeutic agent selected from infliximab, abatacept, SNG001, AZD7442, SAB-185, tixagevimab, cilgavimab, S-217622, sotrovimab, bebtelovimab, etesevimab, an interferon, PF-07321332, remdesivir, molnupiravir, S-217622, favipiravir, ensovibep, recombinant ACE-2, ivermectin, oleandrin, lopinavir, and ritonavir. In certain other embodiments, the second therapeutic agent is pyronaridine-artesunate, GT0918, CKD-314, novaferon, xagrotin, sarilumab, lenzilumab, AZD1222, CPI-006, fostamatinib, xagrotin, AZD1222, TD0069, nitazoxanide, CT-P63, CT-P66, ZF2001, INO-4800, ciclesonide, baricitinib, bamlanivimab, leronlimab, BNT162b2, UB-612, evolocumab, BNT162b1, BNT162b2, SNG001, niclosamid, anakinra, tociliziumab, tenofovir disoproxil, K-237, plitidepsin, rivaroxaban, LY3819253, LYB001, BBV152, Peginterferon Lambda-1A, bucillamine, molixan, XC221, or enoxaparin.

In certain embodiments, the method further comprises administering to the subject a third therapeutic agent. In certain embodiments, the method further comprises administering to the subject a fourth therapeutic agent. In certain embodiments, the method further comprises administering to the subject a fifth therapeutic agent.

In certain embodiments, the third therapeutic agent is one of the second therapeutic agents described above. In certain embodiments, the fourth therapeutic agent is one of the second therapeutic agents described above. In certain embodiments, the fifth therapeutic agent is one of the second therapeutic agents described above.

Respiratory Conditions

Another aspect of the invention provides a method of treating a respiratory condition in a patient. The method comprises administering to a patient in need thereof (i) a therapeutically effective amount of a therapeutic composition comprising a willow extract described herein and (ii) a second therapeutic agent, in order to treat the respiratory condition.

Another aspect of the invention provides a method of treating a respiratory condition in a patient. The method comprises administering to a patient in need thereof (i) a therapeutically effective amount of a therapeutic composition comprising a willow leaf extract described herein and (ii) a second therapeutic agent, in order to treat the respiratory condition.

In certain embodiments, the respiratory condition is shortness of breath. In certain embodiments, the respiratory condition is asthma.

In certain embodiments, the second therapeutic agent is a fast-acting medication for treating acute symptoms. In certain embodiments, the second therapeutic agent is a short-acting $\beta_2$-adrenoceptor agonist. In certain embodiments, the second therapeutic agent is albuterol. In certain embodiments, the second therapeutic agent is an anticholinergic. In certain embodiments, the second therapeutic agent is ipratropium. In certain embodiments, the second therapeutic agent is an adrenergic agonist. In certain embodiments, the second therapeutic agent is epinephrine.

In certain embodiments, the second therapeutic agent is a medication used for long-term control of symptoms. In certain embodiments, the second therapeutic agent is a corticosteroid. In certain embodiments, the second therapeutic agent is a corticosteroid administered by inhalation. In certain embodiments, the second therapeutic agent is beclomethasone. In certain embodiments, the second therapeutic agent is a corticosteroid administered orally. In certain embodiments, the second therapeutic agent is a long-acting $\beta$-adrenoceptor agonist. In certain embodiments, the second therapeutic agent is salmeterol. In certain embodiments, the second therapeutic agent is formoterol. In certain embodiments, the second therapeutic agent is a leukotriene receptor antagonist. In certain embodiments, the second therapeutic agent is montelukast. In certain embodiments, the second therapeutic agent is zafirlukast. In certain embodiments, the second therapeutic agent is a 5-LOX inhibitor. In certain embodiments, the second therapeutic agent is zileuton.

In certain embodiments, the method further comprises administering to the subject a third therapeutic agent. In certain embodiments, the method further comprises administering to the subject a fourth therapeutic agent. In certain embodiments, the method further comprises administering to the subject a fifth therapeutic agent.

In certain embodiments, the third therapeutic agent is one of the second therapeutic agents described above. In certain embodiments, the fourth therapeutic agent is one of the second therapeutic agents described above. In certain embodiments, the fifth therapeutic agent is one of the second therapeutic agents described above.

III. Methods for Preparing Willow Leaf Extract

Another aspect of the invention provides a method for preparing a willow leaf extract. The method comprises the steps of:
a. obtaining leaves that have been harvested from a willow tree;
b. incubating said leaves in water at a temperature in excess of 50° C. to provide a mixture;
c. filtering the mixture produced from step (b) to isolate a liquid fraction;
d. exposing the liquid fraction to a temperature greater than ambient temperature to cause evaporation of water from the liquid fraction, thereby forming a paste; and
e. drying the paste to provide willow leaf extract.

Additional exemplary features that may characterize the method are provided below and include, for example, additional features of the steps listed above, additional steps the method may include, and the identity of the willow leaves. A more thorough description of such features is provided below. The invention embraces all permutations and combinations of these features.

Additional Features of Method Steps

The method may be further characterized according to additional features of steps (a) through (e). For example, in certain embodiments, step (b) comprises incubating the leaves in water at a temperature of about 100° C. to provide a mixture. In certain embodiments, the incubating in step (b) at said temperature is performed for a duration of at least 1 hour. In certain embodiments, the incubating in step (b) at said temperature is performed for a duration of about 2 hours.

In certain embodiments, step (b) is completed within 2 days of harvesting the leaves from a willow tree. In certain embodiments, step (b) is completed within 1 day of harvesting the leaves from a willow tree. In certain embodiments, step (b) is completed within 6 hours of harvesting the leaves from a willow tree.

In certain embodiments, step (d) comprises exposing the liquid fraction to a temperature greater than 50° C. to cause evaporation of water from the liquid fraction, thereby forming a paste. In certain embodiments, step (d) comprises exposing the liquid fraction to a temperature of about 100° C. to evaporate water from the liquid fraction, thereby forming a paste. In certain embodiments, step (d) comprises exposing the liquid fraction to a temperature of about 100° C. for a duration of about three hours to evaporate water from the liquid fraction, thereby forming a paste.

In certain embodiments, step (e) comprises drying the paste at ambient temperature to thereby provide willow leaf extract. In certain embodiments, step (e) comprises drying the paste at ambient temperature for a duration of at least seven days to thereby provide willow leaf extract. In certain embodiments, step (e) comprises drying the paste at ambient temperature for a duration of from about 10 days to about 14 days to thereby provide willow leaf extract.

Additional Steps the Method May Include

The method may be further characterized according to additional steps the method may include. For example, in certain embodiments, the method further comprises milling the willow leaf extract to provide willow leaf extract in powder form. In certain embodiments, the method further comprises, between step (a) and step (b) cleansing the leaves. The step of cleansing the leaves may use soap and water to cleanse the leaves.

Identity of the Willow Leaves

The method may be further characterized according to the identity of the willow leaves. For example, in certain embodiments, the leaves are young leaves of a willow tree. In certain embodiments, the leaves are green leaves of a willow tree. In certain embodiments, the leaves were harvested from a willow tree located near standing water.

In certain embodiments, the leaves are from a willow tree selected from *Salix aegyptiaca, Salix alba, Salix amygdaloides, Salix arctica, Salix babylonica, Salix bebbiana, Salix caprea, Salix cinerea, Salix discolor, Salix exigua, Salix fragilis, Salix glauca, Salix herbacea, Salix integra, Salix laevigata, Salix lasiolepis, Salix microphylla, Salix nigra, Salix paradoxa, Salix pierotii, Salix purpurea, Salix scouleriana, Salix sepulcralis* group, *Salix tetrasperma, Salix triandra, Salix viminalis*, or a combination thereof. In certain embodiments, the leaves are from a willow tree selected from *Salix alba*.

In certain embodiments, the leaves were harvested from a willow tree located in the Kurdistan region of Iraq. In certain embodiments, the leaves were harvested from a willow tree located in the Barzan region of Iraq.

In certain embodiments, the leaves were harvested from a willow tree during the month of May, June, July, August, and/or September.

IV. Willow Leaf Extract

Another aspect of the invention provides a willow leaf extract. The willow leaf extract comprises the material obtained by a method that comprises incubating willow leaves in water, then filtering the resulting mixture to isolate a liquid fraction, and converting the liquid fraction to a paste. Exemplary features that may characterize the willow leaf extract are provided below and include, for example, the physical form of the extract, the identity of the willow leaves used to produce the extract, and the method used to produce the willow leaf extract. A more thorough description of such features is provided below. The invention embraces all permutations and combinations of these features.

Physical Form of the Willow Leaf Extract

The willow leaf extract may be further characterized according to its physical form. For example, in certain embodiments, the willow leaf extract is a powder. In certain embodiments, the willow leaf extract is a solid. In certain embodiments, the willow leaf extract is an amorphous solid. In certain embodiments, the willow leaf extract is a paste.

In certain embodiments, the willow leaf extract is a liquid. In certain embodiments, the willow leaf extract is a viscous solution. In certain embodiments, the willow leaf extract is a suspension. In certain embodiments, the willow leaf extract is an aqueous solution. In certain embodiments, the willow leaf extract is a solution comprising water and at least one other solvent. In certain embodiments, the willow leaf extract is a solution comprising water and ethanol.

Identity of the Willow Leaves

The willow leaf extract may be further characterized according to the identity of the willow leaves used to produce the extract. For example, in certain embodiments, the willow leaves used to produce the extract are young leaves of a willow tree. In certain embodiments, the willow leaves used to produce the extract are green leaves of a willow tree. In certain embodiments, the willow leaves used to produce the extract were harvested from a willow tree located near standing water.

In certain embodiments, the willow leaves used to produce the extract are from a willow tree selected from *Salix aegyptiaca, Salix alba, Salix amygdaloides, Salix arctica, Salix babylonica, Salix bebbiana, Salix caprea, Salix cinerea, Salix discolor, Salix exigua, Salix fragilis, Salix glauca, Salix herbacea, Salix integra, Salix laevigata, Salix lasiolepis, Salix microphylla, Salix nigra, Salix paradoxa, Salix pierotii, Salix purpurea, Salix scouleriana, Salix sepulcralis* group, *Salix tetrasperma, Salix triandra, Salix viminalis*, or a combination thereof. In certain embodiments, the willow leaves used to produce the extract are from a willow tree selected from *Salix alba*.

In certain embodiments, the willow leaves used to produce the extract were harvested from a willow tree located in the Kurdistan region of Iraq. In certain embodiments, the willow leaves used to produce the extract were harvested from a willow tree located in the Barzan region of Iraq.

In certain embodiments, the willow leaves used to produce the extract were harvested from a willow tree during the month of May, June, July, August, and/or September.

Method for Producing the Willow Leaf Extract

The willow leaf extract may be further characterized according to the method used to produce the extract. For example, in certain embodiments, the willow leaf extract was produced by a method comprising the steps of:

a. obtaining leaves that have been harvested from a willow tree;
b. incubating said leaves in water at a temperature in excess of 50° C. to provide a mixture;
c. filtering the mixture produced from step (b) to isolate a liquid fraction;
d. exposing the liquid fraction to a temperature greater than ambient temperature to cause evaporation of water from the liquid fraction, thereby forming a paste; and
e. drying the paste to provide willow leaf extract.

The method may be further characterized according to additional features of steps (a) through (e) and/or additional steps that the method may include. For example, in certain embodiments, step (b) comprises incubating the leaves in water at a temperature of about 100° C. to provide a mixture. In certain embodiments, the incubating in step (b) at said temperature is performed for a duration of at least 1 hour. In certain embodiments, the incubating in step (b) at said temperature is performed for a duration of about 2 hours.

In certain embodiments, step (b) is completed within 2 days of harvesting the leaves from a willow tree. In certain embodiments, step (b) is completed within 1 day of harvesting the leaves from a willow tree. In certain embodiments, step (b) is completed within 6 hours of harvesting the leaves from a willow tree.

In certain embodiments, step (d) comprises exposing the liquid fraction to a temperature greater than 50° C. to cause evaporation of water from the liquid fraction, thereby forming a paste. In certain embodiments, step (d) comprises exposing the liquid fraction to a temperature of about 100° C. to evaporate water from the liquid fraction, thereby forming a paste. In certain embodiments, step (d) comprises exposing the liquid fraction to a temperature of about 100° C. for a duration of about three hours to evaporate water from the liquid fraction, thereby forming a paste.

In certain embodiments, step (e) comprises drying the paste at ambient temperature to thereby provide willow leaf extract. In certain embodiments, step (e) comprises drying the paste at ambient temperature for a duration of at least seven days to thereby provide willow leaf extract. In certain embodiments, step (e) comprises drying the paste at ambient temperature for a duration of from about 10 days to about 14 days to thereby provide willow leaf extract.

In certain embodiments, the method further comprises milling the willow leaf extract to provide willow leaf extract in powder form. In certain embodiments, the method further comprises, between step (a) and step (b) cleansing the leaves.

Identity of One or More Components in the Willow Leaf Extract

In certain embodiments, the willow leaf extract is further characterized according to the identity of one or more components in the willow leaf extract. In certain embodiments, the willow leaf extract comprises salicin (which has the chemical name (2R,3S,4S,5R,6S)-2-(hydroxymethyl)-6-[2-(hydroxymethyl)phenoxy]oxane-3,4,5-triol). In certain embodiments, the willow leaf extract comprises salicin in an amount of at least 0.0001% w/w, 0.001% w/w, 0.01% w/w, 0.1% w/w, or 1% w/w of the willow leaf extract. In certain embodiments, the willow leaf extract comprises salicin in an amount of from about 0.0001% w/w to about 0.001% w/w, about 0.001% w/w to about 0.01% w/w, about 0.01% w/w to about 0.1% w/w, or about 0.1% to about 1% w/w of the willow leaf extract. In certain embodiments, the willow extract comprises salicin in an amount of at least 1%, 2%, 3%, 4%, 5%, 6%, 7%, 8%, 9%, or 10% w/w of the willow extract. In certain embodiments, the willow extract comprises salicin in an amount of from about 0.0001% w/w to about 0.001% w/w, about 0.001% w/w to about 0.01% w/w, about 0.01% w/w to about 0.1% w/w, or about 0.1% to about 1% w/w of the willow extract. In certain embodiments, the willow extract comprises salicin in an amount of from about 1% w/w to about 2% w/w, about 1% w/w to 3% w/w, about 1% w/w to about 4% w/w, about 1% w/w to about 5% w/w, about 1% w/w to about 6% w/w, about 1% w/w to about 7% w/w, about 1% to about 8% w/w, about 1% to about 9% w/w, or about 1% to about 10% w/w of the willow extract. In certain embodiments, the willow extract comprises salicin in an amount of from about 2% w/w to about 3% w/w, about 2% w/w to about 4% w/w, about 2% w/w to about 5% w/w, about 3% w/w to about 5% w/w, about 3% w/w to about 6% w/w, about 3% w/w to about 7% w/w, about 4% w/w to about 6% w/w, about 4% w/w to about 7% w/w, about 5% to about 8% w/w, about 5% w/w to about 9% w/w, or about 5% w/w to about 10% w/w of the willow extract. In certain embodiments, the willow extract comprises salicin in an amount of from about 6% w/w to about 9% w/w, about 6% w/w to about 10% w/w, about 6% w/w to about 11% w/w, about 7% w/w to about 10% w/w, about 7% w/w to about 11% w/w, about 7% w/w to about 12% w/w, about 8% w/w to about 11% w/w, about 8% w/w to about 12% w/w, about 8% w/w to about 13% w/w, about 9% w/w to about 11% w/w, about 9% w/w to about 12% w/w, about 9% w/w to about 13% w/w, about 9% w/w to about 14% w/w, about 10% w/w to about 13% w/w, about 10% w/w to about 14% w/w, about 10% w/w to about 15% w/w, about 11% w/w to about 14% w/w, about 11% w/w to about 15% w/w, about 11% w/w to about 16% w/w, about 12% w/w to about 15% w/w, about 12% w/w to about 16% w/w, about 12% w/w to about 17% w/w, about 13% w/w to about 16% w/w, about 13% w/w to about 17% w/w, about 13% w/w to about 18% w/w, about 14% w/w to about 17% w/w, about 14% w/w to about 18% w/w, about 14% w/w to about 19% w/w, about 15% w/w to about 20% w/w, or about 15% w/w to about 21% w/w of the willow extract. In certain embodiments, the willow extract comprises salicin in an amount of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% w/w of the willow extract. In certain embodiments, the willow extract comprises salicin in an amount of about 5%. In certain embodiments, the willow extract comprises less than 10% w/w, 9% w/w, 8% w/w, 7% w/w, 6% w/w, 5% w/w, 4% w/w, 3% w/w, 2% w/w, 1% w/w, 0.5% w/w, 0.1% w/w, 0.05% w/w, 0.01% w/w, 0.005% w/w, 0.001% w/w, 0.0005% w/w, 0.0001% w/w, 0.00005% w/w, or 0.00001% w/w of salicin.

In certain embodiments, the willow leaf extract comprises salicylic acid (which has the chemical name (2-hydroxybenzoic acid). In certain embodiments, the willow leaf extract comprises salicylic acid in an amount of at least 0.0001% w/w, 0.001% w/w, 0.01% w/w, 0.1% w/w, or 1% w/w of the willow leaf extract. In certain embodiments, the willow leaf extract comprises salicylic acid in an amount of from about 0.0001% w/w to about 0.001% w/w, about 0.001% w/w to about 0.01% w/w, about 0.01% w/w to about 0.1% w/w, or about 0.1% to about 1% w/w of the willow leaf extract.

In certain embodiments, the willow leaf extract comprises one or more of the components described herein above in Section I. In certain embodiments, the willow leaf extract comprises one or more of the components in an amount as described herein above in Section I.

V. Pharmaceutical Compositions

As indicated above, the invention provides pharmaceutical compositions, which comprise a therapeutically effective amount of one or more of the compounds and/or willow extract, such as willow leaf extract, described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or nonaqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally. In a preferred embodiment, the pharmaceutical composition is formulated for oral administration.

In certain embodiments, the invention provides a pharmaceutical composition comprising a willow extract described herein (e.g., a willow extract described in Section I) and a pharmaceutically acceptable carrier. In certain embodiments, the invention provides a pharmaceutical composition comprising a willow extract described herein (e.g., a willow extract described in Section I), an additional therapeutic agent (e.g., a therapeutic agent described in Section II), and a pharmaceutically acceptable carrier.

In certain embodiments, the invention provides a pharmaceutical composition comprising a willow leaf extract described herein (e.g., a willow leaf extract prepared according to a method described in Section III) and a pharmaceutically acceptable carrier. In certain embodiments, the invention provides a pharmaceutical composition comprising a willow leaf extract described herein (e.g., a willow leaf extract prepared according to a method described in Section III), an additional therapeutic agent (e.g., a therapeutic agent described in Section II), and a pharmaceutically acceptable carrier.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound and/or willow extract, such as willow leaf extract, of the present invention as an active ingredient. A compound and/or willow extract, such as willow leaf extract, of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compound and/or willow extract, such as willow leaf extract, of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the compound and/or willow extract, such as willow leaf extract, may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compound and/or willow extract, such as willow leaf extract, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compound and/or willow extract, such as willow leaf extract, of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

VI. Compositions for Medical Use

Willow extract, such as willow leaf extract, described herein may be used to treat medical conditions described herein. For example, one aspect of the invention provides a willow leaf extract for use in treating a condition selected from a coronavirus infection and allergic reaction in a patient, wherein the willow leaf extract is for oral administration to the patient. In another example, another aspect of the invention provides a willow extract for use in treating a condition selected from a coronavirus infection and allergic reaction in a patient, wherein the willow extract is for oral administration to the patient.

Embodiments described herein in connection with the methods for treatment may be applied in connection with the willow extract or willow leaf extract for use.

VII. Preparation of a Medicament

Willow extract, such as willow leaf extract, described herein may be used in the preparation of a medicament to treat medical conditions described herein. For example, one aspect of the invention provides for the use of a willow leaf extract described herein in the preparation of a medicament for treating a condition selected from a coronavirus infection and allergic reaction in a patient, wherein the medicament is for oral administration to the patient. In another example, another aspect of the invention provides for the use of a willow extract described herein in the preparation of a medicament for treating a condition selected from a coronavirus infection and allergic reaction in a patient, wherein the medicament is for oral administration to the patient Embodiments described herein in connection with the methods for treatment may be applied in connection with the willow extract (e.g., willow leaf extract) for use in the preparation of a medicament.

VIII. Kits for Use in Medical Applications

Another aspect of the invention provides a kit for treating a medical condition and/or reducing inflammation or reducing the impact of a pro-inflammatory cytokine in a patient suffering from a coronavirus infection. The kit comprises: i) instructions for reducing inflammation or reducing the impact of a pro-inflammatory cytokine in a patient suffering from a coronavirus infection and/or treating a medical condition, such as a coronavirus infection, allergic reaction, or respiratory condition; and ii) a willow leaf extract, or a therapeutic composition or pharmaceutical composition thereof, described herein. The kit may comprise one or more unit dosage forms containing an amount of a willow leaf extract, or a therapeutic composition or pharmaceutical composition thereof, described herein. In certain embodiments, the kit comprises: i) instructions for reducing inflammation or reducing the impact of a pro-inflammatory cytokine in a patient suffering from a coronavirus infection and/or treating a medical condition, such as a coronavirus infection, allergic reaction, or respiratory condition; and ii) a willow extract, or a therapeutic composition or pharmaceutical composition thereof, described herein. The kit may comprise one or more unit dosage forms containing an amount of a willow extract, or a therapeutic composition or pharmaceutical composition thereof, described herein.

EXAMPLES

The invention now being generally described, will be more readily understood by reference to the following example, which is included merely for purposes of illustration of certain aspects and embodiments of the present invention, and is not intended to limit the invention.

Example 1—Preparation of Willow Leaf Extract and Capsules Containing Same

Willow leaf extract was prepared according to procedures described below. Capsules containing willow leaf extract were also prepared according to procedures described below.

Preparation of Willow Leaf Extract

Willow leaf extract was prepared according to the following procedure. Leaves were harvested from willow trees during the months of May, June, July, and August while the leaves are green. The willow trees were located in the Barzan region in Kurdistan, Iraq. The willow trees were located near standing water. After leaves were harvested from the willow trees, the leaves were subjected to the following procedure on the same day that the leaves were harvested from the willow trees:

a. Harvested willow tree leaves were cleansed using a mixture of mild soap and water at ambient temperature.
b. The cleansed willow leaf leaves were incubated in water at a temperature of about 100° C. for a duration of 2 hours. The mixture of water and willow tree leaves was observed to turn green.
c. The mixture of water and willow tree leaves was filtered for a duration of about 1 hour to isolate a liquid fraction. The willow tree leaves were pressed to facilitate removal of liquid from the willow tree leaf mass.
d. The liquid fraction from obtained from step (c) was subjected to elevated temperature suffice to cause the liquid in the liquid fraction to boil. The elevated temperature was maintained for a duration of about 3 hours until the liquid fraction forms a sticky paste.
e. The sticky paste was spread as a thin layer and permitted to dry at ambient temperature for a duration of from 10 days to 14 days, and the resulting material was milled to provide willow leaf extract in the form of a powder.

Preparation of Capsules Containing Willow Leaf Extract

Capsules containing willow leaf extract were prepared by placing 0.5 g of willow leaf extract in the form of a powder into the capsule.

Example 2—Treatment of SARS-CoV-2 Using Willow Leaf Extract

Human patients suffering from SARS-CoV-2 were orally administered willow leaf extract to treat the SARS-CoV-2 infection. Experimental procedures and results are provided below.

Part I—Experimental Procedures

Human patients suffering from a SARS-CoV-2 infection were orally administered capsules containing willow leaf extract. For the treatment protocol, patients were instructed to orally administer two capsules three times per day (i.e., every 8 hours) for a duration of 7 days. Each capsule contained 0.5 of willow leaf extract. This had the effect of administering a total amount of 21 grams of willow leaf extract to the patient during the treatment protocol period. Patients were not to take any other medication or supplement during the treatment protocol. Approximately 1,000 human patients were subjected to the treatment protocol, and patients were under the supervision of a physician during the treatment protocol. Human patients that completed the treatment protocol spanned a variety of ages, gender, demographic conditions, and pre-existing conditions. Exemplary pre-existing conditions observed in patients included diabetes, hypertension, and severe allergies.

Part II—Results

Greater than 95% of human patients that completed the treatment protocol showed complete recovery from the symptoms of SARS-CoV-2 infection. Treatment efficacy of the willow leaf extract was separately verified by the human patients having taken a PCR test for SARS-CoV-2 infection and received a negative result in the PCR test for SARS-CoV-2 infection within eight days after starting the treatment protocol. Patients suffering from more severe symptoms of SARS-CoV-2 infection (e.g., patients that were being treated using a ventilator or C-Pap machine) also responded well to therapy using the willow leaf extract. No adverse effects were observed due to taking the willow leaf extract. Five patients that at the time of starting the treatment protocol using willow leaf extract already had substantial progression of SARS-CoV-2 infection and presented with significant lung damage due to SARS-CoV-2 infection did not recover from the SARS-CoV-2 infection and died from complications of the SARS-CoV-2 infection. These five patients had been experiencing symptoms of SARS-CoV-2 infection for more than twelve days prior to the onset of therapy using the willow leaf extract.

Example 3—Chromatographic Characterization of Willow Leaf Extract

Willow leaf extract prepared according to procedures described in Example 1 was characterized using multiple extraction and chromatographic methods, as described below.

Chromatographic Methods

The following chromatographic methods were used in the experiments described below.

| Analytical Method 1 | |
| --- | --- |
| Column | Waters Acquity UPLC C18 2.1 × 50 mm |
| Mobile Phase A | 0.1% Formic Acid in Water |
| Mobile Phase B | Acetonitrile |
| Gradient Method | 5 to 95% B over 3 min, hold 95% B for 0.5 Min, return to 5% B in 0.01 min, hold 5% B for 0.49 min. |
| Column Temperature | 40° C. |
| Sample Diluent | Methanol |

| Analytical Method 2 | |
| --- | --- |
| Column | Waters Acquity UPLC C18 2.1 × 50 mm |
| Mobile Phase A | 0.1% Formic Acid in Water |
| Mobile Phase B | Acetonitrile |
| Gradient Method | Hold 5% B for 0.25 min, 5-50% B in 6.75 min, 50-95% B in 0.1 min, hold 95% B for 0.9 min, 95-5% B in 0.1 min, hold 5% B for 1.9 min. |
| Column Temperature | 40° C. |
| Sample Diluent | Methanol |

| Analytical Method 3 | |
| --- | --- |
| Column | Waters Acquity UPLC BEH C18 1.7 μm, 2.1 × 50 mm |
| Mobile Phase A | 0.1% Formic Acid in Water |
| Mobile Phase B | Acetonitrile |
| Gradient Method | 5-30% B over 20 min, 30-95% B in 1 min, hold 95% B for 2 min, 95-5% B in 0.1 min, hold 5% B for 1.9 min. |
| Flow Rate | 0.3 mL/min |
| Column Temperature | 40° C. |
| Sample Diluent | Water or Methanol |

| Preparative Method 1 | |
| --- | --- |
| Column | XBridge Prep C18 19 × 100 mm |
| Mobile Phase A | Water with 100 mM Ammonium Acetate, pH 5.3 |
| Mobile Phase B | Acetonitrile |
| Gradient Method | Initial at 5% B, hold at 5% B for 0.5 minute, 5-35% B over 7.4 minutes, 35-95% B over 0.1 minute, hold at 95% B for 1 minute and return to initial conditions |
| Column Temperature | 25° C. |
| Sample Diluent | Methanol |

| Preparative Method 2 | |
| --- | --- |
| Column | XBridge Prep C18 19 × 100 mm |
| Mobile Phase A | Water with 100 mM Ammonium Acetate, pH 5.3 |
| Mobile Phase B | Acetonitrile |
| Gradient Method | Initial at 10% B, 10-20% B over 0.78 minute, 20-30% B over 8.02 minutes, 30-90% B over 1.77 minute, hold at 95% B for 1.6 minute and return to initial conditions |
| Column Temperature | 25° C. |
| Sample Diluent | Methanol |

Additive in Aqueous Mobile Phase

The willow leaf extract was characterized by ultra performance liquid chromatography (UPLC) while varying the additive in the aqueous mobile phase. A sample of willow leaf extract was crushed into a homogeneous powder. The powder was treated with DMSO (1 mL/10 mg willow leaf extract) at 60° C. for 30 minutes, and then the resulting mixture was filtered through a 0.45 μm PTFE membrane to provide a final solution. The final solution was subjected to UPLC (using a diode array detector at 270 nm). FIG. 1 depicts chromatograms from the UPLC conducted on the final solution using Analytical Method 1 (top chromatogram), and the corresponding methods where 0.1% formic acid in water was replaced with 0.1% ammonium hydroxide in water (middle chromatogram) or 10 mM ammonium acetate (bottom chromatogram).

Extraction Conditions

Figure 2:
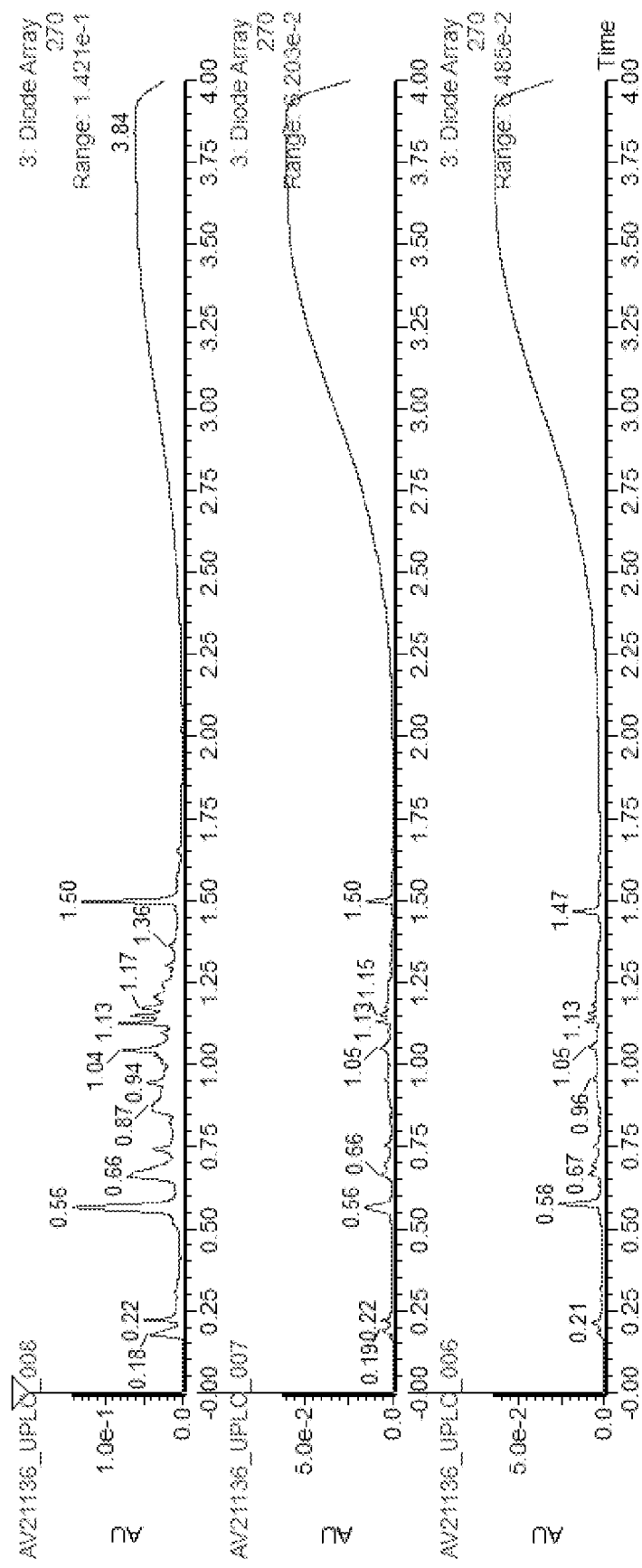
FIGS. 2 and 3 depict results of UPLC of a willow leaf extract varying the extraction conditions, as described in Example 3.
Figure 3:
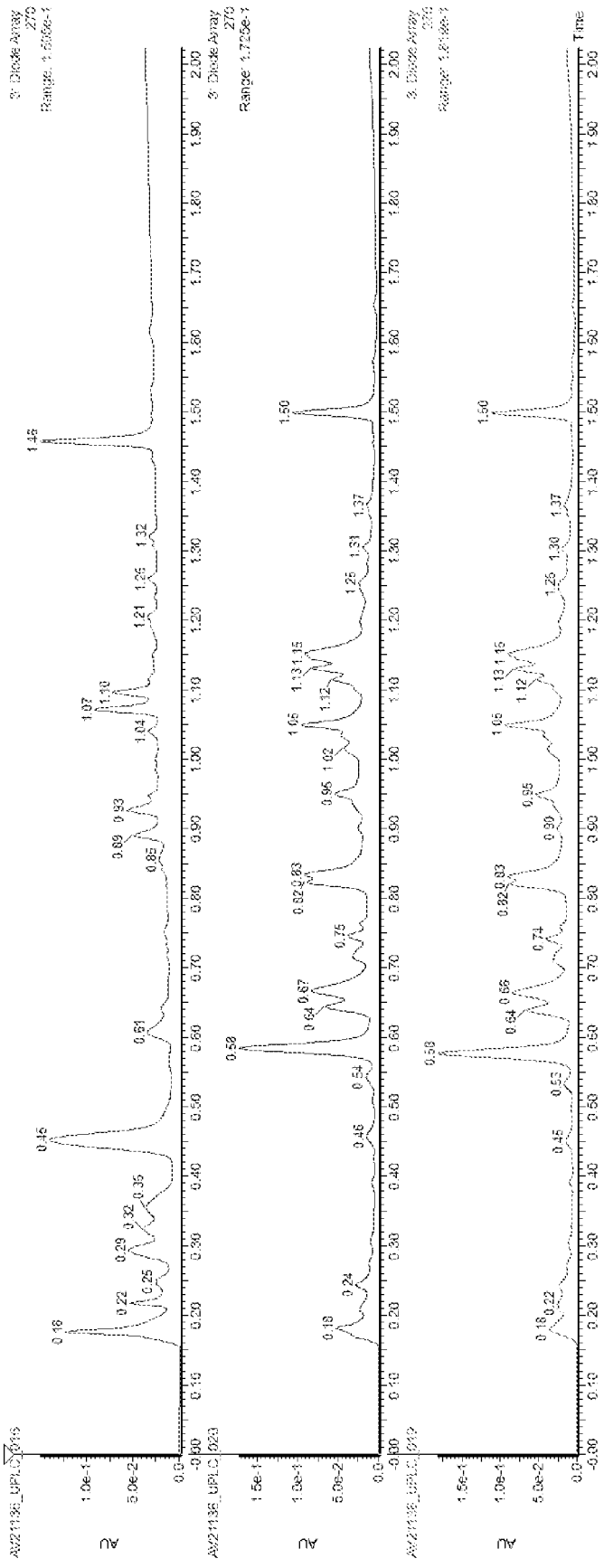

The willow leaf extract was subjected to differing further extraction conditions to produce a test sample, and the test sample was subjected UPLC. In this procedure, a sample of willow leaf extract was crushed into a homogeneous powder. The powder was treated with conditions described in Table 1 below, and the resulting mixture was then filtered through a 0.45 μm PTFE membrane to provide a test sample. FIGS. 2 and 3 depict chromatograms from UPLC of test samples using Analytical Method 1 (using a diode array detector at 270 nm), as specified in Table 1.

TABLE 1

| Extraction Conditions for Chromatographic Analysis | | |
| --- | --- | --- |
| Solvent | Temp., Time | Chromatogram |
| DMSO (1 mL/10 mg willow leaf extract) | 60° C., 30 min. | FIG. 2, Top and FIG. 3, Top |
| DMSO (1 mL/1 mg willow leaf extract) | 60° C., 30 min. | FIG. 2, Middle |
| Water (1 mL/1 mg willow leaf extract) | 60° C., 30 min. | FIG. 2, Bottom |
| 20 mM phosphate buffer in Water, pH 7.4 (1 mL/10 mg willow leaf extract) | 40° C., 60 min. | FIG. 3, Middle |
| 0.1M HCl in Water (1 mL/10 mg willow leaf extract) | 40° C., 60 min. | FIG. 3, Bottom |

Additionally, an aliquot of the powdered willow leaf extract was treated with boiling water (1 mL/10 mg willow leaf extract) at 100° C. for 15 minutes, then the resulting mixture was cooled, then filtered through a 0.45 μm PTFE syringe filter to provide a test sample. FIG. 4 depicts a chromatogram from UPLC of the test sample using Analytical Method 3 and a diode array detector at 270 nm.

In a preparative example, to 100 mg of finely ground willow leaf extract in a 20-mL scintillation vial with a stir bar was added 10 mL of boiling water. The resulting mixture was heated for 10 minutes with stirring, allowed to cool, and then filtered through a 1 μm glass syringe filter. The resulting filtrate was frozen and lyophilized, which afforded approximately 50 mg of solid sample.

Detection Methods

Figure 5:
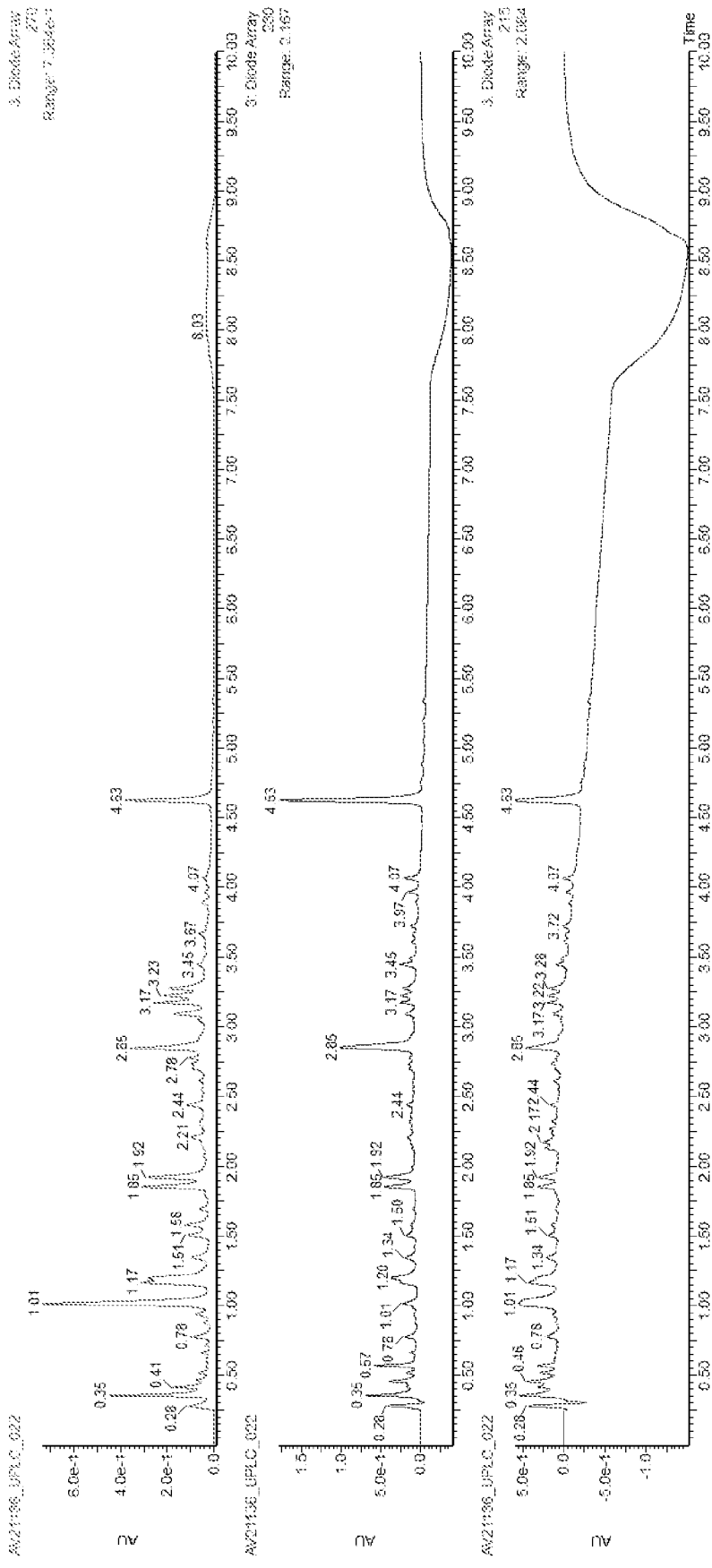
FIGS. 5 and 6 depict results of UPLC of a willow leaf extract varying the detection method, as described in Example 3.
Figure 6:
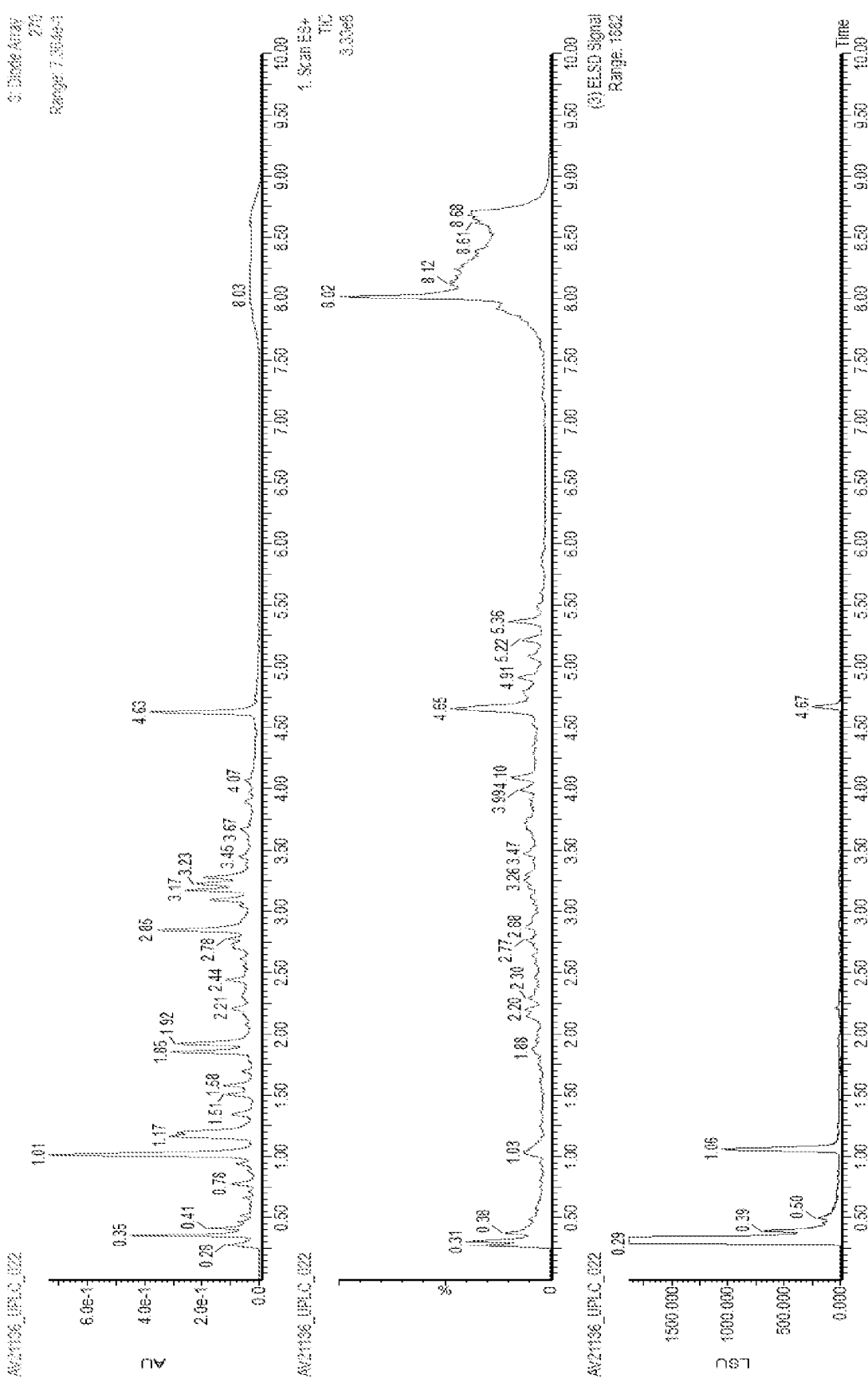

Willow leaf extract was characterized by UPLC using different detection methods. For this purpose, a sample of willow leaf extract was crushed into a homogeneous powder. The powder was treated with 0.1 M HCl in water (1 mL/10 mg willow leaf extract) at room temperature for 15 minutes, then the resulting mixture was filtered through a 0.45 μm PTFE membrane to provide a test solution. FIG. 5 depicts chromatograms from UPLC on the test solution using Analytical Method 2 using a diode array detector at 270 nm (top chromatogram), 230 nm (middle chromatogram), and 215 nm (bottom chromatogram). FIG. 6 depicts chromatograms for UPLC on the test solution using Analytical Method 2 using a diode array detector at 270 nm (top chromatogram), total ion count from a mass spectrometry detector using electrospray ionization in positive ionization mode (middle chromatogram), and an evaporative light-scattering detector (bottom chromatogram).

Preparative Fractionation

Figure 8:
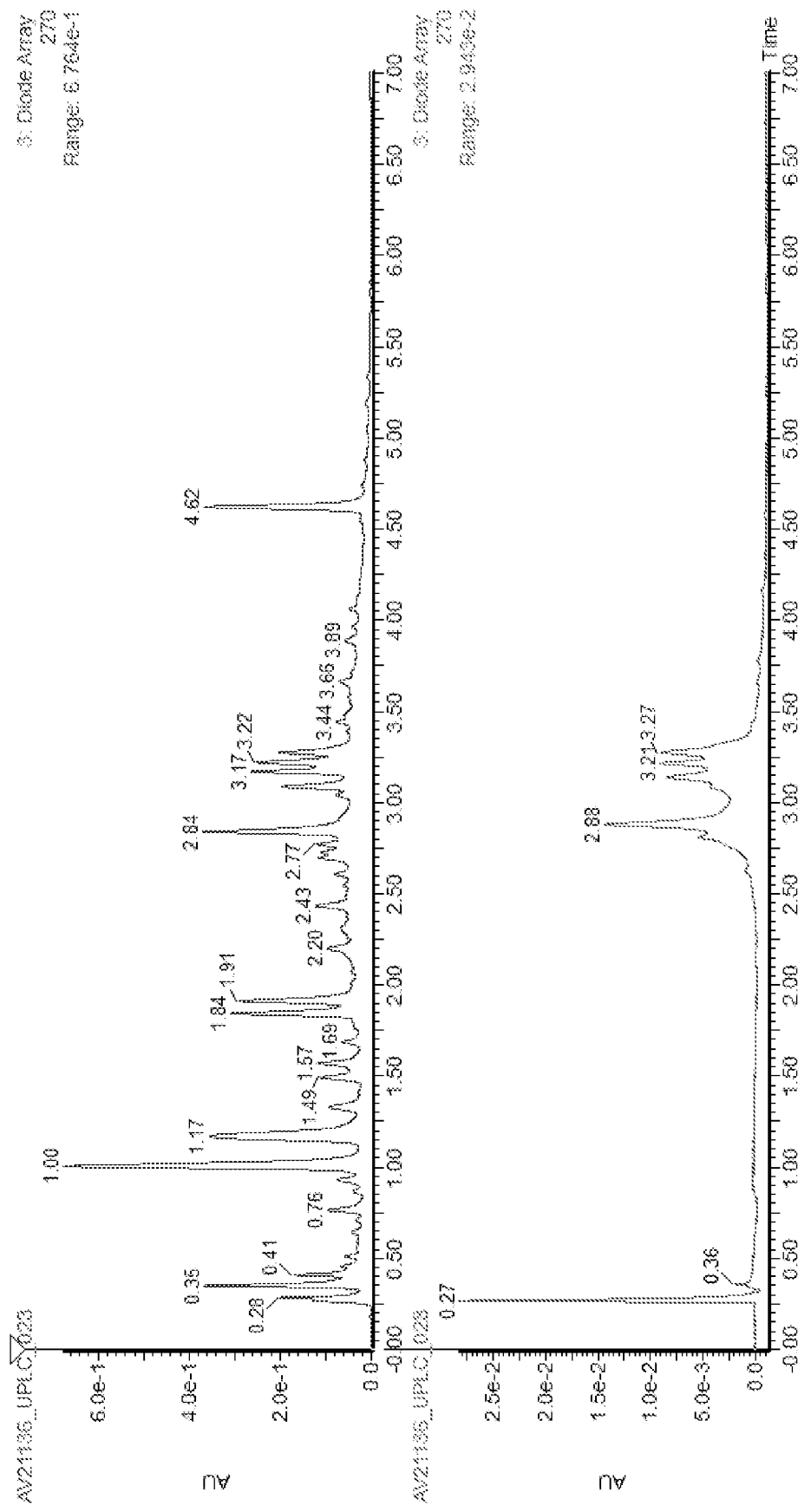
FIG. 8 depicts results of UPLC of a selected fraction from the preparative-scale fractionation of willow leaf extract, and the sample prior to fractionation, as described in Example 3.

The willow leaf extract was characterized by preparative-scale fractionation using high performance liquid chromatography (HPLC). An aliquot of willow leaf extract (approximately 500 mg) was crushed into a homogeneous powder. The powder was treated with hot water (50 mL) at 100° C. for 15 minutes, and then the resulting mixture was cooled, then filtered to provide a test sample. FIG. 7 depicts a chromatogram from HPLC on the test sample using Preparative Method 1 and a diode array detector at 270 nm. Ten time-based fractions were collected over the course of this preparative HPLC method, which are labeled F1 through F10 in FIG. 7. Table 2 provides the mass of each fraction following lyophilization, where available (the abbreviation "N/A" indicates data was not available). FIG. 8 depicts chromatograms using Analytical Method 2 and a diode array detector at 270 nm for the material before fractionation (top chromatogram) and the material obtained in fraction F6 (bottom chromatogram).

TABLE 2

Masses of Fractions Obtained from HPLC Fractionation of Willow Leaf Extract

| Fraction | Mass (mg) |
| --- | --- |
| F1 | 14.1 |
| F2 | 7.2 |
| F3 | 15.8 |
| F4 | 12.8 |
| F5 | 16.3 |
| F6 | N/A |
| F7 | 4.2 |
| F8 | 2.8 |
| F9 | 4.0 |
| F10 | 0.4 |

Figure 9:
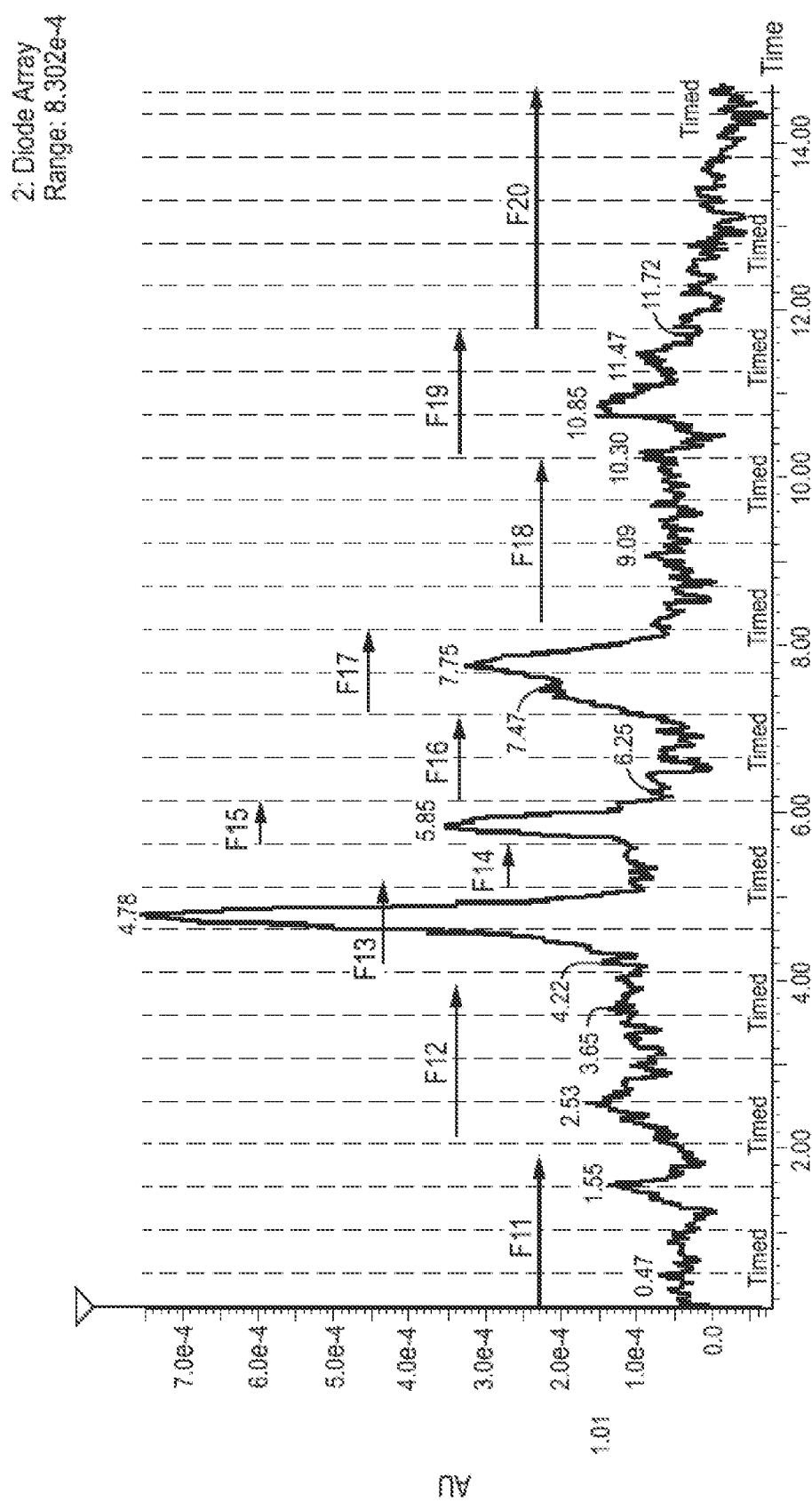
FIG. 9 depicts results of further preparative-scale fractionation of fraction F6 using high performance liquid chromatography (HPLC), as described in Example 3.

The material obtained in fraction F6 was characterized by further preparative-scale fractionation using high performance liquid chromatography (HPLC). FIG. 9 depicts a chromatogram from HPLC on fraction F6 using Preparative Method 2 and a UV diode array detector. Time-based fractions were collected over the course of this preparative HPLC method, as depicted by the vertical dashed lines in FIG. 9. Certain time-based fractions were combined, to generate a total of ten isolated fractions, labeled F11 through F20 in FIG. 9. Table 3 provides the approximate weight percent of each fraction following lyophilization (relative to the total weight of material in all of fractions F11 through F20 combined).

TABLE 3

Weight Percent of Fractions Obtained from Further Fractionation of Fraction F6

| Fraction | Approximate Weight Percent |
| --- | --- |
| F11 | 28 |
| F12 | 9 |
| F13 | 5 |
| F14 | 2 |
| F15 | 4 |
| F16 | 4 |
| F17 | 3 |
| F18 | 2 |
| F19 | 3 |
| F20 | 29 |

Comparison to Known Compounds

The willow leaf extract was characterized by comparison to commercially available samples of certain known compounds using ultra performance liquid chromatography (UPLC), mass spectrometry (MS), tandem mass spectrometry (MS/MS) and/or nuclear magnetic resonance spectroscopy (NMR). Results of these experiments are consistent with the presence in the willow leaf extract of each of the following compounds: salicin, p-coumaric acid, catechin, and picein.

Experimental results are consistent with salicin being a significant component of the willow leaf extract. A commercially available sample of salicin was determined to have a retention time of 10 minutes using Analytical Method 2 and a diode array detector at 270 nm (compare, for example, to the top chromatogram in FIG. 5). Additionally, a sample of approximately 10 mg of material of the peak at retention time 3.08 minutes using Preparative Method 1 (see FIG. 7) was isolated from the willow leaf extract. Comparison of the following parameters between (a) the commercial sample of salicin and (b) the material that forms the peak at retention time 3.08 minutes using Preparative Method 1 (see FIG. 7) established the identity of salicin in the willow leaf extract:

UPLC retention time,

High-resolution MS spectrum—electrospray negative ionization, major peaks at m/z 285.10474 ([M-H]$^-$, ~30% relative intensity) and 331.10909 ([M+formate]$^-$, 100% relative intensity), High-resolution MS/MS spectrum—electrospray negative ionization mode for the initial ion at m/z=331.10, major peaks at m/z=123.04761 (100% relative intensity) and 121.03174 (~40% relative intensity), $^1$H NMR spectrum in $CD_3OD$, and $^{13}$C NMR spectrum in $CD_3OD$.

The area of the UV peak due to salicin in the UPLC chromatogram of willow leaf extract, compared to the UV peak in the UPLC chromatogram of a commercially available sample of known concentration of salicin, is consistent with the willow leaf extract containing approximately 50 mg of salicin per one gram of willow leaf extract. That is, the willow leaf extract contained 5% w/w salicin.

Experimental results are consistent with p-coumaric acid being a component of the willow leaf extract. A commercially available sample of p-coumaric acid was determined to have a retention time of 9.16 minutes using Analytical Method 3 and a diode array detector at 270 nm (compare to FIG. 4). Additionally, the MS and MS/MS spectra for the commercial sample correspond to those for the peak at retention time of 9.16 minutes from the willow leaf extract using Analytical Method 3: electrospray negative ionization, MS major peak at m/z 163.0 [M-H]$^-$ with MS/MS peak at m/z 119.05. The area of the UV peak in the willow leaf extract, compared to the UV peak of the commercially available sample of known concentration, is consistent with the willow leaf extract containing approximately 0.7 mg p-coumaric acid per one gram of willow leaf extract.

Experimental results are consistent with catechin being a component of the willow leaf extract. A commercially available sample of catechin was determined to have a retention time of 5.65 minutes using Analytical Method 3 and a diode array detector at 270 nm (compare to FIG. 4). Additionally, the MS and MS/MS spectra for the commercial sample correspond to those for the peak at retention time of 5.65 minutes from the willow leaf extract using Analytical Method 3: electrospray negative ionization, MS major peak at m/z 289.0 [M-H]$^-$ with MS/MS major peaks at m/z 203.08 and 245.09. The area of the UV peak in the willow leaf extract, compared to the UV peak of the commercially available sample of known concentration, is consistent with the willow leaf extract containing approximately 0.2 mg catechin per one gram of willow leaf extract.

Experimental results are consistent with picein being a component of the willow leaf extract. A commercially available sample of picein was determined to have a retention time of 4.67 minutes using Analytical Method 3 and a diode array detector at 270 nm (compare to FIG. 4). Additionally, the MS and MS/MS spectra for the commercial sample correspond to those for the peak at retention time of 4.67 minutes from the willow leaf extract using Analytical Method 3: electrospray negative ionization, MS major peak at m/z 343.11 [M+formate]$^-$ with MS/MS major peak at m/z 135.05. The area of the UV peak in the willow leaf extract, compared to the UV peak of the commercially available sample of known concentration, is consistent with the willow leaf extract containing approximately 0.06 mg picein per one gram of willow leaf extract.

Comparison to Mass Spectrometric Data Reported in the Literature for Fragilin

An aliquot of powdered willow leaf extract was treated with boiling water (1 mL/10 mg willow leaf extract) at 100° C. for 15 minutes, then the resulting mixture was cooled, then filtered through a 0.45 μm PTFE syringe filter to provide a test sample. FIG. 4 depicts a chromatogram from UPLC of the test sample using Analytical Method 3 and a diode array detector at 270 nm. The test sample was subjected to HPLC-mass spectroscopic analysis to identify a molecular ion and fragmentation pattern for selected compounds in the test sample. A compound that eluted at 2.46 minutes using Analytical Method 3 to process the test sample had a MS major peak at m/z 327.1 and MS/MS fragmentation peaks at 123.1, 121.0, and 93.1. The aforementioned MS major peak at m/z 327.1 and MS/MS fragmentation peaks at 123.1, 121.0, and 93.1 generally align with the molecular ion and MS/MS fragmentation data reported for a reference standard of fragilin described by Kammerer et al. in *Phytochemical Analysis* (2005) vol. 16, 470-478.

Example 4—Activity in SARS-CoV-2 Cell-Based Assay

An aliquot of powdered willow leaf extract was treated with boiling water (1 mL/10 mg willow leaf extract) at 100° C. for 15 minutes, then the resulting mixture was cooled, then filtered through a 0.45 μm PTFE syringe filter to provide a test sample. FIG. 4 depicts a chromatogram from UPLC of the test sample using Analytical Method 3 and a diode array detector at 270 nm.

For the cell-based assay, Vero E6 cells were incubated with SARS-CoV-2 virus (isolate USA-WA1/2020, titer of viral stock is $1.75 \times 10^7$ pfu/mL) at 37° C. for 1 hour in assay plate wells. Thereafter, the P-Gp inhibitor compound CP-100356 was added to each well at a concentration of 2 μM, and test sample was added to designated wells at a concentration of 30 μM or 3 μM in dimethylsulfoxide (DMSO). Positive control wells were treated with remdesivir at 3 μM or 0.3 μM rather than test sample. The negative control wells were treated with DMSO without any test sample. Following incubation of cells after treatment with test sample, remdesivir, or DMSO alone, plate wells were analyzed to determine the number of viable Vero E6 cells, and the antiviral effects of the test compound and remdesivir towards SARS-CoV-2 virus were calculated. Experiments were performed in triplicate.

The test sample demonstrated a 10-15% antiviral effect towards SARS-CoV-2 virus when used at a concentration of 30 μM in the assay procedure described above.

Powdered willow leaf extract was tested in the above assay using powdered willow leaf extract at a concentration of 30 μM. Any antiviral affects were above the detection limit of this cell-based assay procedure when using powdered willow leaf extract at a concentration of 30 μm.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended embodiments rather than by the foregoing description, and all changes that come within the meaning and range of equivalency of the embodiments are intended to be embraced therein.

The invention claimed is:

1. A method of treating a condition that is a coronavirus infection in a patient, comprising orally administering to a patient in need thereof a therapeutically effective amount of a therapeutic composition comprising a willow leaf extract, to treat the condition.

2. The method of claim 1, wherein the willow leaf extract is the only active ingredient for treating the condition in the therapeutic composition.

3. The method of claim 1, wherein the method consists of orally administering to the patient in need thereof a therapeutically effective amount of the therapeutic composition comprising willow leaf extract.

4. The method of claim 1, wherein the coronavirus infection is an infection by a severe acute respiratory syndrome-related coronavirus (SARSr-CoV).

5. The method of claim 1, wherein the coronavirus infection is an infection by SARS-CoV-2.

6. The method of claim 1, wherein the coronavirus infection is an infection by a variant of SARS-CoV-2.

7. The method of claim 1, wherein the coronavirus infection is an infection by a variant of SARS-CoV-2 having the spike protein of SARS-CoV-2.

8. The method of claim 1, wherein the coronavirus infection is an infection by SARS-CoV-2 or a variant thereof selected from the group consisting of B.1.351, Cluster 5, Lineage B.1.1.207, Lineage B.1.1.7, Variant of Concern 202102/02, Lineage B.1.1.317, Lineage B.1.1.318, Lineage B.1.429, Lineage B.1.525, Lineage P.1, D614G, E484K, N501Y, S477G/N, and P681H.

9. The method of claim 1, wherein the coronavirus infection is an infection by SARS-CoV-2 or variant thereof having a mutation at up to 10 amino acids.

10. The method of claim 1, wherein the coronavirus infection is an infection by SARS-CoV-2 or variant thereof having a mutation at up to 25 amino acids.

11. The method of claim 1, wherein the patient presents with inflammation due to the coronavirus infection.

12. The method of claim 1, wherein the patient has inflammation in pulmonary tissue.

13. The method of claim 1, wherein the patient has mild or moderate respiratory distress.

14. The method of claim 1, wherein the patient has severe respiratory distress.

15. The method of claim 1, wherein the patient has pneumonia.

16. The method of claim 1, wherein the patient presents with one or more of respiratory failure, septic shock, or multi-organ failure.

17. The method of claim 1, wherein the patient is experiencing a hyper-immune response.

18. The method of claim 1, wherein the therapeutic composition consists of (i) willow leaf extract and (ii) optionally a pharmaceutically acceptable carrier.

19. The method of claim 1, wherein at least 3 g of willow leaf extract is orally administered to the patient per day for at least 5 days.

20. The method of claim 1, wherein at least 3 g of willow leaf extract is orally administered to the patient per day for at least 7 days.

21. The method of claim 1, wherein about 3 g of willow leaf extract is orally administered to the patient per day for at least 5 days.

22. The method of claim 1, wherein about 3 g of willow leaf extract is orally administered to the patient per day for at least 7 days.

23. The method of claim 1, wherein a dose of the therapeutic composition is orally administered to the patient three times per day.

24. The method of claim 1, wherein a dose of the therapeutic composition is orally administered to the patient three times per day for at least 7 days.

25. The method of claim 24, wherein the dose of therapeutic composition contains from about 0.5 g to about 1.5 g of willow leaf extract.

26. The method of claim 24, wherein the dose of therapeutic composition contains about 1 g of willow leaf extract.

27. The method of claim 1, wherein the patient is an adult human.

28. The method of claim 1, wherein the willow leaf extract was obtained from *Salix aegyptiaca, Salix alba, Salix amygdaloides, Salix arctica, Salix babylonica, Salix bebbiana, Salix caprea, Salix cinerea, Salix discolor, Salix exigua, Salix fragilis Salix glauca, Salix herbacea, Salix Integra, Salix laevigata, Salix lasiolepis, Salix microphylla, Salix nigra, Salix paradoxa, Salix pierotii, Salix purpurea, Salix scouleriana, Salix sepulcralis group, Salix tetrasperma, Salix triandra, Salix viminalis*, or a combination thereof.

\* \* \* \* \*